(12) United States Patent
Strobel et al.

(10) Patent No.: US 8,518,976 B2
(45) Date of Patent: Aug. 27, 2013

(54) HETEROARYL-SUBSTITUTED AMIDES COMPRISING A SATURATED LINKER GROUP, AND THEIR USE AS PHARMACEUTICALS

(75) Inventors: Harmut Strobel, Frankfurt (DE); Paulus Wohlfart, Frankfurt (DE); Gerhard Zoller, Frankfurt (DE); David William Will, Frankfurt (DE)

(73) Assignee: Sanofi, Paris (FR)

( * ) Notice: Subject to any disclaimer, the term of this patent is extended or adjusted under 35 U.S.C. 154(b) by 1464 days.

(21) Appl. No.: 11/958,483

(22) Filed: Dec. 18, 2007

(65) Prior Publication Data
US 2008/0171739 A1    Jul. 17, 2008

Related U.S. Application Data

(63) Continuation of application No. PCT/EP2006/005706, filed on Jun. 14, 2006.

(30) Foreign Application Priority Data

Jun. 28, 2005 (EP) .................................... 05013870

(51) Int. Cl.
   *C07D 401/12* (2006.01)
   *C07D 401/06* (2006.01)
(52) U.S. Cl.
   USPC ...................... 514/343; 546/278.4; 546/278.7
(58) Field of Classification Search
   USPC ............................ 546/278.4, 278.7; 514/343
   See application file for complete search history.

(56) References Cited

U.S. PATENT DOCUMENTS

| 3,655,684 | A | 4/1972 | Osbond et al. |
|---|---|---|---|
| 4,514,397 | A | 4/1985 | Wermuth et al. |
| 4,565,814 | A | 1/1986 | Kan et al. |
| 4,710,502 | A | 12/1987 | Wright, Jr. et al. |
| 5,190,589 | A | 3/1993 | Eriks et al. |
| 5,292,732 | A | 3/1994 | Roever et al. |
| 5,547,972 | A | 8/1996 | Clegg et al. |
| 7,179,839 | B2 | 2/2007 | Strobel et al. |
| 7,186,735 | B2 | 3/2007 | Strobel et al. |
| 8,242,281 | B2 | 8/2012 | Rosentreter et al. |
| 2003/0055093 | A1 | 3/2003 | Strobel et al. |
| 2003/0171359 | A1 | 9/2003 | Dahmann et al. |
| 2003/0199530 | A1 | 10/2003 | Goldstein et al. |
| 2003/0232860 | A1 | 12/2003 | Harada et al. |
| 2004/0102630 | A1 | 5/2004 | Brumby et al. |
| 2004/0162427 | A1 | 8/2004 | Rosentreter et al. |
| 2005/0159431 | A1 | 7/2005 | Albrecht et al. |
| 2007/0082897 | A1 | 4/2007 | Strobel et al. |
| 2007/0213372 | A1 | 9/2007 | Rosentreter et al. |

FOREIGN PATENT DOCUMENTS

| CA | 2 386 147 A1 | 4/2001 |
|---|---|---|
| CA | 2 439 758 | 9/2002 |
| DE | 1913471 | 11/1969 |
| EP | 0 200 024 A2 | 11/1986 |
| EP | 0 200 024 B1 | 11/1986 |
| GB | 1341375 | 12/1973 |
| JP | 44029656 | 12/1969 |
| JP | 61-254563 | 11/1986 |
| JP | 2003-511371 A | 3/2003 |
| JP | 2004-262890 A | 9/2004 |
| JP | 2004-526722 A | 9/2004 |
| JP | 2004262890 | 9/2004 |
| JP | 20040269469 | 9/2004 |
| WO | WO9825920 | 6/1998 |
| WO | WO 99/47153 | 9/1999 |
| WO | WO 00/03746 | 1/2000 |
| WO | WO0174823 A2 | 10/2001 |
| WO | 02/06237 A1 | 1/2002 |
| WO | WO 02/064146 A1 | 8/2002 |
| WO | WO 02/064545 | 8/2002 |
| WO | WO 02/064546 A2 | 8/2002 |

(Continued)

OTHER PUBLICATIONS

Hagen, V. et al., "Potentielle Kardiotonika: 8. Mitteilung5: 2-Acyloxyalkylamino-, 2-Acyloxyalkoxy- und 2-Acylaminoalkylamino-3-cyan-5-(pyrid-4-yl)pyridine," Pharmazie (1990), vol. 45, pp. 343-345.

Kotha, Sambasivarao et al., "Recent applications of the Suzuki-Miyaura cross-coupling reaction in organic synthesis," Tetrahedron (2002), vol. 58, pp. 9633-9695.

Meijere, Armin de et al., "Fine Feathers Make Fine Birds: The Heck Reaction in Modern Garb," Angewandte Chemie International Edition (1994), vol. 33, pp. 2379-2411.

(Continued)

*Primary Examiner* — Patricia L Morris

(74) *Attorney, Agent, or Firm* — Scully, Scott, Murphy & Presser, P.C.

(57) ABSTRACT

The present invention relates to N-alkylamides of the formula I,

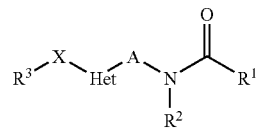

in which A, Het, X, $R^1$, $R^2$ and $R^3$ have the meanings indicated in the claims, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

9 Claims, No Drawings

(56) References Cited

FOREIGN PATENT DOCUMENTS

| WO | WO 02/064565 A1 | 8/2002 |
| --- | --- | --- |
| WO | WO 02/070520 A1 | 9/2002 |
| WO | 03/022821 A1 | 3/2003 |
| WO | 03/082191 A2 | 10/2003 |
| WO | WO 03/094845 A2 | 11/2003 |
| WO | WO 2004/014369 A1 | 2/2004 |
| WO | WO 2004/014372 A1 | 2/2004 |
| WO | WO 2004/014842 A1 | 2/2004 |
| WO | WO 2004/060890 A1 | 7/2004 |
| WO | WO2004056807 | 7/2004 |
| WO | WO 2004/089903 A1 | 10/2004 |
| WO | WO 2004/094425 A1 | 11/2004 |
| WO | 2005/068444 A2 | 7/2005 |
| WO | WO2005075465 | 8/2005 |

OTHER PUBLICATIONS

Endres, Matthias et al., "Stroke protection by 3-hydroxy-3-nnethylglutaryl (HMG)-CoA reductase inhibitors mediated by endothelial nitric oxide synthase," Proceedings of the National Academy of Sciences (1998), vol. 95, pp. 8880-8885.

Li, Huige et al., "Activation of Protein Kinase Ca and/or Enhances Transcription of the Human Endothelial Nitric Oxide Synthase Gene," Molecular Pharmacology (1998), vol. 53, pp. 630-637.

Mitsunobu, Oyo, "The Use of Diethyl Azodicarboxylate and Triphenylphosphine in Synthesis and Transformation of Natural Products," Synthesis (1981), pp. 1-28.

Miyaura, Norio, "Organoboron Compounds," Topics in Current Chemistry (2002), vol. 219, pp. 11-59.

Moroi, Masao et al., "Interaction of Genetic Deficiency of Endothelial Nitric Oxide, Gender, and Pregnancy in Vascular Response to Injury in Mice," The Journal of Clinical Investigation (1998), vol. 101, No. 6, pp. 1225-1232.

Nakayama, Masafumi et al., "T786→C Mutation in the 5'-Flanking Region of the Endothelial Nitric Oxide Synthase Gene Is Associated With Coronary Spasm," Circulation (1999), vol. 99, pp. 2864-2870.

Sessa, William C. et al., "Chronic Exercise in Dogs Increases Coronary Vascular Nitric Oxide Production and Endothelial Cell Nitric Oxide Synthase Gene Expression," Circulation Research (1994), vol. 74, pp. 349-353.

Tilley, Jefferson W. et al., "A Convenient Palladium-Catalyzed Coupling Approach to 2,5-Disubstituted Pyridines," The Journal of Organic Chemistry (1988), vol. 53, pp. 386-390.

Varenne, Olivier et al., "Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries," Human Gene Therapy (2000), vol. 11, pp. 1329-1339.

Walker, Shawn D. et al., "A Rationally Designed Universal Catalyst for Suzuki-Miyaura Coupling Processes," Angewandte Chemie International Edition (2004), vol. 43, pp. 1871-1876.

CAS, Interchim Intermediates, Database Chemcats—Chem Abstracts—XP002361676; Jan. 18, 2005; pp. 1-3.

Lipinski, et al., Bioisosteric prototype design of biaryl imidazolyl and triazolyl competetive histamine H-2-receptor antagonists, J. of Med. Chem. 29(11); 1986, pp. 2154-2163.

El-Zohry, et al., "Synthesis of Some New 3-(2'-Heterocyclicethyl)-2-methyl-3,4-dihydroquinazolin-4-one Derivatives as Antimicrobial Agents", J. Chem. Tech. Biotechnol, 1992, 55 pp. 209-215.

Liu, et al., "Novel Isoxazole Carboxamides as Growth Hormone Secretagogue Receptor (GHS-R) antagonists", Biorganic & Medicinal Chemistry Letters 14 (2004) 5223-5226.

Raiman, et al., "A Convenient Approach to the Synthesis of 2-(2-aminoethyl) Pyrroles and their Heterocyclization into Hydrogenated Pyrrolopyridines and related Pyrroloindolizines", Tetrahedron 59 (2003) 5265-5272.

Seydel, et al.,Structure-activity-Beziungen at 5-substituted 2-(Nitrofuryl) pyrimidines, Eur. J. Med. Chem. 10 (1975) p. 378-386, together with English language summary on last page.

Tanis, et al., "Furan-Terminated N-Acyliminium Ion Initiated Cyclizations in Alkaloid Synthesis", J.Org. Chem. 63 (1998), p. 6914-1628.

HETEROARYL-SUBSTITUTED AMIDES COMPRISING A SATURATED LINKER GROUP, AND THEIR USE AS PHARMACEUTICALS

This application is a Continuation of International Application No. PCT/EP2006/005706, filed Jun. 14, 2006.

FIELD OF THE INVENTION

The present invention relates to N-alkylamides of the formula I,

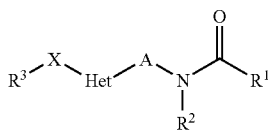

in which A, Het, X, $R^1$, $R^2$ and $R^3$ have the meanings indicated below, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

BACKGROUND OF THE INVENTION

Endothelial NO synthase (eNOS, NOS-III) belongs to a group of three isoenzymes which produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain amide derivatives which upregulate the expression of endothelial NO synthase, in particular N-cycloalkyl amides in which the cycloalkyl ring is fused to a benzene ring or a heteroaromatic ring, have been described in WO 02/064146, WO 02/064545, WO 02/064546, WO 02/064565, WO 2004/014369, WO 2004/014372 and WO 2004/014842. Certain triaza- and tetraazaanthracenedione derivatives which upregulate the expression of endothelial NO synthase have been described in WO 2004/094425. There still exists a need for further compounds which upregulate the expression of endothelial NO synthase and have a favorable property profile and are useful as pharmaceuticals for the treatment of various diseases such as atherosclerosis, coronary artery disease or cardiac insufficiency, for example. Surprisingly it has now been found that the compounds of the formula I are modulators of the transcription of endothelial NO synthase and in particular stimulate, or upregulate, the expression of eNOS, and are useful for the treatment of various diseases such as the mentioned cardiovascular disorders.

Certain compounds which are encompassed by the formula I have already been described. In JP 2004-262890 compounds are described which inhibit the synthesis of 20-hydroxyeicosatetraenoic acid (=20-HETE) from arachidonic acid and which contain a substituted central benzene ring or pyridine ring. The central ring carries a heterocyclic group, which in the case of a central pyridine ring is present in the 5-position, and a further group of broad structural variety, which in the case of a central pyridine ring is present in the 2-position. Said further group can, among others, be an unsubstituted imidazolin-2-on-1-yl group, which is assumed to mean a 2-oxoimidazolin-1-yl group, or an unsubstituted 2-oxopyrrolidin-1-yl group which are linked to the central ring via an alkyloxy group. Compounds of the formula I, in which $R^1$ and $R^2$ together with the N—CO group which carries them form a group of the formula

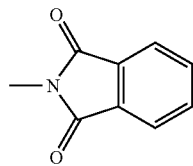

i.e. compounds in which the group —N($R^2$)—CO—$R^1$ is a phthalimido group which group is also designated as 1,3-dioxoisoindol-2-yl group or 1,3-dioxo-1,3-dihydroisoindol-2-yl group or 1,3-dioxo-2,3-dihydro-1H-isoindol-2-yl group, are described in a number of documents including DE 1913471, GB 1341375, U.S. Pat. No. 5,190,589, U.S. Pat. No. 5,547,972 and Lipinski et al., J. Med. Chem. 29 (1986) 2154. Such phthalimido compounds commonly are intermediates in the synthesis of the respective compounds containing an amino group —$NH_2$ using the Gabriel reaction, or are protected forms of such amino compounds.

In other documents certain compounds comprised by the formula I are described in which $R^1$ and $R^2$, together with the N—CO group which carries them, do not form a ring. For example, In U.S. Pat. No. 5,292,732 1-(2-acylaminoethyl) pyrroles are described which are intermediates in the synthesis of monoamine oxidase inhibiting pyrrolopyrazines. In JP 44-29656 4-(ω-acylaminoalkyl)isoxazoles are described which exhibit analgesic, antitussive, antipyretic and antiinflammatory activity. In U.S. Pat. No. 3,655,684 3-(2-acylaminoethyl)-5-phenyl-1,2,4-oxadiazoles are described which exhibit anticonvulsant activity. Certain 3-cyanopyridines which carry an oxaalkylamino, aminoalkylamino, oxaalkyloxy, acyloxyalkylamino, acylaminoalkylamino or acyloxyalkyloxy group in the 2-position and a pyridin-4-yl group or an alkyloxy-substituted phenyl group in the 5-position and which exhibit cardiotonic activity, including the specific compounds of the formula I in which A is the group NH—$CH_2$—$CH_2$ the nitrogen atom of which is attached to the group Het, Het is a pyridinyl group whose 2-position carries the group A and which is substituted by cyano in the 3-position, X is a direct bond, $R^3$ is pyridin-4-yl which is attached to the 5-position of the pyridinyl group representing Het, $R^2$ is hydrogen and $R^1$ is either methyl or ethyl or pyridin-3-yl, are described in Hagen et al., Pharmazie 45 (1990) 343 and EP 200024. A stimulating effect of these known compounds of the formula I on the transcription or the expression of eNOS and their use in the treatment of diseases which is based on such effect, has not yet been described.

SUMMARY OF THE INVENTION

A subject of the present invention is a compound of the formula I,

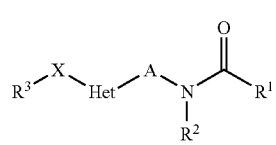

in which
A is chosen from —$CH_2$—$CH_2$—, —$CH_2$—$CH_2$—$CH_2$— and —Y—$CH_2$—$CH_2$—, wherein all $CH_2$ groups can be substituted by one or more identical or different substituents $R^4$, and wherein Y is chosen from O, S and $NR^{11}$ and Y is bonded to the group Het;

Het is a 5-membered or 6-membered, monocyclic aromatic group which contains one or two identical or different hetero ring members chosen from N, $NR^{13}$, O and S and which can be substituted by one or more identical or different substituents $R^5$;

X is chosen from a direct bond, $CH_2$, O and NH;

$R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$;

$R^3$ is chosen from phenyl, naphthalenyl and heteroaryl which can all be substituted by one or more identical or different substituents chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_2$)-alkylenedioxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, COOH, $CONH_2$, CN, $CF_3$, $H_2NSO_2$— and ($C_1$-$C_4$)-alkyl-$SO_2$—;

$R^4$ is chosen from ($C_1$-$C_4$)-alkyl and fluorine;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, COOH, $CONH_2$, CN, $CF_3$ and ($C_1$-$C_4$)-alkyl-$SO_2$—;

$R^8$ is chosen from halogen, ($C_1$-$C_4$)-alkyl, ($C_3$-$C_7$)-cycloalkyl-$C_nH_{2n}$—, phenyl-$C_nH_{2n}$—, heteroaryl-$C_nH_{2n}$—, ($C_1$-$C_4$)-alkyloxy-($C_1$-$C_2$)-alkyl-, OH, oxo, ($C_1$-$C_4$)-alkyloxy which can be substituted by one or more fluorine atoms, ($C_1$-$C_2$)-alkylenedioxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, COOH, $CONH_2$, CN, $CF_3$, $H_2NSO_2$— and ($C_1$-$C_4$)-alkyl-$SO_2$—, wherein all phenyl groups and heteroaryl groups can independently of each other be substituted by one or more identical or different substituents chosen from halogen, ($C_1$-$C_4$)-alkyl, $CF_3$ and ($C_1$-$C_4$)-alkyloxy;

$R^{11}$ is chosen from hydrogen, ($C_1$-$C_4$)-alkyl and (($C_1$-$C_4$)-alkyl)-CO—;

$R^{12}$ is chosen from hydrogen, ($C_1$-$C_4$)-alkyl, ($C_3$-$C_7$)-cycloalkyl-$C_nH_{2n}$—, phenyl-$C_nH_{2n}$—, heteroaryl-$C_nH_{2n}$—, (($C_1$-$C_4$)-alkyl)-CO—, ($C_3$-$C_7$)-cycloalkyl-$C_nH_{2n}$—CO—, phenyl-$C_nH_{2n}$—CO—, heteroaryl-$C_nH_{2n}$—CO—, (($C_1$-$C_4$)-alkyl)-O—CO— and phenyl-$C_nH_{2n}$—O—CO—, wherein all phenyl groups and heteroaryl groups can be substituted by one or more identical or different substituents chosen from halogen, ($C_1$-$C_4$)-alkyl, $CF_3$ and ($C_1$-$C_4$)-alkyloxy;

$R^{13}$ is chosen from hydrogen, ($C_1$-$C_4$)-alkyl and phenyl-$C_nH_{2n}$—, wherein the phenyl group can be substituted by one or more identical or different substituents chosen from halogen, ($C_1$-$C_4$)-alkyl, $CF_3$ and ($C_1$-$C_4$)-alkyloxy, where all groups $R^{13}$ are independent of each other and can be identical or different;

heteroaryl is a 5-membered or 6-membered, monocyclic aromatic group which contains one, two or three identical or different hetero ring members chosen from N, $NR^{13}$, O and S;

n is 0, 1 or 2, where all numbers n are independent of each other and can be identical or different;

in any of its stereoisomeric forms or a mixture of stereoisomeric forms in any ratio, or a physiologically acceptable salt thereof;

provided that the group —N($R^2$)—CO—$R^1$ cannot be an unsubstituted 2-oxopyrrolidin-1-yl group or an unsubstituted 2-oxoimidazolin-1-yl group if simultaneously the group $R^3$—X-Het- is a group of the formula

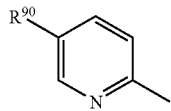

in which the bond via which the group is connected to the group A is depicted by the line starting in the 2-position of the pyridine ring, and in which $R^{90}$ is chosen from imidazol-1-yl, isoxazol-5-yl, isothiazol-5-yl, 1,2,4-triazol-1-yl, pyrazin-2-yl and pyrazol-3-yl which can all be substituted by ($C_1$-$C_4$)-alkyl, and which can be substituted in the pyridine ring by up to four substituents chosen from ($C_1$-$C_4$)-alkyl, ($C_1$-$C_4$)-alkyloxy and halogen;

and provided that the group —N($R^2$)—CO—$R^1$ cannot be a 1,3-dioxoisoindol-2-yl group of the formula

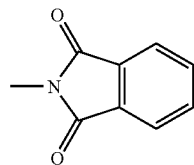

in which the bond via which the group is connected to the group A is depicted by the line starting at the nitrogen atom.

Another subject of the present invention is the use of a compound of the formula Ia

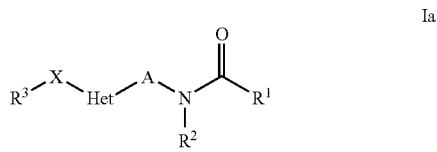

in which

A is chosen from —$CH_2$—$CH_2$—, —$CH_2$—$CH_2$—$CH_2$— and —Y—$CH_2$—$CH_2$— wherein all $CH_2$ groups can be substituted by one or more identical or different substituents $R^4$, and wherein Y is chosen from O, S and $NR^{11}$ and Y is bonded to the group Het;

Het is 5-membered to 10-membered, monocyclic or bicyclic, aromatic group which contains one or more identical or different hetero ring members chosen from N, $NR^{13}$, O and S and which can be substituted by one or more identical or different substituents $R^5$;

X is chosen from a direct bond, $CH_2$, O, S, NH and N(($C_1$-$C_4$)-alkyl), or X is absent and in this case the phenyl, naphthalenyl or heteroaryl group representing the group $R^3$ is fused to the group Het;

$R^1$ and $R^2$ are independently of each other chosen from ($C_1$-$C_{10}$)-alkyl, ($C_3$-$C_{10}$)-alkenyl, ($C_3$-$C_{10}$)-alkynyl, ($C_3$-$C_{10}$)-cycloalkyl-$C_nH_{2n}$—, phenyl-$C_nH_{2n}$—, naphthalenyl-$C_nH_{2n}$— and heteroaryl-$C_nH_{2n}$—, and $R^2$ can in addition be hydrogen, wherein the groups ($C_1$-$C_{10}$)-alkyl, ($C_3$-$C_{10}$)-cycloalkyl, ($C_3$-$C_{10}$)-alkenyl and ($C_3$-$C_{10}$)-alkynyl can all be substituted by one or more identical or different substituents $R^6$, and the groups $C_nH_{2n}$ can all be substituted by one or more identical or different substituents chosen from fluorine and ($C_1$-$C_4$)-alkyl, and all phenyl, naphthalenyl and heteroaryl groups can independently of each other be substituted by one or more identical or different substituents $R^7$, or $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$;

$R^3$ is chosen from phenyl, naphthalenyl and heteroaryl which can all be substituted by one or more identical or different substituents chosen from halogen, ($C_1$-$C_6$)-alkyl, ($C_1$-$C_6$)-alkyloxy-($C_1$-$C_6$)-alkyl-, OH, ($C_1$-$C_6$)-alkyloxy which can be substituted by one or more fluorine atoms, ($C_1$-$C_3$)-alkylenedioxy which can be substituted by one or more fluorine atoms, ($C_1$-$C_6$)-alkylmercapto, $NH_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-$SO_2NH$—, di(($C_1$-$C_6$)-alkyl)aminocarbonyl-, (($C_1$-$C_6$)-alkyl)aminocarbonyl-, (($C_1$-$C_6$)-alkyloxy)carbonyl-, COOH, $CONH_2$, CN, $CF_3$, (($C_1$-$C_6$)-alkyl)$NHSO_2$—, di(($C_1$-$C_6$)-alkyl)$NSO_2$—, $H_2NSO_2$— and ($C_1$-$C_6$)-alkyl-$SO_2$—;

$R^4$ is chosen from ($C_1$-$C_6$)-alkyl, fluorine and oxo;

$R^5$ is chosen from halogen, ($C_1$-$C_6$)-alkyl, phenyl-$C_nH_{2n}$—, ($C_1$-$C_6$)-alkyloxy-($C_1$-$C_3$)-alkyl-, OH, ($C_1$-$C_6$)- alkyloxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, di$((C_1-C_6)$-alkyl)aminocarbonyl-, $((C_1-C_6)$-alkyl)aminocarbonyl-, $((C_1-C_6)$-alkyloxy)carbonyl-, COOH, $CONH_2$, CN, $CF_3$, $H_2NSO_2$—, $((C_1-C_6)$-alkyl)NHSO_2$—, di$((C_1-C_6)$-alkyl)$NSO_2$— and $(C_1-C_6)$-alkyl-$SO_2$—, wherein the phenyl group can be substituted by one or more identical or different substituents chosen from halogen, $(C_1-C_4)$-alkyl, $CF_3$ and $(C_1-C_4)$-alkyloxy;

$R^6$ is chosen from fluorine, OH, oxo, $(C_1-C_6)$-alkyloxy, $(C_1-C_6)$-alkylmercapto, di$((C_1-C_6)$-alkyl)amino, $((C_1-C_6)$-alkyl)-CONH—, di$((C_1-C_6)$-alkyl)aminocarbonyl-, $((C_1-C_6)$-alkyloxy)carbonyl-, COOH, $CONH_2$, CN and $CF_3$;

$R^7$ is chosen from halogen, $(C_1-C_6)$-alkyl, $(C_1-C_6)$-alkyloxy-$(C_1-C_3)$-alkyl-, OH, $(C_1-C_6)$-alkyloxy which can be substituted by one or more fluorine atoms, $(C_1-C_3)$-alkylenedioxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, di$((C_1-C_6)$-alkyl)aminocarbonyl-, $((C_1-C_6)$-alkyl)aminocarbonyl-, $((C_1-C_6)$-alkyloxy)carbonyl-, COOH, $CONH_2$, CN, $CF_3$, $SF_5$, $H_2NSO_2$—, $((C_1-C_6)$-alkyl)NHSO_2$—, di$((C_1-C_6)$-alkyl)$NSO_2$— and $(C_1-C_6)$-alkyl-$SO_2$—;

$R^8$ is chosen from halogen, $(C_1-C_6)$-alkyl, $(C_3-C_7)$-cycloalkyl-$C_nH_{2n}$—, phenyl-$C_nH_{2n}$—, heteroaryl-$C_nH_{2n}$—, $(C_1-C_6)$-alkyloxy-$(C_1-C_3)$-alkyl-, OH, oxo, $(C_1-C_6)$-alkyloxy which can be substituted by one or more fluorine atoms, $(C_1-C_3)$-alkylenedioxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, di$((C_1-C_6)$-alkyl)aminocarbonyl-, $((C_1-C_6)$-alkyl)aminocarbonyl-, $((C_1-C_6)$-alkyloxy)carbonyl-, COOH, $CONH_2$, CN, $CF_3$, $SF_5$, $H_2NSO_2$— and $(C_1-C_6)$-alkyl-$SO_2$—, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy;

$R^{11}$ is chosen from hydrogen, $(C_1-C_6)$-alkyl, $(C_3-C_7)$-cycloalkyl-$C_nH_{2n}$—, phenyl-$C_nH_{2n}$—, heteroaryl-$C_nH_{2n}$—, $((C_1-C_6)$-alkyl)-CO—, $(C_3-C_7)$-cycloalkyl-$C_nH_{2n}$—CO—, phenyl-$C_nH_{2n}$—CO— and heteroaryl-$C_nH_{2n}$—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy;

$R^{12}$ is chosen from hydrogen, $(C_1-C_6)$-alkyl, $(C_3-C_7)$-cycloalkyl-$C_nH_{2n}$—, phenyl-$C_nH_{2n}$—, heteroaryl-$C_nH_{2n}$—, $((C_1-C_6)$-alkyl)-CO—, $(C_3-C_7)$-cycloalkyl-$C_nH_{2n}$—CO—, phenyl-$C_nH_{2n}$—CO—, heteroaryl-$C_nH_{2n}$—CO—, $((C_1-C_6)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy;

$R^{13}$ is chosen from hydrogen, $(C_1-C_4)$-alkyl and phenyl-$C_nH_{2n}$—, wherein the phenyl group can be substituted by one or more identical or different substituents chosen from halogen, $(C_1-C_4)$-alkyl, $CF_3$ and $(C_1-C_4)$-alkyloxy, where all groups $R^{13}$ are independent of each other and can be identical or different;

heteroaryl is a 5-membered to 10-membered, monocyclic or bicyclic aromatic group which contains one or more identical or different hetero ring members chosen from N, $NR^{13}$, O and S;

n is 0, 1, 2 or 3, where all numbers n are independent of each other and can be identical or different;

in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other disease mentioned above or below herein.

DETAILED DESCRIPTION OF THE INVENTION

If in the compounds of the formulae I and Ia any groups, substituents, hetero ring members, numbers or other features such as, for example, $R^4$, $R^5$, $R^6$, $R^7$, $R^8$, $R^{12}$, $R^{13}$, alkyl groups, the number n, etc. can occur several times, they can all independently of one another have any of the indicated meanings and can in each case be identical or different from one another. In a dialkylamino group, for example, the alkyl groups can be identical or different.

Alkyl, alkenyl and alkynyl groups can be linear, i.e. straight-chain, or branched. This also applies when they are part of other groups, for example alkyloxy groups (=alkoxy groups, i.e. alkyl-O— groups), alkyloxycarbonyl groups or alkyl-substituted amino groups, or when they are substituted. Substituted alkyl, alkenyl and alkynyl groups can be substituted by one or more, for example one, two, three, four or five, identical or different substituents which can be located in any desired positions. Examples of alkyl groups are methyl, ethyl, propyl, butyl, pentyl, hexyl, heptyl, octyl, nonyl, decyl, the n-isomers of these groups, isopropyl, isobutyl, isopentyl, sec-butyl, tert-butyl, neopentyl or 3,3-dimethylbutyl. Alkenyl groups and alkynyl groups preferably contain one double bond or triple bond, respectively, which can be present in any desired position of the group. Examples of alkenyl and alkynyl are prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, dec-3-enyl, dec-9-enyl, prop-2-ynyl (=propargyl), but-2-ynyl, but-3-ynyl, hex-4-ynyl or hex-5-ynyl.

As far as applicable, the preceding explanations regarding alkyl groups apply correspondingly to divalent alkyl groups, i.e. alkanediyl groups and alkylene groups, such as the methylene group —$CH_2$— and the polymethylene groups —$CH_2$—$CH_2$— and —$CH_2$—$CH_2$—$CH_2$— occurring in the group A and in divalent alkylenedioxy groups such as —O—$CH_2$—O—, —O—$CH_2$—$CH_2$—O— or —O—$CH_2$—$CH_2$—$CH_2$—O—, and the groups $C_nH_{2n}$, which can also be linear or branched and/or can be substituted by one or more, for example one, two, three, four or five, identical or different substituents which can be located in any desired positions. Of course, the number of substituents can in general not exceed the number of hydrogen atoms in the unsubstituted parent system which can be replaced with a substituent, and can, for example, be only one or two in the case of a $CH_2$ group. Examples of the group $C_nH_{2n}$, in which the number n is 1, 2, or 3, are —$CH_2$—, —$CH_2$—$CH_2$—, —$CH_2$—$CH_2$—$CH_2$—, —CH($CH_3$)—, —C($CH_3$)_2—, —CH($CH_3$)—$CH_2$—, —$CH_2$—CH($CH_3$)—. If the number n in the group $C_nH_{2n}$ is 0 (=zero), the two groups which are attached to the group $C_nH_{2n}$ are directly connected to one another via a single bond. Similarly, if the group X is a direct bond, the groups $R^3$ and Het are directly connected to one another via a single bond.

Examples of cycloalkyl groups are cyclopropyl, cyclobutyl, cyclopentyl, cyclohexyl, cycloheptyl, cyclooctyl, cyclononyl and cyclodecyl. Substituted cycloalkyl groups can be substituted by one or more, for example one, two, three, four or five, identical or different substituents which can be located in any desired positions. In general, besides any other specified substituents, all cycloalkyl groups can also carry one or more, for example one, two, three, four or five, identical or different ($C_1$-$C_4$)-alkyl substituents, for example methyl substituents, which can be located in any desired positions. Examples of alkyl-substituted cycloalkyl groups are 4-methylcyclohexyl, 4-tert-butylcyclohexyl or 2,3-dimethylcyclopentyl.

If a group like phenyl, naphthalenyl and heteroaryl, which can be unsubstituted or substituted, is substituted by one or more substituents, in general it can carry one, two, three, four or five identical or different substituents, for example. The substituents can be located in any desired positions. Substituted heteroaryl groups can be substituted on ring carbon atoms and/or on suitable ring nitrogen atoms, i.e. ring nitrogen atoms which in the parent ring system carry a hydrogen atom, where preferred substituents on such substituted ring nitrogen atoms are alkyl groups, for example ($C_1$-$C_4$)-alkyl groups, unless stated otherwise. Suitable ring nitrogen atoms, such as the ring nitrogen atoms in a pyridine ring or a quinoline ring, can also be present as N-oxides or as quaternary salts, the latter preferably having a counter-anion which is derived from a physiologically acceptable acid. In monosubstituted phenyl groups the substituent can be located in the 2-position, the 3-position or the 4-position. In a disubstituted phenyl group the substituents can be located in 2,3-position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4,6-position or 3,4,5-position. Naphthalenyl (=naphthyl) can be naphthalen-1-yl or naphthalen-2-yl. In monosubstituted naphthalen-1-yl groups the substituent can be located in the 2-, 3-, 4-, 5-, 6-, 7-, or 8-position, in monosubstituted naphthalen-2-yl groups the substituent can be located in the 1-, 3-, 4-, 5-, 6-, 7-, or 8-position. In disubstituted naphthalenyl groups the substituents can likewise occur in any desired positions in the ring via which the naphthalenyl group is bonded, and/or in the other ring.

Heteroaryl groups are preferably 5-membered or 6-membered monocyclic aromatic heterocyclic groups or 9-membered or 10-membered bicyclic aromatic heterocyclic groups, where the bicyclic groups contain a 6-membered ring fused to a 5-membered or two fused 6-membered rings. In bicyclic heteroaryl groups one or both rings can be aromatic and one or both rings can contain hetero ring members. Preferably heteroaryl groups and other heterocyclic groups contain one, two or three, for example one or two, identical or different hetero ring members. The hetero ring members or ring heteroatoms in heteroaryl groups and other heterocyclic groups are generally chosen from N, O and S wherein N includes ring nitrogen atoms which carry a hydrogen atom or any substituent as is the case in 5-membered aromatic heterocycles such as pyrrole, pyrazole or imidazole, for example. The hetero ring members in heteroaryl groups and other heterocyclic groups can be located in any desired positions provided that the resulting heterocyclic system is known in the art and is stable and suitable as a subgroup in a drug substance. For example, in general two atoms from the series O and S cannot be present in adjacent ring positions. Examples of parent heterocycles of heteroaryl groups and other heterocyclic groups are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, 1,2,3-triazine, 1,2,4-triazine, 1,3,5-triazine, 1,2,4,5-tetrazine, indole, benzothiophene, benzofuran, 1,3-benzodioxole (=1,2-methylenedioxybenzene), 1,3-benzoxazole, 1,3-benzothiazole, benzoimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, acridine or pteridine. Heteroaryl groups, including heteroaryl groups representing $R^3$, and other heterocyclic groups can be bonded via any desired suitable ring carbon atom and, in the case of nitrogen heterocycles, ring nitrogen atom. Preferably they are bonded via a ring carbon atom. For example, thiophenyl (=thienyl) can be thiophen-2-yl or thiophen-3-yl, pyridinyl (=pyridyl) can be pyridin-2-yl, pyridin-3-yl or pyridin-4-yl, imidazolyl can be, for example, 1H-imidazol-1-yl, 1H-imidazol-2-yl, 1H-imidazol-4-yl or 1H-imidazol-5-yl, quinolinyl (=quinolyl) can be quinolin-2-yl, quinolin-3-yl, quinolin-4-yl, quinolin-5-yl, quinolin-6-yl, quinolin-7-yl or quinolin-8-yl. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

As far as applicable, the preceding explanations regarding heteroaryl groups apply correspondingly to divalent heteroaryl groups, i.e. heteroarylene groups, such as the group Het in formulae I and Ia. In general, a divalent heteroaryl group can be bonded to the adjacent groups via any two desired suitable ring atoms including ring carbon atoms and/or, in the case of nitrogen heterocycles, ring nitrogen atoms. Preferably they are bonded via any two ring carbon atoms, in particular in the case of the group Het. In the case of a divalent bicyclic heteroaryl group the positions via which it is bonded to the adjacent groups can be located in the same ring or in different rings. In the case of a divalent group derived from furan or thiophene, for example, the adjacent groups can be bonded in 2,3-position, 2,4-position, 2,5-position or 3,4-position. A divalent group derived from 1,3-thiazole can be 1,3-thiazole-2,4-diyl, 1,3-thiazole-2,5-diyl or 1,3-thiazole-4,5-diyl. A divalent group derived from pyridine can be pyridine-2,3-diyl, pyridine-2,4-diyl, pyridine-2,5-diyl, pyridine-2,6-diyl, pyridine-3,4-diyl or pyridine-3,5-diyl. In the case of an unsymmetrical divalent group the present invention includes all positional isomers, i.e., in the case of a pyridine-2,5-diyl group, for example, it includes the compound in which the one adjacent group is present in the 2-position and the other adjacent group is present in the 5-position as well as the compound in which the one adjacent group is present in the 5-position and the other adjacent group is present in the 2-position. Depending on the ranking order of the adjacent groups in the nomenclature of the compound, in the name of a compound the numbers of the locations of the adjacent groups may differ from the ones indicated above and, for example, a pyridine-2,5-diyl group may be designated as a pyridine-3,6-diyl group.

As far as applicable, the above explanations also apply correspondingly to the aromatic heterocycle which is formed by fusion of the group $R^3$ to the group Het in case the group X is absent. In the respective compounds of the formula Ia the resulting polycyclic heteroaromatic group, which represents the $R^3$—X-Het-moiety in formula Ia which moiety may also be designated as $R^3$—X'-Het-moiety to distinguish it from the $R^3$—X-Het-moiety in the compounds of the formula I, is a bicyclic or tricyclic or tetracyclic ring system, preferably a bicyclic or tricyclic ring system, more preferably a bicyclic ring system, and contains one or more, for example one, two, three or four, identical or different hetero ring members chosen from N, $NR^{13}$, O and S. A phenyl or naphthalenyl or heteroaryl group representing $R^3$ can be fused to, or condensed to, the group Het via any suitable bond in $R^3$ and any suitable bond in the group Het, provided that the resulting polycyclic heteroaromatic group is known in the art to be stable and suitable as a subgroup in a drug substance and that in the resulting group at least the ring bonded to the group A can be an aromatic ring, i.e. contain six conjugated pi electrons in case of a 5-membered or 6-membered monocyclic ring. For example, if the group Het in a compound of the formula Ia is a pyridine ring, X is absent and $R^3$ is phenyl, the latter carbocyclic ring can be fused to the bond between positions 2 and 3 or the bond between positions 3 and 4 in the pyridine ring, and the resulting polycyclic heteroaromatic group representing the $R^3$—X-Het-moiety is a quinolinyl or isoquinolinyl group. If a naphthalenyl group representing $R^3$ is fused to a pyridine ring representing Het, the resulting polycyclic heteroaromatic group representing the $R^3$—X-Het-moiety is an aza-anthracenyl or aza-phenanthrenyl group. The polycyclic heteroaromatic which is present in case X is absent, can be bonded to the group A via any suitable ring atom, preferably a ring carbon atom, in an aromatic ring originating from the group Het, and can be substituted by substituents as outlined above for the individual groups $R^3$ and Het.

The heterocyclic ring which can be formed by $R^1$ and $R^2$ together with the N—CO group depicted in formulae I and Ia which carries $R^1$ and $R^2$, which ring is a lactam ring, can be 4-membered, 5-membered, 6-membered, 7-membered, 8-membered, 9-membered or 10-membered, and can be saturated, i.e. contain no double bond within the ring, or unsaturated, including partially unsaturated and aromatic, in particular partially unsaturated, and contain, for example, one, two, three or four double bonds within the ring, provided the respective ring system is known in the art to be stable and suitable as a subgroup in a drug substance. Examples of residues of heterocyclic rings formed by $R^1$ and $R^2$ together with the N—CO group, which residues are bonded to the group A via the nitrogen atom in the said N—CO group depicted in formulae I and Ia, are 2-oxo-azetidin-1-yl, 2-oxo-pyrrolidin-1-yl, 2-oxo-2,5-dihydro-1H-pyrrol-1-yl, 2-oxo-piperidin-1-yl, 2-oxo-1,2,3,4-tetrahydropyridin-1-yl, 2-oxo-1,2,5,6-tetrahydropyridin-1-yl, 2-oxo-1,2-dihydropyridin-1-yl, 2-oxo-azepan-1-yl, 2-oxo-azocan-1-yl, 2-oxo-azecan-1-yl, 2-oxo-octahydrocyclopenta[b]pyrrol-1-yl, 2-oxo-2,3-dihydro-1H-indol-1-yl, 2-oxo-octahydro-1H-indol-1-yl, 1-oxo-2,3-dihydro-1H-isoindol-2-yl, 1-oxo-octahydro-1H-isoindol-2-yl, 2-oxo-1,2-dihydroquinolin-1-yl, 2-oxo-1,2,3,4-tetrahydroquinolin-1-yl, 2-oxo-decahydroquinolin-1-yl, 1-oxo-1,2-dihydroisoquinolin-2-yl, 3-oxo-1,2,3,4-tetrahydroisoquinolin-2-yl, 1-oxo-1,2,3,4-tetrahydroisoquinolin-2-yl, 1-oxo-decahydroisoquinolin-2-yl, 3-oxo-decahydroisoquinolin-2-yl, 4-oxo-4,5,6,7-tetrahydrothieno[3,2-c]pyridin-5-yl, 6-oxo-4,5,6,7-tetrahydrothieno[3,2-c]pyridin-5-yl, 3-oxo-pyrazolidin-2-yl, 2-oxo-imidazolidin-1-yl, 5-oxo-imidazolidin-1-yl, 2-oxo-hexahydropyrimidin-1-yl, 6-oxo-hexahydropyrimidin-1-yl, 2-oxo-1,2-dihydropyrimidin-1-yl, 2-oxo-piperazin-1-yl, 2-oxo-[1,3]diazepan-1-yl, 7-oxo-[1,3]diazepan-1-yl, 2-oxo-[1,4]diazepan-1-yl, 7-oxo-[1,4]diazepan-1-yl, 2-oxo-oxazolidin-3-yl, 2-oxo-[1,3]oxazinan-3-yl, 2-oxo-[1,3]oxazepan-3-yl, 3-oxo-morpholin-4-yl, 3-oxo-[1,4]oxazepan-4-yl, 5-oxo-[1,4]oxazepan-4-yl, 2-oxo-thiazolidin-3-yl, 2-oxo-[1,3]thiazinan-3-yl, 3-oxo-thiomorpholin-4-yl, 3-oxo-3,4-dihydro-2H-[1,4]thiazin-4-yl, 2-oxo-[1,3]thiazepan-3-yl, 3-oxo-[1,4]thiazepan-4-yl, 5-oxo-[1,4]thiazepan-4-yl. As applies to the ring which can be formed by $R^1$ and $R^2$ together with the N—CO group in general, all listed examples of heterocyclic groups can be unsubstituted or substituted as indicated above, for example by $R^8$. For example, they can be substituted on one or more, for example one, two or three, preferably one or two, more preferably one, ring carbon atoms by further oxo groups in addition to the oxo group mentioned in the listed names, and/or by one or more, for example one, two, three or four, preferably one or two, identical or different alkyl groups such as methyl groups, and/or on one or more ring nitrogen atoms by a $(C_1-C_4)$-alkyl group or a $(C_1-C_4)$-alkyl-CO— group such as methyl or acetyl which group represents $R^{12}$. Examples of groups listed above which are substituted by a further oxo group include 2,5-dioxo-pyrrolidin-1-yl, 2,6-dioxo-piperidin-1-yl, 2,5-dioxo-imidazolidin-1-yl, 2,6-dioxo-hexahydropyrimidin-1-yl, 1,3-dioxo-2,3-dihydro-1H-isoindol-2-yl (=1,3-dioxo-isoindol-2-yl) and 2,4-dioxo-thiazolidin-3-yl. Furthermore, as applies to the ring which can be formed by $R^1$ and $R^2$ together with the N—CO group in general, ring sulfur atoms in the listed heterocyclic groups can carry one or two oxo groups, i.e. doubly bonded oxygen atoms, and thus become SO or $SO_2$ groups, i.e. sulfoxide or sulfone groups or S-oxides or S,S-dioxides. For example, the sulfur atom in a 3-oxo-thiomorpholin-4-yl group can carry one or two oxo groups, and besides the 3-oxo-thiomorpholin-4-yl group also the groups 1,3-dioxo-thiomorpholin-4-yl and 1,1,3-trioxo-thiomorpholin-4-yl can be present in a compound of the invention.

Halogen is fluorine, chlorine, bromine or iodine, preferably fluorine, chlorine or bromine, more preferably fluorine or chlorine.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group. Evidently, an oxo group cannot occur as a substituent on a carbon atom in an aromatic ring.

The present invention includes all stereoisomeric forms of the compounds of the formulae I and Ia and their salts. With respect to each chiral center, independently of any other chiral center, the compounds of formulae I and Ia can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, the invention includes both the E form and Z form, or the cis form and the trans form, as well as mixtures of these forms in all ratios. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compound of the formula I or Ia or at the stage of a starting material or an intermediate during the synthesis. The present invention also includes all tautomeric forms of the compounds of formulae I and Ia and their salts.

In case the compounds of the formulae I and Ia contain one or more acidic and/or basic groups, i.e. salt-forming groups, the invention also comprises their corresponding physiologically or toxicologically acceptable salts, i.e. non-toxic salts, in particular their pharmaceutically acceptable salts. Thus, the compounds of the formulae I and Ia which contain an acidic group can be present on such groups, and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formulae I and Ia which contain a basic group, i.e. a group which can be protonated, can be present on such groups, and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formulae I and Ia simultaneously contain acidic and basic groups in the molecule, the invention also includes, in addition to the salt forms mentioned, inner salts or betaines or zwitterions. The salts of the compounds of the formulae I and Ia can be obtained by customary methods which are known to the person skilled in the art like, for example, by contacting the compound of the formula I or Ia with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formulae I and Ia, for example hydrates or adducts with alcohols, active metabolites of the compounds of the formulae I and Ia, and also prodrugs and derivatives of the compounds of the formulae I and Ia which in vitro may not necessarily exhibit pharmacological activity but which in vivo are converted into pharmacologically active compounds, for example esters or amides of carboxylic acid groups.

The group A in the compounds of the formulae I and Ia is preferably chosen from —$CH_2$—$CH_2$—$CH_2$— and —Y—$CH_2$—$CH_2$— wherein Y is chosen from O, S and $NR^{11}$ and Y is bonded to the group Het, and wherein all $CH_2$ groups can be substituted by one or more identical or different substituents $R^4$. In one embodiment of the present invention the $CH_2$ groups in the group A in the compounds of formulae I and Ia are not substituted by substituents $R^4$. If the $CH_2$ groups in the group A are not substituted, the divalent group -A- in the formulae I and Ia may be replaced with the group —Y'—$CH_2$—$CH_2$— wherein Y' is bonded to the group Het in formulae I and Ia, and Y' is chosen from a direct bond, $CH_2$, O, S and $NR^{11}$. Particularly preferably the group A in the compounds of the formulae I and Ia is chosen from —$CH_2$—$CH_2$—$CH_2$—, —NH—$CH_2$—$CH_2$— and —O—$CH_2$—$CH_2$—, more particularly preferably from —$CH_2$—$CH_2$—$CH_2$— and —O—$CH_2$—$CH_2$—, wherein the nitrogen atom and the oxygen atom are bonded to the group Het. In one embodiment of the present invention the group A is the group —O—$CH_2$—$CH_2$— wherein the oxygen atom is bonded to the group Het. The group Y is preferably chosen from O and $NR^{11}$ and more preferably is O.

In the compounds of the formula Ia the divalent group Het is preferably defined as in the compounds of the formula I. More generally, one embodiment of the present invention relates to the use of a compound of the formula I, which is defined as indicated above, in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other diseases mentioned above or below herein.

More preferably, the divalent group Het in the compounds of the formulae I and Ia is a divalent aromatic group of the formula II

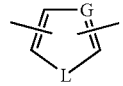

in which G is chosen from N and CH and L is chosen from S, O, $NR^{13}$, CH=CH, CH=N and N=CH, and which can be substituted by one or more identical or different substituents $R^5$, i.e. in which one or more ring carbon atoms can carry a substituent $R^5$ instead of the hydrogen atoms which are present on the carbon atoms depicted in formula II or which are specified in the definition of the groups G and L, with the proviso that the ring system depicted in formula II comprises at least one hetero ring member, i.e. a group $NR^{13}$ or an N, S or O atom, as a ring member. $R^5$ and $R^{13}$ in the ring system of the formula II are defined as indicated above with respect to the compounds of the formulae I and Ia. Particularly preferably the group Het in the compounds of the formulae I and Ia and the group of the formula II is chosen from the heteroarylene groups pyridinediyl, thiazolediyl, oxazolediyl, imidazolediyl and thiophenediyl, i.e. the divalent residues of pyridine, thiazole, oxazole, imidazole and thiophene, which can all be substituted by one or more identical or different substituents $R^5$ and wherein one of the ring nitrogen atoms of the imidazolediyl group, which represents the nitrogen atom in the group $NR^{13}$ in the definition of the group L, carries a group chosen from hydrogen and ($C_1$-$C_4$)-alkyl. More particularly preferably the group Het in the compounds of the formulae I and Ia and the group of the formula II is chosen from the heteroarylene groups pyridinediyl, thiazolediyl, imidazolediyl and thiophenediyl, especially preferably from pyridinediyl and thiazolediyl, which can all be substituted by one or more identical or different substituents $R^5$ and wherein one of the ring nitrogen atoms of the imidazolediyl group, which represents the nitrogen atom in the group $NR^{13}$ in the definition of the group L, carries a group chosen from hydrogen and ($C_1$-$C_4$)-alkyl. In one embodiment of the invention the group Het in the compounds of the formulae I and Ia and the group of the formula II is a pyridinediyl group which can be substituted by one or more identical or different substituents $R^5$.

In one embodiment of the present invention the groups representing the group Het in the compounds of the formulae I and Ia, including the group of the formula II in which the bonds via which it is connected to the two adjacent groups R³—X and A are represented by the lines intersecting the ring sides, are bonded to the adjacent groups R³—X and A via any two ring carbon atoms. Preferably a pyridinediyl group representing Het or the group of the formula II is bonded to the adjacent groups via positions 3 and 6 of the pyridine ring, which positions may also be numbered as positions 5 and 2, respectively, depending on the ranking order of the groups bonded to the pyridine ring, where each of the groups R³—X and A can be present in each of the positions. I.e., in the said pyridinediyl group, which is bonded via positions 3 and 6, the group R³—X can be present in position 3 and the group A in position 6, as well as the group R³—X can be present in position 6 and the group A in position 3, and preferably the group R³—X is present in position 6 and the group A in position 3.

Preferably a group of the formula IIa,

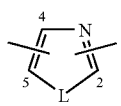

IIa which represents Het or the group of the formula II and in which L is O, S or NR¹³, i.e. which is a oxazolediyl, thiazolediyl or imidazolediyl group, is bonded to the adjacent groups via positions 2 and 5 or via positions 2 and 4, particularly preferably via positions 2 and 4, where each of the groups R³—X and A can be present in each of the positions and preferably the group R³—X is present in position 4 and the group A in position 2.

Preferably a thiophenediyl group which represents Het or the group of the formula II is bonded to the adjacent groups via positions 2 and 5 or via positions 2 and 4, which latter positions may also be numbered as positions 5 and 3, particularly preferably via positions 2 and 4, where each of the groups R³—X and A can be present in each of the positions and preferably the group R³—X is present in position 4 and the group A in position 2.

Preferred groups Het or groups of the formula II thus include the divalent heteroaromatic groups depicted in the following formulae IIIa to IIIg which represent preferred embodiments of the structural moiety R³—X-Het-A- in the compounds of the formulae I and Ia, and in which the heteroaromatic group can be unsubstituted or substituted by one or more identical or different substituents R⁵.

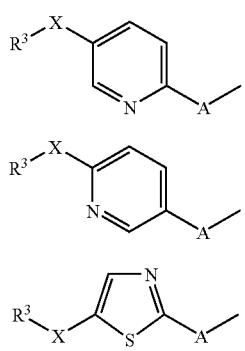

IIIa

IIIb

IIIc

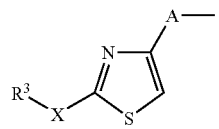

IIId

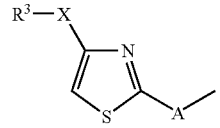

IIIe

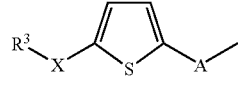

IIIf

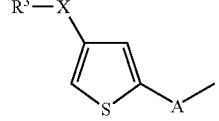

IIIg

Particularly preferred groups Het or groups of the formula II include the divalent heteroaromatic groups depicted in the formulae IIIb, IIIe and IIIg, especially the group depicted in formula IIIb, which represent particularly and especially preferred embodiments of the structural moiety R³—X-Het-A- in the compounds of the formulae I and Ia.

In the compounds of the formula Ia the group X is preferably chosen from a direct bond, CH₂, O and NH, or X is absent and in this latter case the phenyl or heteroaryl group representing the group R³ is fused to the group Het. Particularly preferably the group X in the compounds of the formulae I and Ia is chosen from a direct bond and O, or in the compounds of the formula Ia the group X is absent, and more particularly preferably the group X in the compounds of the formulae I and Ia is chosen from a direct bond and O. In one embodiment of the present invention the group X in the compounds of the formulae I and Ia is a direct bond. In another embodiment of the present invention the group X in the compounds of the formula Ia is absent and in this embodiment the phenyl, naphthalenyl or heteroaryl group representing the group R³ is fused to the group Het. In a further embodiment of the present invention the group X in the compounds of the formula Ia cannot be absent, i.e. in this embodiment the group X in the compounds of the formula Ia is chosen from a direct bond, CH₂, O, S, NH and N((C₁-C₄)-alkyl). In all cases in which X is absent the phenyl, naphthalenyl or heteroaryl group representing the group R³ is fused to the group Het or the ring system depicted in formula II which contains the groups G and L. In case X can be absent, in a particularly preferred embodiment of the present invention the structural moiety R³—X-Het- in the compounds of the formulae I and Ia is a bicyclic heteroaryl groups which comprises a monocyclic 5-membered or 6-membered heteroaromatic ring which represents the group Het and to which the group A is bonded, and a benzene ring which is fused to said heteroaromatic ring system and which represents the group R³, where the heteroaromatic ring can be substituted by one or more identical or different substituents R⁵ and the benzene ring can be substituted as indicated above with respect to R³. In case X is absent, the said structural moiety R³—X-Het- is more particularly preferably chosen from quinolinyl, isoquinolinyl, benzoimidazolyl, benzothiazolyl and benzothienyl, especially preferably from quinolinyl, benzoimidazolyl and benzothiazolyl, which are all bonded to the group A via the heterocyclic ring and which can be substituted as indicated.

If the ring which can be formed by the groups $R^1$ and $R^2$ together with the N—CO group which carries them is a monocyclic ring system, in one embodiment of the invention it is saturated or partially unsaturated. More specifically, in one embodiment it is saturated or contains one or two double bonds within the ring, and in another embodiment it is saturated or contains one double bond within the ring, and in a further embodiment it is saturated. If the said ring is a bicyclic ring system, in one embodiment the specific ring of the bicyclic ring system to which the group A is bonded is saturated or is partially unsaturated, and in a more specific embodiment this ring contains one or two double bonds within the ring of which one double bond can be common to both rings, and the second ring of the bicyclic ring system is a saturated or an aromatic ring, in particular an aromatic ring such as a benzene ring. Preferably, a monocyclic ring formed by the groups $R^1$ and $R^2$ together with the N—CO which carries them contains 4, 5, 6 or 7 ring members and a bicyclic ring system contains 9 or 10 ring members. The ring which can be formed by the groups $R^1$ and $R^2$ together with the N—CO group is preferably a monocyclic ring system. In one embodiment of the present invention, the ring which can be formed by the groups $R^1$ and $R^2$ together with the N—CO group which carries them can contain, in addition to the ring nitrogen atom being part of the N—CO group, one further hetero ring member, i.e. one further ring heteroatom or heteroatom group, which is chosen from N, $NR^{12}$, O, S, SO and $SO_2$ and preferably is chosen from $NR^{12}$, S, SO and $SO_2$ and more preferably is chosen from $NR^{12}$ and S. If the heterocycle formed by $R^1$ and $R^2$ and the N—CO group which carries them is substituted by one or more identical or different substituents $R^8$, it preferably is substituted by one, two, three, four or five, more preferably by one, two, three or four, particularly preferably by one, two or three, more particularly preferably by one or two identical or different substituents $R^8$ on ring carbon atoms, in addition to the oxo group depicted in formulae I and Ia and to oxo groups on ring sulfur atoms and/or groups $R^{12}$ on ring nitrogen atoms which may be present.

If $R^1$ and $R^2$, together with the N—CO group depicted in formulae I and Ia which carries them, form a ring, in one embodiment of the invention they form a saturated or unsaturated, monocyclic 4-membered to 7-membered ring, for example a monocyclic 5-membered or 6-membered ring, which, in addition to the ring nitrogen atom being part of the N—CO group, can contain one further hetero ring member group chosen from N, $NR^{12}$, O, S, SO and $SO_2$, wherein the ring formed by $R^1$ and $R^2$ and the N—CO group which carries them can be substituted by one or more identical or different substituents $R^8$. Further hetero ring members which are present in a ring formed by $R^1$ and $R^2$ together with the N—CO group which carries them are preferably chosen from $NR^{12}$, O and S, more preferably from $NR^{12}$ and S. The group —$N(R^2)$—CO—$R^1$ in the formulae I and Ia which results if $R^1$ and $R^2$ together with the N—CO group which carries them form a ring, is more preferably chosen from 2-oxo-azetidin-1-yl, 2-oxo-pyrrolidin-1-yl, 2-oxo-piperidin-1-yl, 2-oxo-1,2-dihydropyridin-1-yl, 2-oxo-azepan-1-yl, 2-oxo-imidazolidin-1-yl, 2-oxo-hexahydropyrimidin-1-yl, 2-oxo-1,2-dihydropyrimidin-1-yl, 2-oxo-piperazin-1-yl, 2-oxo-[1,3]diazepan-1-yl, 2-oxo-[1,4]diazepan-1-yl, 7-oxo-[1,4]diazepan-1-yl, 2-oxo-oxazolidin-3-yl, 2-oxo-[1,3]oxazinan-3-yl, 2-oxo-[1,3]oxazepan-3-yl, 3-oxo-morpholin-4-yl, 3-oxo-[1,4]oxazepan-4-yl, 5-oxo-[1,4]oxazepan-4-yl, 2-oxo-thiazolidin-3-yl, 2-oxo-[1,3]thiazinan-3-yl, 3-oxo-thiomorpholin-4-yl, 3-oxo-3,4-dihydro-2H-[1,4]thiazin-4-yl, 2-oxo-[1,3]thiazepan-3-yl, 3-oxo-[1,4]thiazepan-4-yl and 5-oxo-[1,4]thiazepan-4-yl, i.e. from the groups depicted in the following formulae

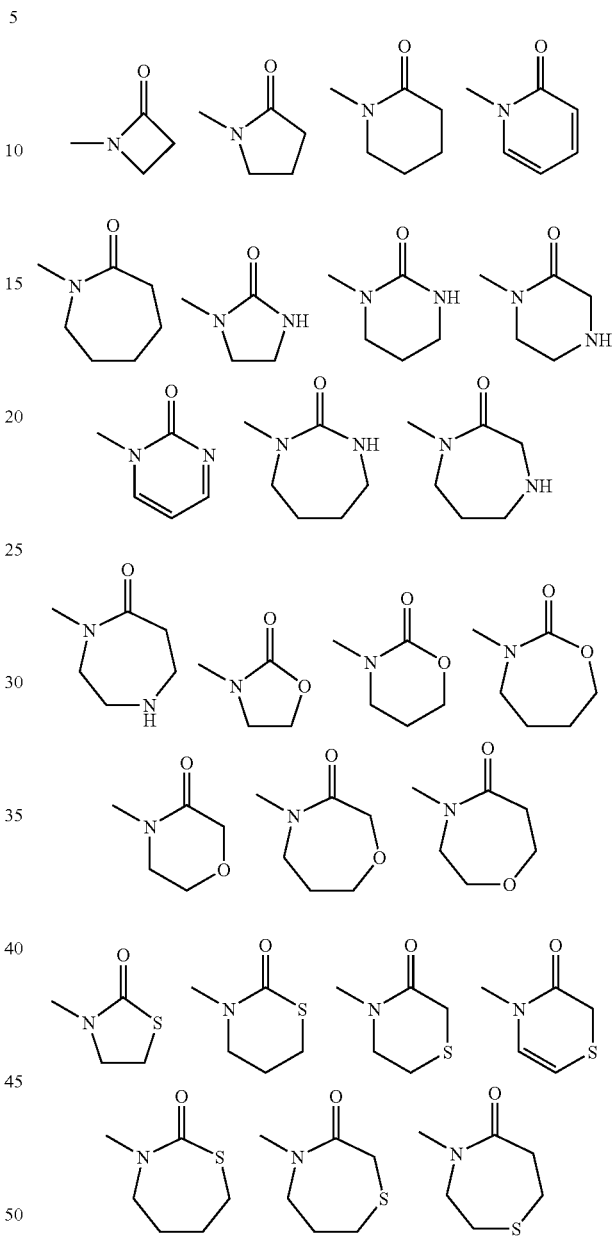

in which the bond via which the group is connected to the group A is depicted by a line starting at a ring nitrogen atom, and which in part may also be named differently as regards the indication of the saturation, for example as 3-oxo-2,3-dihydro-[1,4]thiazin-4-yl in the case of group 3-oxo-3,4-dihydro-2H-[1,4]thiazin-4-yl. Particularly preferably the group which results if $R^1$ and $R^2$ together with the N—CO group which carries them form a ring, is chosen from 2-oxo-azetidin-1-yl, 2-oxo-pyrrolidin-1-yl, 2-oxo-piperidin-1-yl, 2-oxo-1,2-dihydropyridin-1-yl, 2-oxo-azepan-1-yl, 2-oxo-imidazolidin-1-yl, 2-oxo-hexahydropyrimidin-1-yl, 2-oxo-[1,3]diazepan-1-yl, 2-oxo-thiazolidin-3-yl, 3-oxo-thiomorpholin-4-yl, 3-oxo-3,4-dihydro-2H-[1,4]thiazin-4-yl, i.e. from the groups depicted in the following formulae.

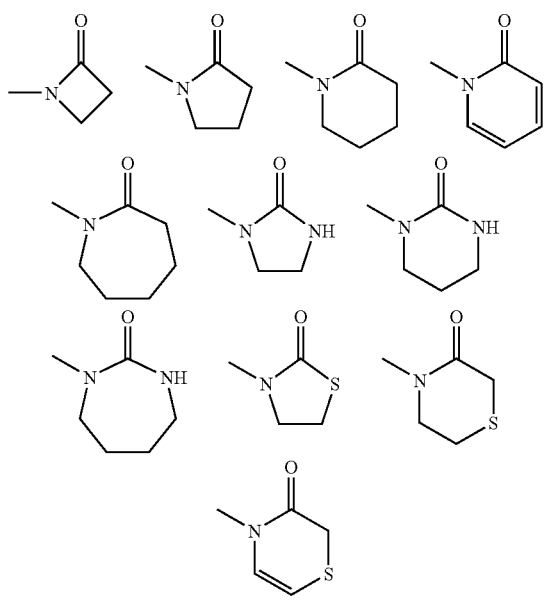

All the specified rings formed by $R^1$ and $R^2$ together with the N—CO group which carries them can be substituted on carbon atoms by one or more identical or different substituents $R^8$, and/or can carry on a ring nitrogen atom which is not bonded to the group A a group $R^{12}$, and/or can carry on a ring sulfur atom one or two oxo groups, to give a substituted group as indicated above. As examples of such groups which are substituted by an oxo group on a carbon atom or by one or two oxo groups on a sulfur atom, and which can represent the group —N($R^2$)—CO—$R^1$ in the formulae I and Ia and in which the bond via which the group is connected to the group A is depicted by a line starting at a ring nitrogen atom, the groups 2,5-dioxo-pyrrolidin-1-yl, 2,6-dioxo-piperidin-1-yl, 2,5-dioxo-imidazolidin-1-yl, 2,6-dioxo-hexahydropyrimidin-1-yl, 2,4-dioxo-thiazolidin-3-yl, 1,3-dioxo-thiomorpholin-4-yl and 1,1,3-trioxo-thiomorpholin-4-yl may be mentioned, i.e. groups of the following formulae,

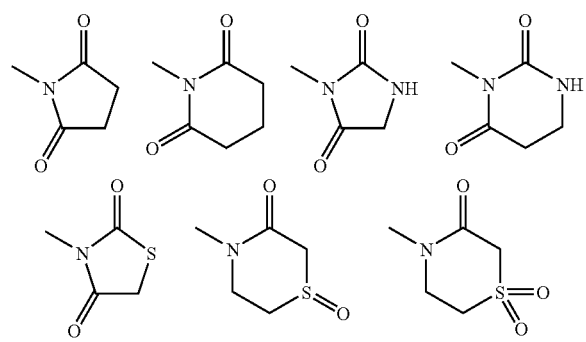

which can all be substituted additionally on carbon atoms by one or more identical or different substituents $R^8$ and/or can carry on a ring nitrogen atoms which is not bonded to the group A a group $R^{12}$, and which, like all suitable groups in the compounds of formulae I and Ia, can be present in tautomeric forms, for example as a 2,5-dihydroxypyrrol-1-yl group in the case of the 2,5-dioxo-pyrrolidin-1-yl group, as a 2,5-dihydroxyimidazol-1-yl group in the case of the 2,5-dioxo-imidazolidin-1-yl group, or as a 5-hydroxy-1,1-dioxo-2,3-dihydro-[1,4]thiazin-4-yl group in the case of the 1,1,3-trioxo-thiomorpholin-4-yl group.

If $R^1$ and $R^2$ do not form a ring together with the N—CO group which carries them, they preferably are independently of each other chosen from ($C_1$-$C_4$)-alkyl, ($C_3$-$C_7$)-cycloalkyl-$C_nH_{2n}$—, phenyl-$C_nH_{2n}$— and heteroaryl-$C_nH_{2n}$—, more preferably from ($C_1$-$C_4$)-alkyl, ($C_3$-$C_7$)-cycloalkyl-, phenyl, phenyl-$CH_2$—, heteroaryl and heteroaryl-$CH_2$—, particularly preferably from ($C_1$-$C_4$)-alkyl, ($C_3$-$C_7$)-cycloalkyl-, phenyl- and heteroaryl-, and in each case $R^2$ can in addition be hydrogen, wherein the groups ($C_1$-$C_4$)-alkyl and ($C_3$-$C_7$)-cycloalkyl can both be substituted by one or more identical or different substituents $R^6$, and the groups phenyl and heteroaryl can both be substituted by one or more identical or different substituents $R^7$. If $R^1$ and $R^2$ do not form a ring together with the N—CO group which carries them, in one embodiment of the present invention $R^2$ is hydrogen and $R^1$ is defined as indicated. If $R^2$ is an alkenyl group or an alkynyl group, preferably the nitrogen atom carrying $R^2$ is not in conjugation with a double bond or triple bond, i.e., preferably the nitrogen atom carrying $R^2$ is not directly bonded to a carbon atom in an alkenyl group or alkynyl group which is part of a double bond or triple bond.

In the compounds of the formula Ia the groups $R^1$ and $R^2$ preferably are independently of each other chosen from ($C_1$-$C_6$)-alkyl, ($C_3$-$C_6$)-alkenyl, ($C_3$-$C_6$)-alkynyl, ($C_3$-$C_7$)-cycloalkyl-$C_nH_{2n}$—, phenyl-$C_nH_{2n}$— and heteroaryl-$C_nH_{2n}$—, and $R^2$ can in addition be hydrogen, wherein the groups ($C_1$-$C_6$)-alkyl, ($C_3$-$C_7$)-cycloalkyl, ($C_3$-$C_6$)-alkenyl and ($C_3$-$C_6$)-alkynyl can all be substituted by one or more identical or different substituents $R^6$, and the groups $C_nH_{2n}$ can all be substituted by one or more identical or different substituents chosen from fluorine and ($C_1$-$C_4$)-alkyl, and all phenyl groups and heteroaryl groups can be substituted by one or more identical or different substituents $R^7$, or $R^1$ and $R^2$, together with the N—CO group which carries them, form a 4-membered 5 to 10-membered, monocyclic or bicyclic, saturated or unsaturated ring which, in addition to the ring nitrogen atom being part of the N—CO group, can contain one or two further hetero ring members or heteroatom groups chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$.

Particularly preferably, in the compounds of the formula Ia the groups $R^1$ and $R^2$ are chosen from ($C_1$-$C_4$)-alkyl, ($C_3$-$C_7$)-cycloalkyl-$C_nH_{2n}$—, phenyl-$C_nH_{2n}$— and heteroaryl-$C_nH_{2n}$—, and $R^2$ can in addition be hydrogen, wherein the groups ($C_1$-$C_4$)-alkyl and ($C_3$-$C_7$)-cycloalkyl can both be substituted by one or more identical or different substituents $R^6$, and all phenyl groups and heteroaryl groups can be substituted by one or more identical or different substituents $R^7$, or $R^1$ and $R^2$, together with the N—CO group which carries them, form a 4-membered to 7-membered, monocyclic, saturated or unsaturated ring which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$.

In the compounds of the formula I the groups $R^1$ and $R^2$, together with the N—CO group which carries them, preferably form a 4-membered to 7-membered, monocyclic, saturated or unsaturated ring which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$.

In one embodiment of the present invention, the groups $R^1$ and $R^2$ in the compounds of formulae I and Ia, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$, and wherein preferred features of this embodiment are those outlined above. For example, in a preferred feature of this embodiment the ring formed by $R^1$ and $R^2$ together with the N—CO group which carries them is a saturated or unsaturated, monocyclic 4-membered to 7-membered ring, for example a 5-membered or 6-membered ring, which, in addition to the ring nitrogen atom being part of the N—CO group, can contain one further hetero ring member which is preferably chosen from $NR^{12}$, O and S, more preferably from $NR^{12}$ and S, and which can be substituted, for example, by an oxo group on a carbon atom. In one embodiment of the present invention the ring formed by $R^1$ and $R^2$ and the N—CO group which carries them does not contain a further hetero ring member in addition to the nitrogen atom which is part of the N—CO group, where in this embodiment the ring can likewise be substituted as indicated.

In the compounds of the formula Ia the group $R^3$ is preferably chosen from phenyl, naphthalenyl and heteroaryl which can all be substituted by one or more identical or different substituents chosen from halogen, $(C_1\text{-}C_4)$-alkyl, $(C_1\text{-}C_4)$-alkyloxy-$(C_1\text{-}C_2)$-alkyl-, OH, $(C_1\text{-}C_4)$-alkyloxy which can be substituted by one or more fluorine atoms, $(C_1\text{-}C_2)$-alkylenedioxy which can be substituted by one or more fluorine atoms, $(C_1\text{-}C_4)$-alkylmercapto, $NH_2$, $(C_1\text{-}C_4)$-alkylamino, di($(C_1\text{-}C_4)$-alkyl)amino, $((C_1\text{-}C_4)$-alkyl)-CONH—, $((C_1\text{-}C_4)$-alkyl)-$SO_2NH$—, di($(C_1\text{-}C_4)$-alkyl)aminocarbonyl-, $((C_1\text{-}C_4)$-alkyl)aminocarbonyl-, $((C_1\text{-}C_4)$-alkyloxy)carbonyl-, COOH, $CONH_2$, CN, $CF_3$, $H_2NSO_2$— and $(C_1\text{-}C_4)$-alkyl-$SO_2$—, and more preferably by one or more identical or different substituents chosen from halogen, $(C_1\text{-}C_4)$-alkyl, $(C_1\text{-}C_4)$-alkyloxy-$(C_1\text{-}C_2)$-alkyl-, OH, $(C_1\text{-}C_4)$-alkyloxy which can be substituted by one or more fluorine atoms, $(C_1\text{-}C_2)$-alkylenedioxy which can be substituted by one or more fluorine atoms, $(C_1\text{-}C_4)$-alkylmercapto, $NH_2$, $(C_1\text{-}C_4)$-alkylamino, di($(C_1\text{-}C_4)$-alkyl)amino, $((C_1\text{-}C_4)$-alkyl)-CONH—, di($(C_1\text{-}C_4)$-alkyl)aminocarbonyl-, $((C_1\text{-}C_4)$-alkyl)aminocarbonyl-, $((C_1\text{-}C_4)$-alkyloxy)carbonyl-, COOH, $CONH_2$, CN, $CF_3$, $H_2NSO_2$— and $(C_1\text{-}C_4)$-alkyl-$SO_2$—. Particularly preferably the group $R^3$ in the compounds of the formulae I and Ia is chosen from phenyl, naphthalenyl and heteroaryl, and preferably is a phenyl group or heteroaryl group and more preferably is a phenyl group, which groups can all be substituted by one or more identical or different substituents which are chosen from halogen, $(C_1\text{-}C_4)$-alkyl, $(C_1\text{-}C_4)$-alkyloxy-$(C_1\text{-}C_2)$-alkyl-, $(C_1\text{-}C_4)$-alkyloxy which can be substituted by one or more fluorine atoms, $(C_1\text{-}C_4)$-alkylmercapto, $(C_1\text{-}C_4)$-alkylamino, di($(C_1\text{-}C_4)$-alkyl)amino, $CONH_2$, CN, $CF_3$ and $(C_1\text{-}C_4)$-alkyl-$SO_2$—. A heteroaryl group representing $R^3$ is preferably chosen from pyridinyl, quinolinyl, thiophenyl, isoxazolyl and pyrimidinyl, more preferably from pyridinyl, pyrimidinyl, isoxazolyl and thiophenyl, and is thiophenyl in one embodiment of the invention, which groups can all be substituted as indicated. Preferably the optional substituents on the group $R^3$ are chosen from halogen, $(C_1\text{-}C_4)$-alkyl, $(C_1\text{-}C_4)$-alkyloxy which can be substituted by one or more fluorine atoms, and $CF_3$, more preferably from halogen and $(C_1\text{-}C_4)$-alkyl. Particularly preferably $R^3$ is a phenyl group which can be substituted by one or more identical or different substituents which are chosen from halogen, $(C_1\text{-}C_4)$-alkyl and $CF_3$. Especially preferably $R^3$ is a phenyl group which is substituted by one or more identical or different substituents chosen from halogen atoms and $(C_1\text{-}C_4)$-alkyl groups, in particular from fluorine atoms, chlorine atoms, methyl groups and ethyl groups. A phenyl group representing $R^3$ is preferably a substituted phenyl group. In a substituted group $R^3$ the number of substituents preferably is one, two, three, four or five, more preferably one, two, three or four, particularly preferably one, two or three, more particularly preferably one or two. In one embodiment of the present invention the group $R^3$ is a carbocyclic group, i.e. a phenyl group or a naphthalenyl group, and in another embodiment of the invention the group $R^3$ is a monocyclic group, i.e. a phenyl group or a monocyclic heteroaryl group, for example a thienyl group, and in another embodiment of the invention $R^3$ is a phenyl group, a naphthalenyl group or a monocyclic heteroaryl group, for example a thienyl group, where all these groups can be substituted as indicated. In one embodiment of the present invention the group $R^3$ in the compounds of the formula Ia is chosen from phenyl, naphthalenyl and heteroaryl which can all be substituted by one or more identical or different substituents chosen from halogen, $(C_1\text{-}C_6)$-alkyl, $(C_1\text{-}C_6)$-alkyloxy-$(C_1\text{-}C_6)$-alkyl-, OH, $(C_1\text{-}C_6)$-alkyloxy which can be substituted by one or more fluorine atoms, $(C_1\text{-}C_3)$-alkylenedioxy which can be substituted by one or more fluorine atoms, $(C_1\text{-}C_6)$-alkylmercapto, $NH_2$, $(C_1\text{-}C_6)$-alkylamino, di($(C_1\text{-}C_6)$-alkyl)amino, $((C_1\text{-}C_6)$-alkyl)-CONH—, di($(C_1\text{-}C_6)$-alkyl)aminocarbonyl-, $((C_1\text{-}C_6)$-alkyl)aminocarbonyl-, $((C_1\text{-}C_6)$-alkyloxy)carbonyl-, COOH, $CONH_2$, CN, $CF_3$, $((C_1\text{-}C_6)$-alkyl)$NHSO_2$—, di($(C_1\text{-}C_6)$-alkyl)$NSO_2$—, $H_2NSO_2$— and $(C_1\text{-}C_6)$-alkyl-$SO_2$—.

In the compounds of the formula Ia the group $R^4$ is preferably chosen from $(C_1\text{-}C_4)$-alkyl and fluorine. Particularly preferably the group $R^4$ in the compounds of the formulae I and Ia is chosen from methyl and fluorine, and especially preferably $R^4$ is fluorine. The total number of substituents $R^4$ in a substituted group A, which in general can be one, two, three, four, five or six, is preferably one, two, three or four, more preferably one or two.

In the compounds of the formula Ia the group $R^5$ is preferably chosen from halogen, $(C_1\text{-}C_4)$-alkyl, $(C_1\text{-}C_4)$-alkyloxy-$(C_1\text{-}C_2)$-alkyl-, OH, $(C_1\text{-}C_4)$-alkyloxy which can be substituted by one or more fluorine atoms, $(C_1\text{-}C_4)$-alkylmercapto, $NH_2$, $(C_1\text{-}C_4)$-alkylamino, di($(C_1\text{-}C_4)$-alkyl)amino, $((C_1\text{-}C_4)$-alkyl)-CONH—, di($(C_1\text{-}C_4)$-alkyl)aminocarbonyl-, $((C_1\text{-}C_4)$-alkyl)aminocarbonyl-, $((C_1\text{-}C_4)$-alkyloxy)carbonyl-, COOH, $CONH_2$, CN, $CF_3$ and $(C_1\text{-}C_4)$-alkyl-$SO_2$—. Particularly preferably the group $R^5$ in the compounds of the formulae I and Ia is chosen from halogen, $(C_1\text{-}C_4)$-alkyl, $(C_1\text{-}C_4)$-alkyloxy-$(C_1\text{-}C_2)$-alkyl-, OH, $(C_1\text{-}C_4)$-alkyloxy which can be substituted by one or more fluorine atoms, $(C_1\text{-}C_4)$-alkylmercapto, $NH_2$, $(C_1\text{-}C_4)$-alkylamino, di($(C_1\text{-}C_4)$-alkyl)amino, $((C_1\text{-}C_4)$-alkyl)-CONH—, $CONH_2$, CN, $CF_3$ and $(C_1\text{-}C_4)$-alkyl-$SO_2$—, more particularly preferably from halogen, $(C_1\text{-}C_4)$-alkyl and $CF_3$. Especially preferably the group Het in the compounds of the formulae I and Ia is unsubstituted or substituted by one or more identical or different substituents chosen from fluorine, chlorine, methyl and $CF_3$, in particular fluorine, chlorine and methyl, for example fluorine substituents, and more especially preferably the group Het is unsubstituted. The number of substituents $R^5$, which are present on a substituted group Het, preferably is one, two, three or four, more preferably one, two or three, particularly preferably one or two, more particularly preferably one.

In the compounds of the formula Ia the group $R^6$ is preferably chosen from fluorine, OH, oxo, $(C_1-C_4)$-alkyloxy, $(C_1-C_4)$-alkylmercapto, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, COOH, $CONH_2$, CN and $CF_3$. Particularly preferably the group $R^6$ in the compounds of the formulae I and Ia is chosen from fluorine, $(C_1-C_4)$-alkyloxy, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, COOH and $CF_3$, more particularly preferably from fluorine, $((C_1-C_4)$-alkyloxy)carbonyl- and COOH, especially preferably from $((C_1-C_4)$-alkyloxy)carbonyl- and COOH. The number of substituents $R^6$ preferably is one, two or three, more preferably one or two, particularly preferably one.

In the compounds of the formula Ia the group $R^7$ is preferably chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—. Particularly preferably the group $R^7$ in the compounds of the formulae I and Ia is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—, more particularly preferably from halogen, $(C_1-C_4)$-alkyl, $NH_2$, $(C_1-C_4)$-alkylamino, di$((C_1-C_4)$-alkyl)amino, $((C_1-C_4)$-alkyl)-CONH— and $CF_3$, especially preferably from fluorine, chlorine, methyl, $NH_2$ and $CF_3$. The number of substituents $R^7$ preferably is one, two, three or four, more preferably one, two or three, particularly preferably one or two, more particularly preferably one.

In the compounds of the formula Ia the group $R^8$ is preferably chosen from halogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. Particularly preferably the group $R^8$ in the compounds of the formulae I and Ia is chosen from halogen, $(C_1-C_4)$-alkyl, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, $CONH_2$, CN and $CF_3$, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. More particularly preferably the group $R^8$ in the compounds of the formulae I and Ia is chosen from halogen, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $((C_1-C_4)$-alkyl)-CONH—, di$((C_1-C_4)$-alkyl)aminocarbonyl- and $CF_3$, especially preferably from halogen, $(C_1-C_4)$-alkyl, oxo, $(C_1-C_4)$-alkyloxy which can be substituted by one or more fluorine atoms, and $CF_3$, more especially preferably from halogen, $(C_1-C_4)$-alkyl, oxo and $CF_3$. Substituents $R^8$ which are present in a non-aromatic ring in the heterocycle formed by $R^1$ and $R^2$ together with the N—CO group which carries them, in particular in the ring which contains the said N—CO group, for example in a non-aromatic monocyclic heterocycle formed by $R^1$ and $R^2$ together with the N—CO group, are preferably chosen from $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $NH_2$, $(C_1-C_4)$-alkylamino, di$((C_1-C_4)$-alkyl)amino and $((C_1-C_4)$-alkyl)-CONH—, more preferably from $(C_1-C_4)$-alkyl, $(C_3-C_7)$-cycloalkyl-$C_nH_{2n}$—, phenyl-$C_nH_{2n}$—, heteroaryl-$C_nH_{2n}$— and oxo, particularly preferably from $(C_1-C_4)$-alkyl and oxo, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. The number of substituents $R^8$ preferably is one, two, three, four or five, more preferably one, two, three or four, particularly preferably one, two or three, more particularly preferably one or two.

In the compounds of the formula Ia the group $R^{11}$ is preferably chosen from hydrogen, $(C_1-C_4)$-alkyl and $((C_1-C_4)$-alkyl)-CO—. Particularly preferably the group $R^{11}$ in the compounds of the formulae I and Ia is chosen from hydrogen and $(C_1-C_4)$-alkyl, more particularly preferably from hydrogen and methyl. Especially preferably $R^{11}$ is hydrogen.

In the compounds of the formula Ia the group $R^{12}$ is preferably chosen from hydrogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $((C_1-C_4)$-alkyl)-CO—, $(C_3-C_7)$-cycloalkyl-$C_nH_{2n}$—CO—, phenyl-$C_nH_{2n}$—CO—, heteroaryl-$C_nH_{2n}$—CO—, $((C_1-C_4)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy. Particularly preferably the group $R^{12}$ in the compounds of the formulae I and Ia is chosen from hydrogen, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO—, $((C_1-C_4)$-alkyl)-O—CO— and phenyl-$C_nH_{2n}$—O—CO—, more particularly preferably from hydrogen, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO— and $((C_1-C_4)$-alkyl)-O—CO—, especially preferably from hydrogen, $(C_1-C_4)$-alkyl and $(C_3-C_7)$-cycloalkyl-$C_nH_{2n}$—, more especially preferably from hydrogen and $(C_1-C_4)$-alkyl. In one embodiment of the present invention the group $R^{12}$ is hydrogen.

In the compounds of the formulae I and Ia the group $R^{13}$ is preferably chosen from hydrogen and $(C_1-C_4)$-alkyl and more preferably from hydrogen and methyl. Particularly preferably $R^{13}$ is hydrogen.

In the compounds of the formula Ia a heteroaryl group is preferably a 5-membered or 6-membered, monocyclic aromatic group which contains one, two or three identical or different hetero ring members chosen from N, $NR^{13}$, O and S. Particularly preferably a heteroaryl group in the compounds of the formulae I and Ia is a 5-membered or 6-membered, monocyclic aromatic group which contains one or two identical or different hetero ring members chosen from N, $NR^{13}$, O and S.

In the compounds of the formula Ia the number n is preferably 0, 1 or 2, wherein all numbers n are independent of each other and can be identical or different. Particularly preferably the number n in the compounds of the formulae I and Ia is 0 or 1, wherein all numbers n are independent of each other and can be identical or different. An example of the group phenyl-$C_nH_{2n}$— in which the number n is 1 is the benzyl group (=phenyl-$CH_2$—).

In preferred embodiments of the present invention one or more or all of the groups contained in the compounds of formulae I and Ia can independently of each other have any of the preferred definitions of the groups specified above or any one or some of the specific denotations which are comprised by the definitions of the groups and specified above, all combinations of preferred definitions and/or specific denotations being a subject of the present invention. Also with respect to all preferred embodiments the invention includes the compounds of the formulae I and Ia in all stereoisomeric forms and mixtures of stereoisomeric forms in all ratios, and their physiologically acceptable salts, as well as their tautomeric forms.

For example, one such embodiment of the present invention relates to compounds of the formula Ia in which simultaneously A is chosen from —$CH_2$—$CH_2$—$CH_2$— and —Y—$CH_2$—$CH_2$— wherein all $CH_2$ groups can be substituted by one or more identical or different substituents $R^4$, and wherein Y is chosen from O, S and $NR^{11}$ and Y is bonded to the group Het;

Het is chosen from pyridinediyl, thiazolediyl, oxazolediyl, imidazolediyl and thiophenediyl which can all be substituted by one or more identical or different substituents $R^5$ and wherein one of the ring nitrogen atoms of the imidazolediyl group carries a group chosen from hydrogen and ($C_1$-$C_4$)-alkyl;

X is chosen from a direct bond and O;

$R^1$ and $R^2$ are independently of each other chosen from ($C_1$-$C_4$)-alkyl, ($C_3$-$C_7$)-cycloalkyl-$C_nH_{2n}$—, phenyl-$C_nH_{2n}$—, and heteroaryl-$C_nH_{2n}$—, and $R^2$ can in addition be hydrogen, wherein the groups ($C_1$-$C_4$)-alkyl and ($C_3$-$C_7$)-cycloalkyl can both be substituted by one or more identical or different substituents $R^6$, and all phenyl groups and heteroaryl groups can be substituted by one or more identical or different substituents $R^7$, or $R^1$ and $R^2$, together with the N—CO group which carries them, form a 4-membered to 7-membered, monocyclic, saturated or unsaturated heterocycle which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—;

$R^4$ is chosen from methyl and fluorine;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—;

$R^6$ is chosen from fluorine, ($C_1$-$C_4$)-alkyloxy, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyloxy)carbonyl-, COOH and $CF_3$;

$R^7$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_2$)-alkylenedioxy which can be substituted by one or more fluorine atoms, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—;

$R^8$ is chosen from halogen, ($C_1$-$C_4$)-alkyl, phenyl-$C_nH_{2n}$—, heteroaryl-$C_nH_{2n}$—, ($C_1$-$C_4$)-alkyloxy-($C_1$-$C_2$)-alkyl-, OH, oxo, ($C_1$-$C_4$)-alkyloxy which can be substituted by one or more fluorine atoms, ($C_1$-$C_2$)-alkylenedioxy which can be substituted by one or more fluorine atoms, ($C_1$-$C_4$)-alkylmercapto, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyloxy)carbonyl-, $CONH_2$, CN and $CF_3$, wherein all phenyl groups and heteroaryl groups can independently of each other be substituted by one or more identical or different substituents chosen from halogen, ($C_1$-$C_4$)-alkyl, $CF_3$ and ($C_1$-$C_4$)-alkyloxy;

$R^{11}$ is chosen from H and ($C_1$-$C_4$)-alkyl;

$R^{12}$ is chosen from H, ($C_1$-$C_4$)-alkyl, ($C_3$-$C_7$)-cycloalkyl-$C_nH_{2n}$—, (($C_1$-$C_4$)-alkyl)-CO—, ($C_3$-$C_7$)-cycloalkyl-$C_nH_{2n}$—CO— and (($C_1$-$C_4$)-alkyl)-O—CO—;

$R^{13}$ is chosen from hydrogen and ($C_1$-$C_4$)-alkyl;

heteroaryl is a 5-membered or 6-membered, monocyclic aromatic group containing one or two identical or different hetero ring members chosen from N, $NR^{13}$, O and S;

n is 0 or 1, wherein all numbers n are independent of each other and can be identical or different;

in any of its stereoisomeric forms or a mixture of stereoisomeric forms in any ratio, or a physiologically acceptable salt thereof.

Another such embodiment of the present invention relates to compounds of the formula Ia, in which simultaneously A is chosen from —$CH_2$—$CH_2$—$CH_2$— and —Y—$CH_2$—$CH_2$— wherein all $CH_2$ groups can be substituted by one or more identical or different substituents $R^4$, and wherein Y is chosen from O, S and $NR^{11}$ and Y is bonded to the group Het;

Het is chosen from pyridinediyl and thiazolediyl which can all be substituted by one or more identical or different substituents $R^5$;

X is a direct bond;

and the other groups are defined as in any other definition of the compounds of the formula Ia above or below;

in any of its stereoisomeric forms or a mixture of stereoisomeric forms in any ratio, or a physiologically acceptable salt thereof.

Another such embodiment of the present invention relates to compounds of the formulae I and Ia in which simultaneously A is chosen from —$CH_2$—$CH_2$—$CH_2$— and —Y—$CH_2$—$CH_2$— wherein all $CH_2$ groups can be substituted by one or more identical or different substituents $R^4$, and wherein Y is chosen from O, S and $NR^{11}$ and Y is bonded to the group Het;

Het is chosen from pyridinediyl, thiazolediyl, oxazolediyl, imidazolediyl and thiophenediyl which can all be substituted by one or more identical or different substituents $R^5$ and wherein one of the ring nitrogen atoms of the imidazolediyl group carries a group chosen from hydrogen and $(C_1-C_4)$-alkyl;

X is chosen from a direct bond and O;

$R^1$ and $R^2$, together with the N—CO group which carries them, form a 4-membered to 7-membered, monocyclic, saturated or unsaturated heterocycle which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^4$ is chosen from methyl and fluorine;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^8$ is chosen from halogen, $(C_1-C_4)$-alkyl, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, $CONH_2$, CN and $CF_3$, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy;

$R^{11}$ is chosen from H and $(C_1-C_4)$-alkyl;

$R^{12}$ is chosen from H, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO— and $((C_1-C_4)$-alkyl)-O—CO—;

$R^{13}$ is chosen from hydrogen and $(C_1-C_4)$-alkyl;

heteroaryl is a 5-membered or 6-membered, monocyclic aromatic group containing one or two identical or different hetero ring members chosen from N, $NR^{13}$, O and S;

n is 0 or 1, wherein all numbers n are independent of each other and can be identical or different;

in any of its stereoisomeric forms or a mixture of stereoisomeric forms in any ratio, or a physiologically acceptable salt thereof.

Another such embodiment of the present invention relates to compounds of the formulae I and Ia in which simultaneously A is chosen from —$CH_2$—$CH_2$—$CH_2$— and —Y—$CH_2$—$CH_2$— wherein Y is chosen from O and NH and wherein Y is bonded to the group Het;

Het is chosen from pyridinediyl, thiazolediyl, oxazolediyl, imidazolediyl and thiophenediyl which can all be substituted by one or more identical or different substituents $R^5$ and wherein one of the ring nitrogen atoms of the imidazolediyl group carries a group chosen from hydrogen and $(C_1-C_4)$-alkyl;

X is chosen from a direct bond and O;

$R^1$ and $R^2$, together with the N—CO group which carries them, form a 4-membered to 7-membered, monocyclic, saturated or unsaturated heterocycle which, in addition to the nitrogen atom being part of the N—CO group, can contain one further hetero ring member chosen from $NR^{12}$, O and S, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^8$ is chosen from $(C_1-C_4)$-alkyl and oxo;

$R^{12}$ is chosen from H and $(C_1-C_4)$-alkyl-;

in any of its stereoisomeric forms or a mixture of stereoisomeric forms in any ratio, or a physiologically acceptable salt thereof.

Another such embodiment of the present invention relates to compounds of the formulae I and Ia in which simultaneously A is chosen from —$CH_2$—$CH_2$—$CH_2$— and —Y—$CH_2$—$CH_2$— wherein Y is chosen from O and NH and Y is bonded to the group Het;

Het is a pyridinediyl or thiazolediyl group which can all be substituted by one or more identical or different substituents $R^5$;

X is a direct bond;

$R^1$ and $R^2$, together with the N—CO group which carries them, form a saturated or unsaturated, monocyclic 4-membered to 7-membered ring which, in addition to the ring nitrogen atom being part of the N—CO group, can contain one further hetero ring member chosen from $NR^{12}$, O and S, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^8$ is chosen from $(C_1-C_4)$-alkyl and oxo;

$R^{12}$ is chosen from H and $(C_1-C_4)$-alkyl-;

in any of its stereoisomeric forms or a mixture of stereoisomeric forms in any ratio, or a physiologically acceptable salt thereof;

where in this embodiment the group Het preferably is a pyridinediyl group which can be substituted by one or more identical or different substituents $R^5$.

Another such embodiment of the present invention relates to novel compounds of the formula I

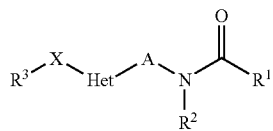

in which

A is chosen from —$CH_2$—$CH_2$—, —$CH_2$—$CH_2$—$CH_2$— and —Y—$CH_2$—$CH_2$—, wherein all $CH_2$ groups can be substituted by one or more identical or different substituents $R^4$, and wherein Y is chosen from O, S and $NR^{11}$ and Y is bonded to the group Het;

Het is a 5-membered or 6-membered, monocyclic aromatic group which contains one or two identical or different hetero ring members chosen from N, $NR^{13}$, O and S and which can be substituted by one or more identical or different substituents $R^5$;

X is chosen from a direct bond, $CH_2$, O and NH;

$R^1$ and $R^2$ are independently of each other chosen from $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, and $R^2$ can in addition be hydrogen, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl groups and heteroaryl groups can independently of each other be substituted by one or more identical or different substituents $R^7$, or $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$;

$R^3$ is chosen from phenyl, naphthalenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—;

$R^4$ is chosen from $(C_1-C_4)$-alkyl and fluorine;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ and $(C_1-C_4)$-alkyl-$SO_2$—;

$R^6$ is chosen from fluorine, OH, oxo, $(C_1-C_4)$-alkyloxy, $(C_1-C_4)$-alkylmercapto, di($(C_1-C_4)$-alkyl)amino, $((C_1-C_4)$-alkyl)-CONH—, di($(C_1-C_4)$-alkyl)aminocarbonyl-, $((C_1-C_4)$-alkyloxy)carbonyl-, COOH, $CONH_2$, CN and $CF_3$;

$R^7$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—;

$R^8$ is chosen from halogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy;

$R^{11}$ is chosen from hydrogen, $(C_1-C_4)$-alkyl and $((C_1-C_4)$-alkyl)-CO—;

$R^{12}$ is chosen from hydrogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $((C_1-C_4)$-alkyl)-CO—, $(C_3-C_7)$-cycloalkyl-$C_nH_{2n}$—CO—, phenyl-$C_nH_{2n}$—CO—, heteroaryl-$C_nH_{2n}$—CO—, $((C_1-C_4)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy;

$R^{13}$ is chosen from hydrogen, $(C_1-C_4)$-alkyl and phenyl-$C_nH_{2n}$—, wherein the phenyl group can be substituted by one or more identical or different substituents chosen from halogen, $(C_1-C_4)$-alkyl, $CF_3$ and $(C_1-C_4)$-alkyloxy, where all groups $R^{13}$ are independent of each other and can be identical or different;

heteroaryl is a 5-membered or 6-membered, monocyclic aromatic group which contains one, two or three identical or different hetero ring members chosen from N, $NR^{13}$, O and S;

n is 0, 1 or 2, where all numbers n are independent of each other and can be identical or different;

in any of its stereoisomeric forms or a mixture of stereoisomeric forms in any ratio, or a physiologically acceptable salt thereof;

excluding compounds comprised by this definition which have already been described such as 2-(2-acetylaminoethylamino)-3-cyano-5-(pyridin-4-yl)pyridine, 2-(2-propionylaminoethylamino)-3-cyano-5-(pyridin-4-yl)pyridine and 3-cyano-2-(2-nicotinoylaminoethylamino)-5-(pyridin-4-yl)pyridine.

Another such embodiment of the present invention relates to compounds of the formula Ia in which simultaneously A is chosen from —$CH_2$—$CH_2$—$CH_2$— and —Y—$CH_2$—$CH_2$— wherein Y is chosen from O and NH and wherein Y is bonded to the group Het;

Het is chosen from the pyridinediyl, thiazolediyl, oxazolediyl, imidazolediyl and thiophenediyl which can all be substituted by one or more identical or different substituents R⁵ and wherein one of the ring nitrogen atoms of the imidazolediyl group carries a group chosen from hydrogen and ($C_1$-$C_4$)-alkyl;

X is absent and the phenyl group representing the group $R^3$ is fused to the group Het;

$R^1$ and $R^2$, together with the N—CO group which carries them, form a 4-membered to 7-membered, monocyclic, saturated or unsaturated heterocycle which, in addition to the ring nitrogen atom being part of the N—CO group, can contain one further hetero ring member chosen from $NR^{12}$, O and S, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—;

$R^8$ is chosen from ($C_1$-$C_4$)-alkyl and oxo;

$R^{12}$ is chosen from H and ($C_1$-$C_4$)-alkyl-;

in any of its stereoisomeric forms or a mixture of stereoisomeric forms in any ratio, or a physiologically acceptable salt thereof.

Besides the use of the compounds of the formula Ia defined afore in which the group X is absent, for the manufacture of a medicament for the stimulation of the expression of endothelial NO synthase and for the treatment of a disease in which such a stimulation, or an increase in NO level, is desired, for example cardiovascular disorders such as atherosclerosis, coronary artery disease or cardiac insufficiency or any other diseases mentioned above or below herein, also the novel compounds of the formula Ia defined afore in which the group X is absent, themselves, i.e. the novel compounds per se, are a subject of the present invention.

As in any embodiment of the invention, in the preceding embodiments, which contain exemplary definitions of compounds according to the invention, one or more or all of the groups can have any of its preferred definitions specified above or any one or some of the specific denotations which are comprised by its definitions and are specified above.

A further embodiment of the present invention relates to any of the individual compounds of the formulae I and Ia which are specifically disclosed herein, including the compounds of all examples described below, in the form of the respective free compound as well as in the form of the physiologically acceptable salts thereof in general and, if a specific salt is disclosed herein, in the form of this specific salt, as well as to all tautomeric forms of the free compounds and their salts if tautomeric forms exist. I.e., this embodiment encompasses the physiologically acceptable salts in general of any individual compound specifically disclosed herein, irrespective thereof whether the compound is specifically disclosed as the free compound or as a specific salt. For example, as regards the compound 1-(3-(6-(2-fluorophenyl)pyridin-3-yl)propyl)piperidin-2-one which is specifically disclosed as the free compound, subjects of the present invention are "1-(3-(6-(2-fluorophenyl)pyridin-3-yl)propyl)piperidin-2-one" and "1-(3-(6-(2-fluorophenyl)pyridin-3-yl)propyl)piperidin-2-one or a physiologically acceptable salt thereof". As regards the compound 4-(3-(6-phenylpyridin-3-yl)propyl)thiomorpholin-3-one which is specifically disclosed as its trifluoroacetic acid salt, subjects of the present invention are "4-(3-(6-phenylpyridin-3-yl)propyl)thiomorpholin-3-one", "4-(3-(6-phenylpyridin-3-yl)propyl)thiomorpholin-3-one or a physiologically acceptable salt thereof" and "4-(3-(6-phenylpyridin-3-yl)propyl)thiomorpholin-3-one trifluoroacetic acid salt". Thus, a subject of the present invention is a compound chosen from all individual compounds which are specifically disclosed herein, irrespective thereof whether they are disclosed as the free compound or as a specific salt, including the compounds 1-(3-(6-(2-fluorophenyl)pyridin-3-yl)propyl)-1H-pyridin-2-one, 1-(3-(6-(2-fluorophenyl)pyridin-3-yl)propyl)piperidin-2-one, 4-(3-(6-phenylpyridin-3-yl)propyl)thiomorpholin-3-one, 1-(3-(6-(2-fluorophenyl)pyridin-3-yl)propyl)pyrrolidin-2-one, 1-(3-(6-(2-fluorophenyl)pyridin-3-yl)propyl)piperidine-2,6-dione, 1-(3-(6-(2-fluorophenyl)pyridin-3-yl)propyl)azepan-2-one, 4-(3-(6-(2-chlorophenyl)pyridin-3-yl)propyl)thiomorpholin-3-one, 4-(3-(6-(4-fluorophenyl)pyridin-3-yl)propyl)thiomorpholin-3-one, 4-(3-(6-(2-fluorophenyl)pyridin-3-yl)propyl)thiomorpholin-3-one, 1-(3-(6-(2-fluorophenyl)pyridin-3-yl)propyl)pyrrolidine-2,5-dione, 3-(3-(6-(2-fluorophenyl)pyridin-3-yl)propyl)thiazolidine-2,4-dione, 1-(3-(6-(4-fluorophenyl)pyridin-3-yl)propyl)pyrrolidin-2-one, 1-(3-(6-(4-fluorophenyl)pyridin-3-yl)propyl)pyrrolidine-2,5-dione, 3-(3-(6-(4-fluorophenyl)pyridin-3-yl)propyl)imidazolidine-2,4-dione, 1-(3-(6-(4-fluorophenyl)pyridin-3-yl)propyl)azetidin-2-one, 1-(3-(6-(4-fluorophenyl)pyridin-3-yl)propyl)piperidin-2-one, 1-(3-(6-(4-fluorophenyl)pyridin-3-yl)propyl)azepan-2-one, 4-(3-(6-(2-fluorophenyl)pyridin-3-yl)propyl)-4H-[1,4]thiazin-3-one, 3-(3-(6-(2-fluorophenyl)pyridin-3-yl)propyl)imidazolidine-2,4-dione, 1-(3-(6-(4-fluorophenyl)pyridin-3-yl)propyl)piperidine-2,6-dione, 3-(3-(6-(4-fluorophenyl)pyridin-3-yl)propyl)thiazolidine-2,4-dione, 1-(3-(6-(2-fluorophenyl)pyridin-3-yl)propyl)azetidin-2-one, 1-(3-(6-(4-fluorophenyl)pyridin-3-yl)propyl)-1H-pyridin-2-one, 4-(3-(6-(4-fluorophenyl)pyridin-3-yl)propyl)-4H-[1,4]thiazin-3-one, 1-(2-(6-(2-fluorophenyl)pyridin-3-yloxy)ethyl)piperidin-2-one, 1-(2-(6-(2-fluorophenyl)pyridin-3-yloxy)ethyl)azetidin-2-one, 1-(2-(6-(2-fluorophenyl)pyridin-3-yloxy)ethyl)pyrrolidine-2,5-dione, 3-(2-(4-(4-fluorophenyl)thiazol-2-ylamino)ethyl)imidazolidine-2,4-dione, 3-(2-(6-(2-fluorophenyl)pyridin-3-yloxy)ethyl)imidazolidine-2,4-dione, 1-(2-(5-(2-fluorophenyl)pyridin-2-yloxy)ethyl)pyrrolidin-2-one, 1-(2-(4-(4-fluorophenyl)thiazol-2-ylamino)ethyl)pyrrolidine-2,5-dione,
1-(2-(6-(4-fluorophenyl)pyridin-3-yloxy)ethyl)pyrrole-2,5-dione,
1-(2-(6-(4-fluorophenyl)pyridin-3-yloxy)ethyl)pyrrolidine-2,5-dione,
1-(2-(6-(4-fluorophenyl)pyridin-3-yloxy)ethyl)-1H-pyridin-2-one,
1-(2-(4-(4-fluorophenyl)thiazol-2-ylamino)ethyl)imidazolidin-2-one,
3-(2-(6-(4-fluorophenyl)pyridin-3-yloxy)ethyl)imidazolidine-2,4-dione,
3-(3-(6-(4-fluorophenyl)pyridin-3-yl)propyl)-5,5-dimethylimidazolidine-2,4-dione,
3-(3-(6-(4-fluorophenyl)pyridin-3-yl)propyl)oxazolidin-2-one,
1-(2-(6-(3-chloro-4-fluorophenyl)pyridin-3-yloxy)ethyl)pyrrolidine-2,5-dione,
1-(2-(6-(6-fluoropyridin-3-yl)pyridin-3-yloxy)ethyl)pyrrolidine-2,5-dione,
1-(2-(6-(4-methylthiophen-2-yl)pyridin-3-yloxy)ethyl)pyrrolidine-2,5-dione,
1-(2-(6-(3,4,5-trifluorophenyl)pyridin-3-yloxy)ethyl)pyrrolidine-2,5-dione,
1-(2-(6-(3-trifluoromethoxyphenyl)pyridin-3-yloxy)ethyl)pyrrolidine-2,5-dione,
1-(2-(6-(2-trifluoromethoxyphenyl)pyridin-3-yloxy)ethyl)pyrrolidine-2,5-dione,
1-(2-(6-(6-methoxypyridin-3-yl)pyridin-3-yloxy)ethyl)pyrrolidine-2,5-dione,
1-(2-(6-(pyridin-3-yl)pyridin-3-yloxy)ethyl)pyrrolidine-2,5-dione,
1-(2-(6-(4-trifluoromethoxyphenyl)pyridin-3-yloxy)ethyl)pyrrolidine-2,5-dione,
1-(2-(6-(2,3-dichlorophenyl)pyridin-3-yloxy)ethyl)pyrrolidine-2,5-dione,
1-(2-(6-(2,4-difluorophenyl)pyridin-3-yloxy)ethyl)pyrrolidine-2,5-dione,
1-(2-(6-(3,4-dimethoxyphenyl)pyridin-3-yloxy)ethyl)pyrrolidine-2,5-dione,
1-(2-(6-(4-cyanophenyl)pyridin-3-yloxy)ethyl)pyrrolidine-2,5-dione,
1-(2-(6-(3-cyanophenyl)pyridin-3-yloxy)ethyl)pyrrolidine-2,5-dione,
1-(2-(6-(naphthalen-2-yl)pyridin-3-yloxy)ethyl)pyrrolidine-2,5-dione
1-(2-(6-(naphthalen-1-yl)pyridin-3-yloxy)ethyl)pyrrolidine-2,5-dione,
1-(2-(6-(3-acetylaminophenyl)pyridin-3-yloxy)ethyl)pyrrolidine-2,5-dione,
1-(2-(6-(2-trifluoromethylphenyl)pyridin-3-yloxy)ethyl)pyrrolidine-2,5-dione,
1-(2-(6-(4-trifluoromethylphenyl)pyridin-3-yloxy)ethyl)pyrrolidine-2,5-dione,
1-(2-(6-(3,5-dichlorophenyl)pyridin-3-yloxy)ethyl)pyrrolidine-2,5-dione,
1-(2-(6-(3-trifluoromethylphenyl)pyridin-3-yloxy)ethyl)pyrrolidine-2,5-dione,
1-(2-(6-(3,4-difluorophenyl)pyridin-3-yloxy)ethyl)pyrrolidine-2,5-dione,
1-(2-(6-(3,5-difluorophenyl)pyridin-3-yloxy)ethyl)pyrrolidine-2,5-dione,
1-(2-(6-(4-tert-butylphenyl)pyridin-3-yloxy)ethyl)pyrrolidine-2,5-dione,
1-(2-(6-(4-ethoxyphenyl)pyridin-3-yloxy)ethyl)pyrrolidine-2,5-dione,
1-(2-(6-(2-fluoropyridin-3-yl)pyridin-3-yloxy)ethyl)pyrrolidine-2,5-dione,
1-(2-(6-(2,5-difluorophenyl)pyridin-3-yloxy)ethyl)pyrrolidine-2,5-dione,
1-(2-(6-(4-dimethylaminophenyl)pyridin-3-yloxy)ethyl)pyrrolidine-2,5-dione,
1-(2-(6-(3-chloropyridin-4-yl)pyridin-3-yloxy)ethyl)pyrrolidine-2,5-dione,
1-(2-(6-(5-cyanothiophen-2-yl)pyridin-3-yloxy)ethyl)pyrrolidine-2,5-dione,
1-(2-(6-(3,5-dimethylisoxazol-4-yl)pyridin-3-yloxy)ethyl)pyrrolidine-2,5-dione,
1-(2-(6-(3-fluoropyridin-4-yl)pyridin-3-yloxy)ethyl)pyrrolidine-2,5-dione,
1-(2-(6-(4-fluoro-2-methylphenyl)pyridin-3-yloxy)ethyl)pyrrolidine-2,5-dione,
1-(2-(6-(4-fluoro-3-methylphenyl)pyridin-3-yloxy)ethyl)pyrrolidine-2,5-dione,
1-(2-(6-(pyrimidin-5-yl)pyridin-3-yloxy)ethyl)pyrrolidine-2,5-dione,
4-(3-(6-(4-fluorophenyl)pyridin-3-yl)propylcarbamoyl)butyric acid,
2-(2-(4-(4-fluorophenyl)thiazol-2-ylamino)ethyl)isoindole-1,3-dione,
1-(2-(5-(1-methyl-1H-benzoimidazol-2-yl)pyridin-2-yloxy)ethyl)pyrrolidin-2-one,
N-(2-(4-(4-fluorophenyl)thiazol-2-ylamino)ethyl)acetamide,
2-(2-(6-(2-fluorophenyl)pyridin-3-yloxy)ethyl)isoindole-1,3-dione,
4-chloro-N-(2-(4-(4-fluorophenyl)thiazol-2-ylamino)ethyl)benzamide,
4-aminofurazan-3-carboxylic acid (2-(4-(4-fluorophenyl)thiazol-2-ylamino)ethyl)amide,
N-(2-(4-(4-fluorophenyl)thiazol-2-ylamino)ethyl)isonicotinamide,
N-(2-(6-(2-fluorophenyl)pyridin-3-yloxy)ethyl)acetamide,
N-(2-(6-(2-fluorophenyl)pyridin-3-yloxy)ethyl)benzamide,
cyclopropanecarboxylic acid (2-(6-(2-fluorophenyl)pyridin-3-yloxy)ethyl)amide,
1-(2-(6-(quinolin-8-yl)pyridin-3-yloxy)ethyl)pyrrolidine-2,5-dione,
1-(2-(6-(4-methylsulfonylaminophenyl)pyridin-3-yloxy)ethyl)pyrrolidine-2,5-dione, and
1-(2-(6-(3-methylsulfonylaminophenyl)pyridin-3-yloxy)ethyl)pyrrolidine-2,5-dione,
or a physiologically acceptable salt thereof.

A further subject of the present invention are processes of preparation by which the compounds of the formulae I and Ia or salts thereof are obtainable. There are several ways of preparing the compounds by piecing suitable building blocks together. According to one of the processes, by which compounds of the formulae I and Ia can be synthesized in which the group A denotes —Y—CH$_2$—CH$_2$—, i.e. compounds of the formula Ib in which the groups Het, X, Y, R$^1$, R$^2$ and R$^3$ are defined as in the compounds of the formulae I and Ia, a compound of the formula IV and a compound of the formula V are linked in a standard alkylation reaction.

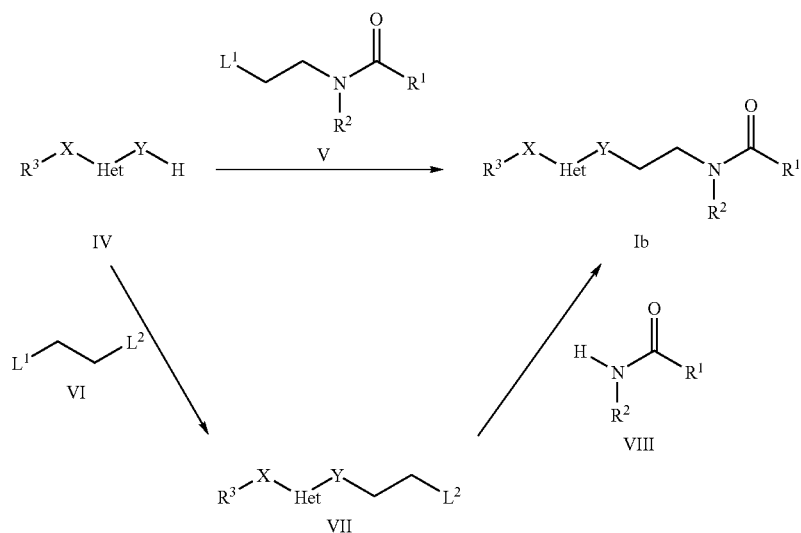

In the compounds of the formulae IV and V the groups Het, X, Y, $R^1$, $R^2$ and $R^3$ are defined as in the compounds of the formulae I and Ia and, in addition, any functional groups can be present in protected form or in the form of precursor groups which are later converted into the desired groups. The compounds of the formulae IV and V can also be employed in the form of salts. The group $L^1$ in the compounds of the formula V is a leaving group which is nucleophilically substitutable by the amino group, hydroxyl group or mercapto group representing the group —Y—H in the compounds of the formula IV. Examples of suitable leaving groups $L^1$ are halogen, in particular chlorine and bromine, and arylsulfonyloxy groups and alkylsulfonyloxy groups such as benzenesulfonyloxy, toluenesulfonyloxy, nitrobenzenesulfonyloxy, methanesulfonyloxy and trifluoromethanesulfonyloxy. When compounds of the formula V containing such leaving groups $L^1$ are employed, for binding the liberated acid of the formula $L^1$-H and/or enhancing the nucleophilicity of the compound of the formula IV in the alkylation reaction it is often advantageous to employ a suitable base such as an amine, for example a tertiary amine like triethylamine, ethyldiisopropylamine, pyridine, an amide salt, for example sodium amide or lithium diisopropylamide, an organometallic compound, for example an organolithium compound like n-butyllithium, an alkali metal or alkaline earth metal hydride, for example lithium hydride, sodium hydride or calcium hydride, an alkali metal or alkaline earth metal hydroxide or quaternary ammonium hydroxide, for example lithium hydroxide, sodium hydroxide, potassium hydroxide, calcium hydroxide, benzyltrimethylammonium hydroxide, an alkali metal or alkaline earth metal alkoxide, for example sodium methoxide, sodium ethoxide, potassium methoxide, potassium ethoxide, potassium tert-butoxide, or another basic alkaline metal or earth alkaline metal compound, for example a carbonate like sodium carbonate, potassium carbonate, cesium carbonate, a hydrogencarbonate like sodium hydrogencarbonate, potassium hydrogencarbonate, or another basic salt, or a mixture of two or more bases. The base can be employed before the actual alkylation reaction is performed in order to convert the compound of the formula IV into its corresponding salt. The reaction of the compounds of the formulae IV and V is usually carried out in an inert solvent, which can be protic or aprotic and aqueous or non-aqueous, such as a hydrocarbon or chlorinated hydrocarbon, for example n-heptane, toluene, xylene, chlorobenzene, dichloromethane, an ether, for example diethyl ether, diisopropyl ether, 1,2-dimethoxyethane (=DME), tetrahydrofuran (=THF), dioxane, an ester, for example ethyl acetate, butyl acetate, an amide, for example N,N-dimethylformamide (=DMF), N-methylpyrrolidin-2-one (=NMP), a nitrile, for example acetonitrile, an alcohol, for example methanol, ethanol, isopropanol, n-butanol, or another solvent, for example water, pyridine, dimethyl sulfoxide (=DMSO), or a mixture of two or more solvents, including a mixture of water and an organic solvent which is miscible or immiscible with water. The reaction of the compounds of the formulae IV and V can be carried out in a wide temperature range. Usually it is advantageous to perform the reaction at temperatures from about −20° C. to about the boiling point of the solvent used, preferably at from about 0° C. to about 100° C. As is usual, the detailed conditions of a specific preparation, including the solvent, the base, the temperature, the order of addition, the molar ratios and other parameters, are routinely chosen by the person skilled in the art in view of the characteristics of the starting compounds and the target compound.

Besides halogen or a sulfonyloxy group, the leaving group $L^1$ can also be a hydroxyl group, for example, and the linking of the compounds of the formulae IV and V be effected under the conditions of the Mitsunobu reaction. In such a reaction a hydroxyl compound is activated by reaction with an azodicarboxylic acid ester like diethyl azodicarboxylate (DEAD) or diisopropyl azodicarboxylate (DIAD) and a phosphane like triphenylphosphane or tributylphosphane, and becomes susceptible to nucleophilic substitution. The reaction can usually be carried under mild conditions in an aprotic solvent like an ether, for example tetrahydrofuran or dioxane, at temperatures from about 0° C. to about room temperature. Details on the Mitsunobu reaction are given, for example, in Mitsunobu, Synthesis (1981) 1.

Instead of reacting the compound of the formula IV with the compound of the formula V and thereby simultaneously introducing the group —$CH_2$—$CH_2$— and the group —N($R^2$)—CO—$R^1$, these two groups can also be introduced stepwise by first reacting a compound of the formula IV with a compound of the formula VI and then reacting the obtained compound of the formula VII, or a compound generated from the compound of the formula VII, with a compound of the formula VIII. In the compounds of the formulae IV, VI, VII and VIII the groups Het, X, Y, $R^1$, $R^2$, $R^3$ and $L^1$ are defined as in the compounds of the formulae I and Ia and the compounds of the formula V and, in addition, any functional groups can be present in protected form or in the form of precursor groups which are later converted into the desired groups. The compounds of the formulae IV, VI and VII can also be employed in the form of salts. The group $L^2$ in the compounds of the formulae VI and VII can be a nucleophilically substitutable leaving group like the group $L^1$ and be defined as the group $L^1$ in the compound of the formula V, and be identical to or different from $L^1$. If $L^2$ is a leaving group, the formation of the desired product of the formula VII in the reaction of the compounds of the formulae IV and VI can be achieved by employing suitable reaction conditions, for example employing an excess of the compound of the formula VI, or by employing a compound of the formula VI which contains two leaving groups $L^1$ and $L^2$ of different reactivity. The group $L^2$ in the compound of the formula VI, instead of being a leaving group, can also be a protected form of a leaving group or a precursor of a leaving group which is converted into a leaving group in the compound of the formula VII. For example, the group $L^2$ in the compound of the formula VI can be a hydroxyl group, or the group $L^2$ in the compound of the formula VI can be an esterified or etherified hydroxyl group which in the compound of the formula VIII is converted into a hydroxyl group, and the hydroxyl group representing the group $L^2$ in the obtained compound of the formula VII can be converted into a halogen atom or a sulfonyloxy group, for example a bromine atom by treatment with hydrogen bromide or phosphorus tribromide or a methanesulfonyloxy group by treatment with methanesulfonyl chloride. Such conversions can be performed under standard conditions known to the skilled person. Another example of such a compound of the formula VI is a 2-halogen-substituted acetic acid ester, for example a 2-bromoacetic acid ($C_1$-$C_4$)-alkyl ester. After alkylation of the compound of the compound of the formula IV with such an ester to give a compound of the formula VII in which the —$CH_2$—$CH_2$-$L^2$ moiety is replaced with a —$CH_2$—CO—O—($C_1$-$C_4$)-alkyl moiety, the ester group can be reduced to a hydroxyl group, for example with a complex hydride reducing agent such as lithium borohydride, to give a compound of the formula VII in which $L^2$ is hydroxyl, which can then be converted into a compound of the formula VII in which $L^2$ is methanesulfonyloxy, for example. All the above explanations on the reaction of the compounds of the formulae IV and V, for example with respect to bases which may be added, apply correspondingly to the reactions of the compounds of the formulae IV and VI and the reaction of the compounds of the formulae VII and VIII.

Instead of introducing the group Y by means of the same starting compound which introduces the $R^3$—X-Het-moiety, the group Y can also be introduced by means of the starting compound which introduces the —N($R^2$)—CO—$R^1$ moiety, and a compound of the formula Ib prepared by reaction of suitable compounds of the formulae IX and X.

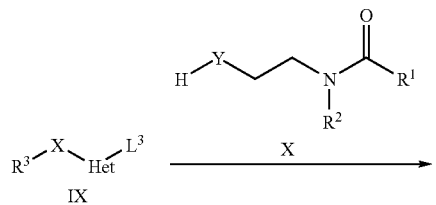

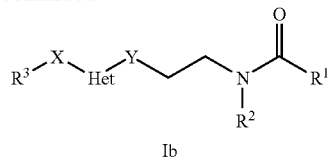

In the compounds of the formulae IX and X the groups Het, X, Y, $R^1$, $R^2$ and $R^3$ are defined as in the compounds of the formulae I and Ia and, in addition, any functional groups can be present in protected form or in the form of precursor groups which are later converted into the desired groups. The group $L^3$ in the compounds of the formula IX is a leaving group which can be replaced with the group Y in a nucleophilic aromatic substitution reaction. Examples of leaving groups $L^3$ in a compound of the formula IX which can undergo such a reaction, are halogen, for example chlorine, bromine or iodine, and sulfonyloxy groups such as trifluoromethanesulfonyloxy. The compounds of the formulae IX and X can also be employed in the form of salts. All the above explanations on the reaction of the compounds of the formulae IV and V, for example with respect to bases which may be added, apply to the reaction of the compounds of the formulae IX and X correspondingly.

The starting compounds of the formulae IV, V, VI, VIII, IX and X, as well as other starting compounds for the preparation of the compounds of the invention discussed herein, are commercially available or can be prepared according to, or analogously to, procedures which are described in the literature and familiar to the person skilled in the art. Compounds of the formulae IV and IX, for example, in which the group X is O, S, NH or N(($C_1$-$C_4$)-alkyl), can be obtained in a nucleophilic aromatic substitution reaction, similarly to the reaction of the compounds of the formulae IX and X, from a respective compound of the formula $R^3$—X—H and a suitable heteroaromatic compound containing a leaving group. Compounds of the formulae IV and IX in which the group X is $CH_2$ can be obtained by reaction of a metallated heteroaromatic compound comprising the group Het with an alkylating agent which introduces the $R^3$—$CH_2$-moiety, or by reduction of a compound which contains a $R^3$—CO-Het- or $R^3$—CH(OH)-Het-moiety which can in turn be obtained by an acylation reaction or by reaction of an aldehyde with a metallated heteroaromatic compound. Compounds of the formula IV and IX in which the group X is a direct bond, can be obtained in a transition metal-catalyzed Suzuki coupling reaction from a halogen-substituted heteroaromatic compound comprising the group Het and a boronic acid derivative. Compounds of the formulae V and X can be obtained by acylating amines of the formulae $L^1$-$CH_2$—$CH_2$—N($R^2$)—H and H—Y—$CH_2$—$CH_2$—N($R^2$)—H or alkylating amides of the formula VIII and optionally modifying a group in a desired manner, for example converting a hydroxyl group representing the group H—Y— into a halogen atom or a sulfonyloxy group representing the group $L^1$, such as a bromine atom by treatment with hydrogen bromide or phosphorus tribromide or a methanesulfonyloxy group by treatment with methanesulfonyl chloride under standard conditions (cf., for example, the preparation of methanesulfonic acid 2-(2,5-dioxopyrrolidin-1-yl)ethyl ester from methanesulfonyl chloride and 1-(2-hydroxyethyl)pyrrolidine-2,5-dione described in WO 2004/089903). Compounds of the formula VIII can be obtained by acylation of amines of the formula $R^2$—$NH_2$ or, in case $R^1$ and $R^2$ together with the N—CO group which carries them form a ring, from suitable bifunctional starting compounds such as from amino-substituted carboxylic acids by cyclization or from dicarboxylic acids by conversion into the imides, for example.

Compounds of the formulae I and Ia in which the group A denotes —CH$_2$—CH$_2$— or —CH$_2$—CH$_2$—CH$_2$—, i.e. compounds of the formula Ic in which the number p is 0 or 1 and all other groups are defined as in the compounds of the formulae I and Ia, can be prepared by reacting a compound of the formula IX with an amide of the formula XI or XIII which comprises a terminal alkenyl or alkynyl moiety, respectively, in the unsaturated substituent on the nitrogen atom to give an intermediate of the formula XII or XIV which can then be converted into a compound of the formula Ic by catalytic hydrogenation, for example in the presence of a palladium catalyst.

CH$_2$— or —CH$_2$—CH$_2$—CH$_2$—, i.e. compounds of the formula Ic in which the number p is 0 or 1 and the other groups are defined as in the compounds of the formulae I and Ia, starts from heteroaromatic aldehydes of the formula XV in which the carbon chain can be elongated to give the hydroxyalkyl compounds of the formula XVI which, after conversion of the hydroxyl group into a leaving group to give the compounds of the formula XVII, can be used for the alkylation of compounds of the formula VIII to give compounds of the formula Ic.

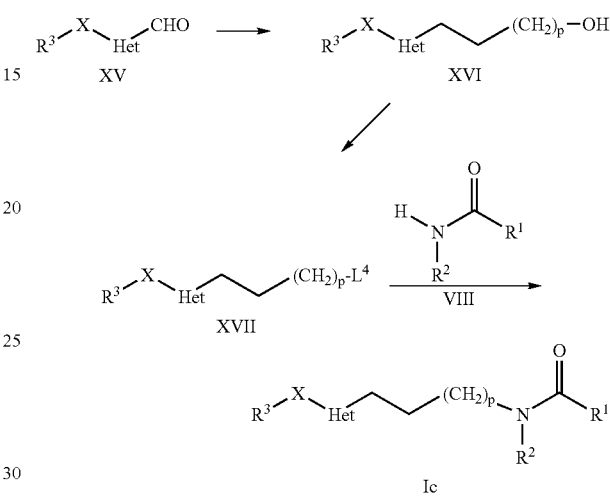

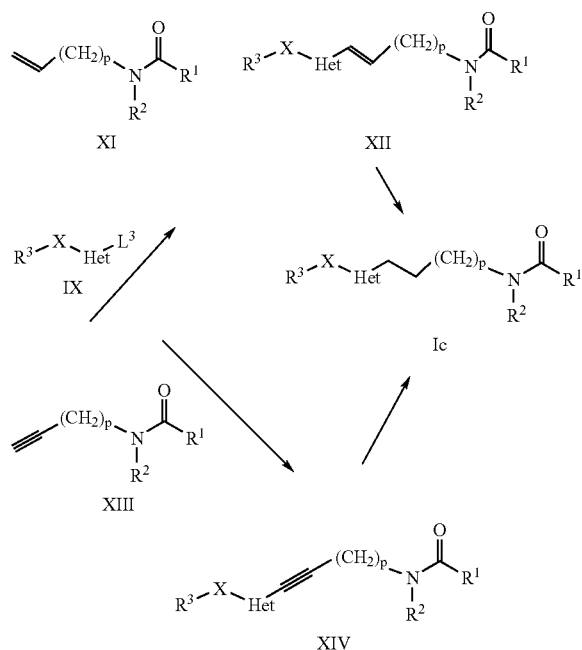

In the compounds of the formulae IX and XI to XIV the groups Het, X, R$^1$, R$^2$ and R$^3$ are defined as in the compounds of the formulae I and Ia and, in addition, any functional groups can be present in protected form or in the form of precursor groups which are later converted into the desired groups. The number p in the compounds of the formulae XI to XIV is 0 or 1. Like the —CH$_2$—CH$_2$—CH$_2$— and —CH$_2$—CH$_2$— groups representing the group A in the compounds of the formulae I and Ia, the alkenyl and alkynyl group in the compounds of the formulae XI to XIV can optionally be substituted by suitable substituents, for example alkyl substituents. The group L$^3$ in the compounds of the formula IX is a leaving group such as halogen, for example chlorine, bromine or iodine, or a sulfonyloxy group, for example trifluoromethanesulfonyloxy, as explained above. The reaction of a compound of the formula IX with a compound of the formula XI or XII is carried out under the conditions of the well-known Heck reaction and Sonogashira reaction, respectively, in the presence of a transition metal catalyst such as a palladium catalyst and, in the case of the Sonogashira reaction, a copper co-catalyst such as copper iodide (cf. de Meijere et al., Angew. Chem. Int. Ed. 33 (1994) 2379).

A further process for the preparation of compounds of the formulae I and Ia in which the group A denotes —CH$_2$—

In the compounds of the formulae VIII and XV to XVII the groups Het, X, R$^1$, R$^2$ and R$^3$ are defined as in the compounds of the formulae I and Ia and, in addition, any functional groups can be present in protected form or in the form of precursor groups which are later converted into the desired groups. The number p in the compounds of the formulae XVI and XVII is 0 or 1. Like the —CH$_2$—CH$_2$—CH$_2$— and —CH$_2$—CH$_2$— groups representing the group A in the compounds of the formulae I and Ia, the carbon chains in the compounds of the formulae XV to XVII can optionally be substituted by suitable substituents, for example alkyl substituents. In case the carbon atom adjacent to the group Het carries an alkyl group, the starting compound of the formula XV can thus also be a ketone instead of an aldehyde. The group L$^4$ in the compounds of the formula XVII is a nucleophilically substitutable leaving group. Similarly as explained above with respect to the leaving group L$^1$, examples of suitable leaving groups L$^4$ are halogen, in particular chlorine and bromine, and arylsulfonyloxy groups and alkylsulfonyloxy groups such as benzenesulfonyloxy, toluenesulfonyloxy, nitrobenzenesulfonyloxy, methanesulfonyloxy and trifluoromethanesulfonyloxy.

For elongating the carbon chain by two carbon atoms, the compound of the formula XV can be condensed under the conditions of the Knoevenagel reaction with a malonic acid derivative, or under the conditions of the Wittig-Horner reaction with a di((C$_1$-C$_4$)-alkyl) ((C$_1$-C$_4$)-alkyloxy)carbonylmethylphosphonate, for example. In the intermediate heteroaromatic cinnamic acid derivative of the formula R$^3$—X-Het-CH=CH—COOR$^{30}$, in which R$^{30}$ can be (C$_1$-C$_4$)-alkyl or hydrogen, the —CH=CH— moiety can be converted into a —CH$_2$—CH$_2$— moiety by catalytic hydrogenation, for example in the presence of a palladium catalyst, and the COOR$^{30}$ moiety reduced to a —CH$_2$—OH moiety, for example by reduction with a complex borohydride or aluminum hydride such as lithium borohydride, to give a compound of the formula XVI in which p is 1. For elongating the carbon chain by one carbon atom, a compound of the formula XV can be condensed under the conditions of the Wittig reaction with a methoxymethyltriphenylphosphonium salt, for example, and in the intermediate compound of the formula $R^3$—X-Het-$CH=CH-OCH_3$ the vinyl ether moiety —$CH=CH-OCH_3$ can be hydrolyzed under acidic conditions to give the aldehyde moiety —$CH_2$—CHO which can be reduced to a —$CH_2$—$CH_2$—OH moiety by means of a complex borohydride or by catalytic hydrogenation to give a compound of the formula XVI in which p is 0. Similarly as outlined above with respect to the compounds of the formula V and VII, the conversion of the hydroxyalkyl compound of the formula XVI into the compound of the formula XVII can be accomplished by means of a halogenating agent such as thionyl chloride, phosphorus tribromide or hydrogen bromide in case $L^4$ is halogen, or a sulfonyl chloride or a sulfonic acid anhydride such as methanesulfonyl chloride or trifluoromethanesulfonyl anhydride, for example, in case $L^4$ is a sulfonyloxy group. All the above explanations on the reaction of the compounds of the formulae IV and V, for example with respect to bases which may be added, apply correspondingly to the reaction of the compounds of the formulae XVII and VIII. The compounds of the formulae XVII and VII can also be employed in the form of their salts.

Instead of starting in the preparation of a target compound of the formula I or Ia from a compound which already comprises all the groups $R^3$, X and Het, such as a compound of the formula IV or IX or XVI, it is also possible to start from a compound which only comprises the group Het or the groups X and Het, for example, and to introduce the group $R^3$ or the moiety $R^3$—X— in a later step, or in the last step of the reaction sequence, after having assembled the —X-Het-A-N($R^2$)—CO—$R^1$ moiety or the -Het-A-N($R^2$)—CO—$R^1$ moiety. Thus, for example, when preparing a compound of the formula Ib which is defined as indicated above, instead of reacting a compound of the formula IV with a compound of the formula V, also a compound of the formula XVIII can be reacted with a compound of the formula V and the resulting intermediate of the formula XIX reacted with a compound of the formula XX which introduces the $R^3$—X— moiety.

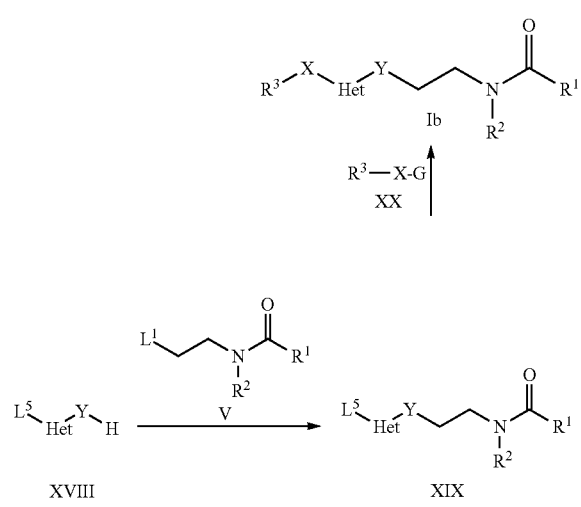

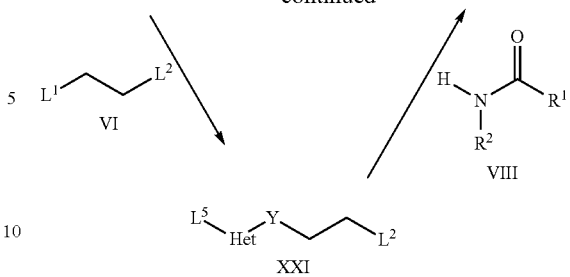

In the compounds of the formulae V, XVIII, XIX and XX the groups Het, X, Y, $R^1$, $R^2$ and $R^3$ are defined as in the compounds of the formulae I and Ia and, in addition, any functional groups can be present in protected form or in the form of precursor groups which are later converted into the desired groups. The compounds can also be employed in the form of their salts. The leaving group $L^1$ in the compounds of the formula V is defined as indicated above. Similarly as explained above with respect to the compounds of the formulae IV and V, the reaction of the compounds of the formulae XVIII and V is preferably carried out in the presence of a base. All the above explanations on the reaction of the compounds of the formulae IV and V correspondingly apply to the reaction of the compounds of the formulae XVIII and V. The group $L^5$ in the compounds of the formulae XVIII and XIX is a leaving group which can be replaced with the group $R^3$—X— in a nucleophilic aromatic substitution reaction or a reaction of another type as it is performed when reacting the compounds of the formulae XIX and XX. Examples of suitable leaving groups $L^5$ in the compounds of the formulae XVIII and XIX are halogen, in particular chlorine, bromine and iodine, and sulfonyloxy groups such as trifluoromethanesulfonyloxy. The group G in the compounds of the formula XX can be hydrogen in case the group X is O, S, NH or N(($C_1$-$C_4$)-alkyl). In such case the nucleophilic aromatic substitution reaction between the compounds of the formulae XIX and XX can be carried out as indicated above with respect to the reaction of the compounds IX and X. In case the group X is a direct bond and the group G thus is attached directly to the group $R^3$ via a single bond, the group G can be a boronic acid derivative, for example a boronic acid group, and the compound of the formula XX thus be a compound of the formula $R^3$—B(OH)$_2$ in which $R^3$ is defined as in the compounds of the formulae I and Ia and, in addition, any functional groups can be present in protected form or in the form of precursor groups. The reaction of the boronic acid derivative with a compound of the formula XIX to give a compound of the formula Ib, in which X is a direct bond, can be carried out under the conditions of the well known Suzuki coupling, or Suzuki-Miyaura coupling, in the presence of a transition metal catalyst such as a palladium catalyst, for example palladium acetate or tetrakis(triphenylphosphane) palladium, in an aqueous or non-aqueous solvent. Details on such coupling reactions of boronic acid derivatives, which can advantageously be used also in other processes for the preparation of the compounds of the invention, and intermediates therefor are explained in Kotha et al., Tetrahedron 58 (2002) 9633, Miyaura, Topics in Current Chemistry 219 (2002) 11, or Walker et al., Angew. Chem. Ind. Ed. 43 (2004) 1871, for example.

In a similar manner as described above, instead of reacting compounds of the formulae IV and VI and reacting the resulting compound of the formula VII with a compound of the formula VIII, compounds of formula Ib can also be prepared by reacting compounds of the formulae XVIII and VI, reacting the resulting compound of the formula XXI with a compound of the formula VIII to give a compound of the formula XIX, and finally introducing the group $R^3$—X— into the latter compound by reacting it with a compound of the formula XX. The groups Het, Y and $L^2$ in the compounds of the formula XXI are defined as in the compounds of the formula VII, the group $L^5$ in the compounds of the formula XXI is defined as the group $L^5$ in the compounds of the formulae XVIII and XIX. With respect to the other compounds involved in this process, including examples of compounds of the formula VI such as 2-bromoacetic acid esters, and suitable reaction conditions the above statements apply correspondingly.

Just so, instead of reacting compounds of the formulae IX and X, compounds of the formulae XXII and X can be reacted to give a compound of the formula XXIII which can then be reacted with a compound of the formula XX to give a compound of the formula Ib.

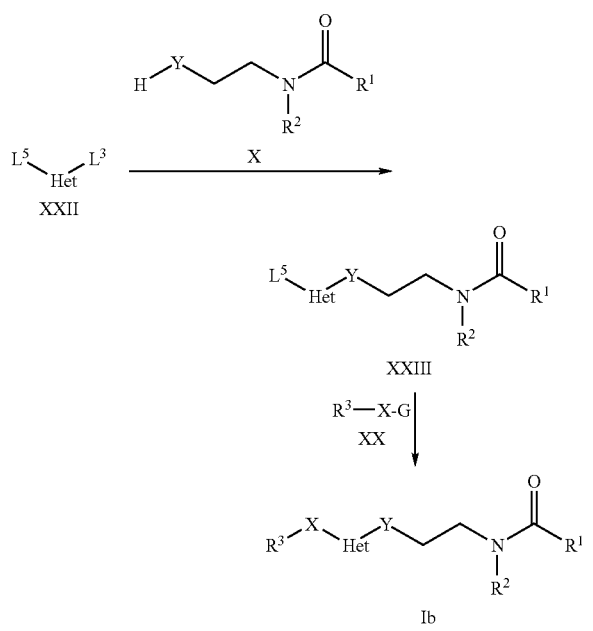

The group $L^5$ in the compounds of the formulae XXII and XXIII can be a nucleophilically substitutable leaving group like the group $L^3$ and defined as the group $L^3$, i.e. be a halogen atom, for example chlorine, bromine or fluorine, or a sulfonyloxy group such as trifluoromethanesulfonyloxy, for example, and be identical to or different from $L^3$. If $L^5$ is a leaving group, the formation of the desired product of the formula XXIII in the reaction of the compounds of the formulae XXII and X can be achieved by employing suitable reaction conditions, or by employing a compound of the formula XXII which contains two leaving groups $L^3$ and $L^5$ of different reactivity, or by taking advantage of different reactivities of leaving groups which are present in different positions of the group Het in case $L^3$ and $L^5$ are identical. The latter situation applies to a compound of the formula XXII such as 2,5-dibromopyridine, for example, in which the bromine atom in the 2-position is more reactive than the bromine atom in the 5-position and which will yield a compound of the formula XXIII containing a 5-bromopyridin-2-yl moiety in which the bromine atom in the 5-position can then be replaced with the group $R^3$—X— (cf. Tilley et al., J. Org. Chem. 53 (1988) 386). The group $L^5$ in the compound of the formula XXII, instead of being a leaving group, can also be a protected form of a leaving group or a precursor of a leaving group which is converted into a leaving group in the compound of the formula XXIII. With respect to the other groups in the compounds of the formulae XXII and XXIII and the other compounds involved in this process as well as suitable reaction conditions the statements on the above-discussed processes apply correspondingly. The compounds can also be employed in the form of their salts.

Like in the preparation of compounds of the formulae I and Ia which contain a group Y within the group A, just so in the preparation of compounds in which the group A is —CH$_2$—CH$_2$— or —CH$_2$—CH$_2$—CH$_2$— the group $R^3$ or the group $R^3$—X— can be introduced in a later step, or in the last step of the reaction sequence, after having assembled the -Het-A-N($R^2$)—CO—$R^1$ moiety or the —X-Het-A-N($R^2$)—CO—$R^1$ moiety. Accordingly, instead of reacting a compound of the formula IX with a compound of the formulae XI or XIII, just so a compound of the formula XXII can be reacted with a compound of the formulae XI or XII to give an analog of the compound of the formulae XIII or XIV in which the group $R^3$—X— is replaced with the group $L^5$, in the latter compounds the double bond or triple bond can be hydrogenated, and the resulting analog of the compound of the formula Ic in which the group $R^3$—X— is replaced with the group $L^5$, can be reacted with a compound of the formula XX to give a compound of the formula Ic. The above-discussed preparation of compounds of the formula Ic from heteroaromatic aldehydes of the formula XV can accordingly be modified to start from an heteroaromatic aldehyde of the formula XXIV,

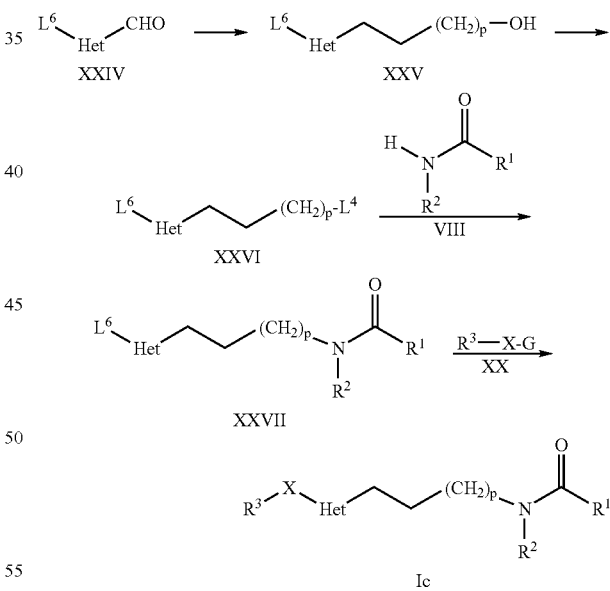

which, via the compounds of the formulae XXV, XXVI and XXVII, can be converted into a compound of the formula Ic. The group $L^6$ in the compounds of the formulae XXIV to XXVII is a leaving group such as halogen, in particular chlorine, bromine or iodine, or a sulfonyloxy group, for example a trifluoromethanesulfonyloxy group, which in the final step of the reaction sequence can be replaced with the group $R^3$—X— introduced by the compound of the formula XX. With respect to the other groups in the compounds of the formulae XXIV to XXVII and the other compounds involved in this process, as well as with respect to reaction conditions and examples of reactions for elongating the carbon chain, the above statements all apply correspondingly. Taking the preparation of a compound of the formula Ic in which the number p is 1 as an example, more specifically a compound of the formula XXIV in which $L^6$ can be a bromine atom, for example, can be reacted in a Wittig-Horner reaction with a di(($C_1$-$C_4$)-alkyl) (($C_1$-$C_4$)-alkyloxy)carbonylmethylphosphonate, for example, to give an intermediate heteroaromatic cinnamic acid derivative of the formula $L^6$-Het-CH=CH—$COOR^{30}$, in which $R^{30}$ can be ($C_1$-$C_4$)-alkyl, and which can be converted by catalytic hydrogenation into an intermediate of the formula $L^6$-Het-$CH_2$—$CH_2$—$COOR^{30}$ in which $R^{30}$ can be ($C_1$-$C_4$)-alkyl. In the latter compound the ester group can be reduced to an alcohol group, for example by treatment with lithium borohydride, to give a compound of the formula XXV in which the number p is 1 and which can be converted into a compound of the formula XXVI in which the number p is 1 and the group $L^4$ is a bromine atom or a methanesulfonyloxy group, for example, by treatment with hydrogen bromide or with methanesulfonyl chloride, respectively. The compound of the formula XXVI can be reacted with a compound of the formula VIII, for example in the presence of sodium hydride, to give a compound of the formula XXVII in which the number p is 1 and in which the group $L^6$, for example a bromine atom, can be replaced with the group $R^3$—X— by reaction with a compound of the formula XX, for example by reaction with a boronic acid in the presence of palladium catalyst in case the group X is a direct bond. Instead of introducing the group $R^3$—X— in the last step of preparation of the compound of the invention, it can also be introduced into any prior intermediate in the course of the synthesis. In the synthesis of compounds of the formula Ic in which the number p is 1, for example, the compound of the formula $L^6$-Het-$CH_2$—$CH_2$—$COOR^{30}$, in which $R^{30}$ can be ($C_1$-$C_4$)-alkyl, can be reacted with a compound of the formula XX to give a compound of the formula $R^3$—X-Het-$CH_2$—$CH_2$—$COOR^{30}$, in which $R^{30}$ can be ($C_1$-$C_4$)-alkyl, and in which the ester group can be reduced to an alcohol group to give a compound of the formula $R^3$—X-Het-$CH_2$—$CH_2$—$CH_2OH$ which, after conversion of the hydroxy group into a leaving group such as the group $L^4$ in the compounds of the formula XXVI, can then be reacted with a compound of the formula VIII. Such variations of the synthetic strategies outlined above are familiar to the person skilled in the art and allow to adapt the preparation of a compound of the formulae I or Ia to the particulars of the specific case.

Further synthetic strategies for the preparation of compounds of the formulae I and Ia include the assembly of the group Het in a ring-forming reaction from starting compounds which can contain the groups $R^3$—X— and -A-N($R^2$)—CO—$R^1$ or part of these groups or protected forms or precursors thereof which are then modified in subsequent reaction steps. For example, compounds of the formulae I and Ia in which the group Het is a thiazole ring, the group X is a direct bond and the group A is the group —NH—$CH_2$—$CH_2$—, i.e. compounds of the formula Id in which the groups $R^1$, $R^2$ and $R^3$ are defined as indicated above with respect to the compounds of the formulae I and Ia, can be prepared by reacting a 2-bromo-1-$R^3$-ethanone of the formula XXVIII, in which the $CH_2$ group can optionally be substituted by a suitable substituent, for example an alkyl substituent, with a thiocyanate, for example an alkali metal thiocyanate such as sodium thiocyanate or potassium thiocyanate, to give a 2-thiocyanato-1—$R^3$-ethanone which can also be isolated if desired, and with an N-(2-aminoethyl)amide of the formula Xa.

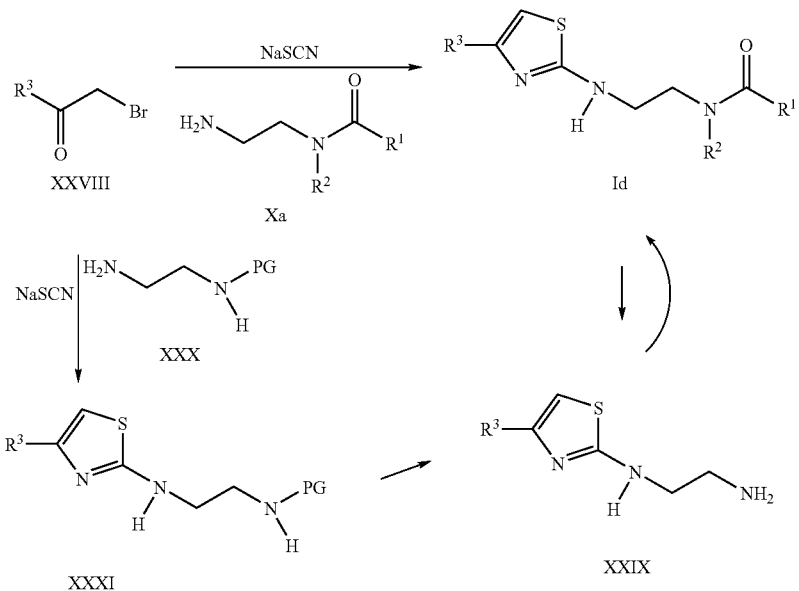

The groups $R^1$ to $R^3$ in the compounds of the formulae Xa and XXVIII are defined as in the compounds of the formulae I and Ia and, in addition, any functional groups can be present in protected form or in the form of precursor groups which are later converted into the desired groups. The reaction of a compound of the formula XXVIII with a thiocyanate and a compound of the formula Xa is generally carried out in a solvent, for example an alcohol such as methanol or ethanol, at elevated temperatures, for example at temperatures from about 40° C. to about 80° C., for example at about 50° C. The NH group attached to the thiazole ring in the compounds of the formula Id and, in general, an NH group representing the group Y in a compound of the formulae I and Ia, can further be modified, for example by treatment with an acylating agent such as a carboxylic acid chloride or anhydride to give a compound of the formulae I or Ia in which the group Y is the group $NR^{11}$ and $R^{11}$ is an acyl group. Compounds of the formulae I and Ia in which the group Y is the group $NR^{11}$ and $R^{11}$ is another group than hydrogen and an acyl group, can be prepared according to the process described afore by employing an analog of the compound of the formula Xa which contains a respective group $R^{11}HN$— instead of the group $H_2N$—.

The amide moiety —$N(R^2)$—CO—$R^1$ in the compounds of the formula Id, as well as in compounds of the formulae I and Ia as defined above in general, can be hydrolyzed under standard conditions to give an amino compound of the formula XXIX in which the group $R^3$ is defined as in the compounds of the formulae I and Ia and, in addition, any functional groups can be present in protected form or in the form of precursor groups, or, depending on the meaning of the group $R^2$ in the compounds of the formula Id, to give an analog of the compound of the formula XXIX which contains a group —$NHR^2$ instead of the —$NH_2$ group, which amino compounds can again be converted into further compounds of the formula Id and thus are valuable intermediate compounds. Such hydrolysis can be carried out by treating a compound of the formula Id or a suitable compound of the formulae I or Ia, for example a compound in which $R^1$ is a methyl group and $R^2$ is hydrogen or more generally a compound of the formula $R^3$—X-Het-A-$NH_2$ which is acylated on the $NH_2$ group and in which $R^3$, X, Het and A are defined as above, with a dilute acid, for example hydrochloric acid, or an alkali metal hydroxide, for example a sodium hydroxide solution. In case $R^1$ and $R^2$, together with the N—CO group which carries them, in the compound of the formula Id or the compound of the formulae I or Ia or more generally in the acylated derivative of the compound of the formula $R^3$—X-Het-A-$NH_2$, form a 1,3-dioxoisoindol-2-yl group (=phthalimido group), the conversion into the compound of the formula Id or into the compound of the formula $R^3$—X-Het-A-$NH_2$ can conveniently be performed by treatment with hydrazine, for example in a solvent such as ethanol under reflux, i.e. analogously to the well known Gabriel synthesis of amines. Compounds of the formula XXIX can furthermore be prepared by reacting a compound of the formula XXVIII as outlined above with a thiocyanate, for example sodium thiocyanate, and a protected 1,2-diaminoethane of the formula XXX to give a compound of the formula XXXI in which the group $R^3$ is defined as in the compounds of the formulae I and Ia and, in addition, any functional groups can be present in protected form or in the form of precursor groups, and in which the amino group is deprotected under standard conditions to give a compound of the formula XXIX. The amino-protecting group PG can be an acyl group or an alkyloxycarbonyl group, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, for example.

The conversion of compounds of the formula XXIX into compounds of the formula Id, or in general of compounds of the formula $R^3$—X-Het-A-$NH_2$ into compounds of the formulae I and Ia, can be carried out according to standard procedures. For example, for the introduction of an acyl group of the formula $R^1$—CO— the amine can be reacted with a carboxylic acid chloride of the formula $R^1$—CO—Cl or an anhydride of the formula $(R^1$—CO$)_2$O, or with a carboxylic acid of the formula $R^1$—COOH by means of a activating reagent or coupling reagent as are commonly used in the preparation of amides. Suitable such reagents include carbodiimides such as N,N'-dicyclohexylcarbodiimide (=DCC) or diisopropylcarbodiimide (=DIC), O-((cyano(ethoxycarbonyl)methylene)amino)-1,1,3,3-tetramethyluronium tetrafluoroborate (=TOTU), N,N,N',N'-tetramethyl-O-(7-azabenzotriazol-1-yl)uronium hexafluorophosphate (=HATU), propanephosphonic acid anhydride (PPA), N,N'-carbonyldiimidazole (CDI), and chloroformic acid alkyl esters such as ethyl chloroformate or isobutyl chloroformate. The acylation is generally carried in a solvent such as, for example, toluene, dichloromethane, THF, dioxane, DMF, NMP, in the presence of a base such as, for example, triethylamine, ethyldiisopropylamine, sodium carbonate, at a temperature from about 0° C. to about 80° C., for example at room temperature. The $NH_2$ group in the compounds of the formula XXIX, or in general in compounds of the formula $R^3$—X-Het-A-$NH_2$, can also be incorporated into a ring, as can be formed in the compounds of the formulae I and Ia by $R^1$ and $R^2$ together with the N—CO group which carries them, for example by reaction with an ω-halogen-substituted alkanecarboxylic acid derivative such as a 4-chlorobutyric acid derivative to give a 2-oxopyrrolidin-1-yl ring system or a 5-chloropentanoic acid derivative to give a 2-oxopiperidin-1-yl ring system, or an α,ω-dicarboxylic acid derivative such as succinic anhydride or phthalic anhydride to give a 2,5-dioxopyrrolidin-1-yl ring system or a 1,3-dioxoisoindol-2-yl ring system, respectively.

Further compounds of the formulae I and Ia can be obtained from suitable compounds prepared according to the above-described processes by functionalization or modification of contained functional groups according standard procedures, for example by esterification, amidation, hydrolysis, etherification, alkylation, acylation, sulfonylation, reduction, oxidation, conversion into salts, and others.

All reactions used in the above-described syntheses of the compounds of the formulae I and Ia are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. As already indicated above, depending on the circumstances of the individual case, in order to avoid an unwanted course of a reaction or side reactions during the synthesis of a compound, it can generally be necessary or advantageous to temporarily block functional groups by introducing protective groups and deprotect them at a later stage of the synthesis, or introduce functional groups in the form of precursor groups which later are converted into the desired functional groups. As a further example of protecting groups, besides the above-mentioned amino-protecting groups, ester protecting groups of carboxylic acid groups may be mentioned, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person. If desired, the obtained compounds of formulae I and Ia, as well as any intermediate compounds, can be purified by customary purification procedures, for example by recrystallization or chromatography.

The compounds of the formulae I and Ia are useful pharmacologically active, or pharmaceutically active compounds which modulate the expression of endothelial NO synthase, and more specifically upregulate, or stimulate, the expression, or transcription, of endothelial NO synthase, and which can be employed as pharmaceuticals, or active ingredients of medicaments, for the treatment of various diseases. In the context of the present invention, treatment is understood as comprising both therapy, including alleviation and cure, of diseases and disease symptoms and prevention and prophylaxis of diseases and disease symptoms, such as, for example, the prevention of the appearance of asthmatic disease symptoms or the prevention of myocardial infarction or of myocardial reinfarction in affected patients. The diseases or disease symptoms can be acute or chronic. Diseases which can be treated with the compounds of the formulae I and Ia include, for example, cardiovascular diseases like stable and unstable angina pectoris, coronary heart disease, coronary artery disease, Prinzmetal angina (spasm), acute coronary syndrome, cardiac insufficiency, heart failure, myocardial infarction, stroke, thrombosis, peripheral artery occlusive disease (=PAOD), endothelial dysfunction, atherosclerosis, restenosis, endothel damage after PTCA (=percutaneous transluminal coronary angioplasty), hypertension including essential hypertension, pulmonary hypertension and secondary hypertension (renovascular hypertension, chronic glomerulonephritis), erectile dysfunction, and ventricular arrhythmia. Further, the compounds of the formulae I and Ia lower the cardiovascular risk of postmenopausal women or after intake of contraceptives. Compounds of the formulae I and Ia can additionally be used in the treatment, including therapy and prevention, of diabetes and diabetes complications such as nephropathy or retinopathy, angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

The compounds of the formulae I and Ia can be used in combination with other pharmacologically active compounds or pharmaceuticals, preferably with compounds which are able to enhance the effect of the compounds according to the formulae I and Ia. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formulae I and Ia and their physiologically acceptable salts, optionally in combination with other pharmacologically active compounds, can be administered to animals, preferably to mammals, and in particular to humans, as pharmaceuticals by themselves, in mixtures with one another, or in the form of pharmaceutical compositions. Further subjects of the present invention therefore also are the compounds of the formulae I and Ia and their physiologically acceptable salts for use as pharmaceuticals, their use as modulating agents, and more specifically as stimulating agents or upregulating agents, of the expression or transcription of endothelial NO synthase, for example in conditions in which an increased expression of said enzyme or an increased NO level or the normalization of a decreased NO level in a patient is desired, and in particular their use in the treatment, including therapy and prevention, of the above-mentioned diseases or syndromes, as well as their use for the preparation or manufacture of medicaments for these purposes. Furthermore, a subject of the present invention are pharmaceutical compositions, or pharmaceutical preparations, which comprise an effective dose of at least one compound of the formulae I or Ia and/or a physiologically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formulae I or Ia and/or its physiologically acceptable salts present in the pharmaceutical compositions normally ranges from about 0.2 to about 800 mg, preferably from about 0.5 to about 500 mg, in particular from about 1 to about 200 mg, per dose, but depending on the type of the pharmaceutical composition it may also be higher. The pharmaceutical compositions usually comprise from about 0.5 to about 90 percent by weight of the compounds of the formulae I or Ia and/or their physiologically acceptable salts. The production of the pharmaceutical compositions can be carried out in a manner known per se. To this end, one or more compounds of the formulae I or Ia and/or their physiologically acceptable salts together with one or more solid or liquid pharmaceutical carrier substances (or vehicles) and/or additives (or auxiliary substances) and, if a combination medicament is desired, other pharmacologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formulae I and Ia and their physiologically acceptable salts and to use the resulting lyophilisates, for example, for preparing compositions for injection or infusion. Suitable carriers for microcapsules, implants or rods are, for example, copolymers of glycolic acid and lactic acid. Besides the compound or compounds according to the invention and carrier substances, the pharmaceutical compositions can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formulae I or Ia to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formulae I or Ia. In general, a daily dose from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results.

The daily dose can be administered in a single dose or, in particular when larger amounts are administered, divided into several, for example two, three or four individual doses. In some cases, depending on the individual response, it may be necessary to deviate upwards or downwards from the given daily dose.

The compounds of the formulae I and Ia can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example further pharmacologically active compounds.

EXAMPLES

Compounds containing a basic group which were purified by preparative HPLC using an eluent which contained trifluoroacetic acid, were in part obtained in the form of acid addition salts with trifluoroacetic acid (TFA) which is not depicted in the formulae in the examples. The compounds were characterized by analytical high pressure liquid chromatography (HPLC) and/or mass spectrometry (MS) and/or nuclear magnetic resonance spectrometry (NMR). The MS data were obtained by electron spray ionization (ESI). The HPLC conditions were as follows.

Method HPLC A (LC/MS): Column: YMC J'sphere 33×2 mm; 4μ. Flow rate: 1 ml/min. Eluent A1: water containing 0.1% TFA. Eluent A2: acetonitrile containing 0.1% TFA. Gradient: from 95% eluent A1+5% eluent A2 to 5% eluent A1+95% eluent A2 in 3.7 min.

Example 1

1-(3-(6-(2-Fluorophenyl)pyridin-3-yl)propyl)-1H-pyridin-2-one

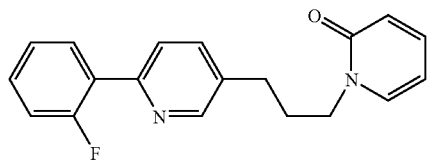 [SMILES: O=c1ccccn1CCCc1ccc(-c2ccccc2F)nc1]

a) 3-(6-(2-Fluorophenyl)pyridin-3-yl)propionic acid ethyl ester

A mixture of 1000 mg (3.87 mmol) of 3-(6-bromopyridin-3-yl)propionic acid ethyl ester, 596.3 mg (4.26 mmol) of 2-fluorophenylboronic acid, 43.5 mg (0.19 mmol) of palladium acetate, 101.6 mg (0.38 mmol) of triphenylphosphane, 3.88 ml of a 1M sodium carbonate solution, 23 ml of toluene and 6 ml of ethanol was heated under reflux for 5 h and, after cooling, poured into water. The resulting mixture was extracted with ethyl acetate. The organic phase was separated and concentrated, and the residue was purified by chromatography (silica gel, n-heptane/ethyl acetate 5:1). Yield: 782 mg (74%).

b) 3-(6-(2-Fluorophenyl)pyridin-3-yl)propan-1-ol

Under argon, 400 mg (1.46 mmol) of 3-(6-(2-fluorophenyl)pyridin-3-yl)propionic acid ethyl ester and 63.8 mg (2.93 mmol) of lithium borohydride were stirred in 20 ml of THF at 40° C. for 3 h. After cooling, the mixture was cautiously hydrolyzed with water, the precipitate was filtered off with suction, and water and methylene chloride were added to the filtrate. The organic phase was separated, washed with water and concentrated. Yield: 241 mg (71%).

c) 5-(3-Bromopropyl)-2-(2-fluorophenyl)pyridine 230 mg (0.99 mmol) of 3-(6-(2-fluorophenyl)pyridin-3-yl)propan-1-ol were stirred in 10 ml of hydrobromic acid (33% in acetic acid) at 60° C. for 6 h. After concentrating, a sodium hydrogencarbonate solution was added, the resulting mixture was extracted with ethyl acetate, and the organic phase was separated and concentrated. Yield: 707 mg (71%).

d) 1-(3-(6-(2-Fluorophenyl)pyridin-3-yl)propyl)-1H-pyridin-2-one 8.2 mg (0.18 mmol) of sodium hydride (55% suspension in mineral oil) were added to 17.8 mg (0.19 mmol) of 2-hydroxypyridine in 5 ml of DMF, and the mixture was stirred at room temperature for 30 min. Subsequently, 50 mg (0.17 mmol) of 5-(3-bromopropyl)-2-(2-fluorophenyl)pyridine were added. The reaction mixture was stirred for 4 h, concentrated, admixed with water and extracted with methylene chloride. The organic phase was separated and concentrated, and the residue was purified by preparative HPLC (RP18, acetonitrile/water containing 0.1% TFA) Yield: 11 mg (22%).

MS: M+H$^+$=309.1.

Example 2

1-(3-(6-(2-Fluorophenyl)pyridin-3-yl)propyl)piperidin-2-one

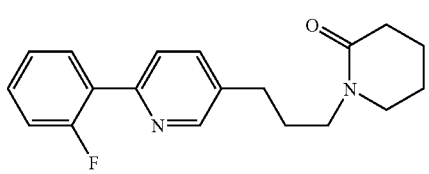 [SMILES: O=C1CCCCN1CCCc1ccc(-c2ccccc2F)nc1]

50 mg (0.17 mmol) of 5-(3-bromopropyl)-2-(2-fluorophenyl)pyridine were reacted with 18.5 mg (0.18 mmol) of piperidin-2-one analogously to example 1d). Yield: 16 mg (31%).

MS: M+H$^+$=313.1.

Example 3

4-(3-(6-Phenylpyridin-3-yl)propyl)thiomorpholin-3-one, trifluoroacetic acid salt

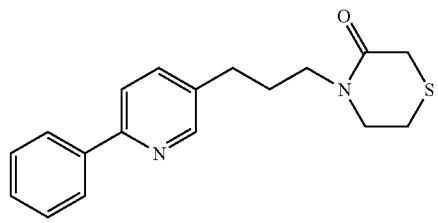 [SMILES: O=C1CSCCN1CCCc1ccc(-c2ccccc2)nc1]

a) 3-(6-Bromopyridin-3-yl)propan-1-ol

Under argon, 560 mg (2.17 mmol) of 3-(6-bromopyridin-3-yl)propionic acid ethyl ester and 94.6 mg (4.34 mmol) of lithium borohydride were stirred in 40 ml of THF at 40° C. for 3 h. After cooling, the mixture was cautiously hydrolyzed with water, the precipitate was filtered off with suction, and the filtrate was concentrated and admixed with water and ethyl acetate. The organic phase was separated, washed with water and concentrated. Yield: 450 mg (96%).
MS: M+H$^+$=216.1.

b) 2-Bromo-5-(3-bromopropyl)pyridine 300 mg (1.38 mmol) of 3-(6-bromopyridin-3-yl)propan-1-ol were stirred in 5 ml of hydrobromic acid (33% in acetic acid) at 80° C. for 6 h. After concentrating, a potassium carbonate solution was added, the resulting mixture was extracted with ethyl acetate, and the organic phase was separated and concentrated. Yield: 368 mg (95%).

c) 4-(3-(6-Bromopyridin-3-yl)propyl)thiomorpholin-3-one 60.2 mg (1.38 mmol) of sodium hydride (55% suspension in mineral oil) were added to 161.7 mg (1.38 mmol) of thiomorpholin-3-one in 5 ml of DMF, and the mixture was stirred at room temperature for 15 min. Subsequently, 350 mg (1.25 mmol) of 2-bromo-5-(3-bromopropyl)pyridine were added. The reaction mixture was stirred for 3.5 h, concentrated, admixed with water and extracted with ethyl acetate. The organic phase was separated and concentrated. Yield: 421 mg.

d) 4-(3-(6-Phenylpyridin-3-yl)propyl)-thiomorpholin-3-one, trifluoroacetic acid salt Under argon, a mixture of 100 mg (0.32 mmol) of 4-(3-(6-bromopyridin-3-yl)propyl)thiomorpholin-3-one, 46.4 mg (0.38 mmol) of phenylboronic acid, 3.6 mg of (0.016 mmol) palladium acetate, 8.3 mg (0.03 mmol) of triphenylphosphane, 320 μl of a 1M sodium carbonate solution and 20 ml of toluene was heated under reflux for 5 h. After cooling, the mixture was poured into water, the resulting mixture was extracted with ethyl acetate, and the organic phase was separated and concentrated. The residue was purified by preparative HPLC (RP18, acetonitrile/water containing 0.1% TFA). Yield: 10 mg (7%).
MS: M+H$^+$=313.0.

Example 4

1-(3-(6-(2-Fluorophenyl)pyridin-3-yl)propyl)pyrrolidin-2-one, trifluoroacetic acid salt

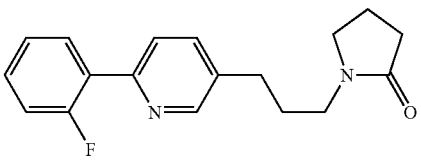 [SMILES: O=C1CCCN1CCCc1ccc(-c2ccccc2F)nc1]

100 mg (0.34 mmol) of 5-(3-bromopropyl)-2-(2-fluorophenyl)pyridine were reacted with 34.7 mg (0.41 mmol) of pyrrolidin-2-one analogously to example 1d). Yield: 50 mg (35%).
MS: M+H$^+$=299.1.

Example 5

1-(3-(6-(2-Fluorophenyl)pyridin-3-yl)propyl)piperidine-2,6-dione, trifluoroacetic acid salt

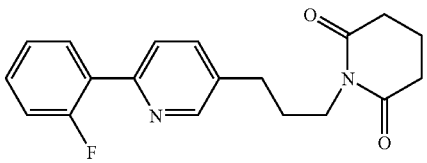 [SMILES: O=C1CCCC(=O)N1CCCc1ccc(-c2ccccc2F)nc1]

100 mg (0.34 mmol) of 5-(3-bromopropyl)-2-(2-fluorophenyl)pyridine were reacted with 46.1 mg (0.41 mmol) of piperidine-2,6-dione analogously to example 1d). Yield: 38 mg (25%).
MS: M+H$^+$=327.1.

Example 6

1-(3-(6-(2-Fluorophenyl)pyridin-3-yl)propyl)azepan-2-one, trifluoroacetic acid salt

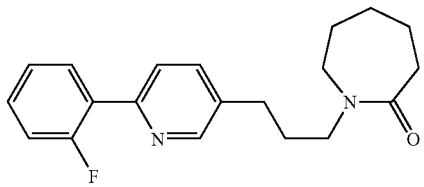 [SMILES: O=C1CCCCCN1CCCc1ccc(-c2ccccc2F)nc1]

100 mg (0.34 mmol) of 5-(3-bromopropyl)-2-(2-fluorophenyl)pyridine were reacted with 46.2 mg (0.41 mmol) of azepan-2-one analogously to example 1d). Yield: 31 mg (23%).
MS: M+H$^+$=327.1.

Example 7

4-(3-(6-(2-Chlorophenyl)pyridin-3-yl)propyl)thiomorpholin-3-one, trifluoroacetic acid salt

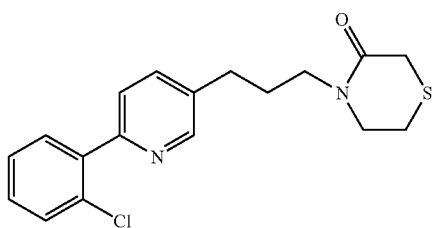 [SMILES: O=C1CSCCN1CCCc1ccc(-c2ccccc2Cl)nc1]

101.5 mg (0.32 mmol) of 4-(3-(6-bromopyridin-3-yl)propyl)thiomorpholin-3-one were reacted with 60.2 mg (0.38 mmol) of 2-chlorophenylboronic acid analogously to example 3d). Yield: 10 mg (7%).

MS: M+H$^+$=347.0.

Example 8

4-(3-(6-(4-Fluorophenyl)pyridin-3-yl)propyl)thiomorpholin-3-one, trifluoroacetic acid salt

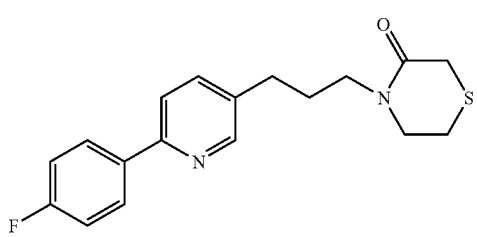 [SMILES: O=C1CSCCN1CCCc1ccc(-c2ccc(F)cc2)nc1]

96 mg (0.3 mmol) of 4-(3-(6-bromopyridin-3-yl)propyl)thiomorpholin-3-one were reacted with 59.7 mg (0.42 mmol) of 4-fluorophenylboronic acid analogously to example 3d). Yield: 12 mg (9%).

MS: M+H$^+$=331.0.

Example 9

4-(3-(6-(2-Fluorophenyl)pyridin-3-yl)propyl)thiomorpholin-3-one, trifluoroacetic acid salt

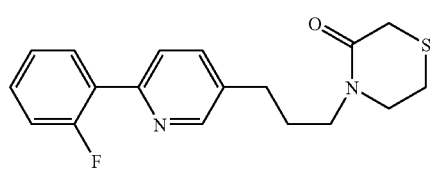 [SMILES: O=C1CSCCN1CCCc1ccc(-c2ccccc2F)nc1]

100 mg (0.34 mmol) of 5-(3-bromopropyl)-2-(2-fluorophenyl)pyridine were reacted with 47.8 mg (0.41 mmol) of thiomorpholin-3-one analogously to example 1d). Yield: 37 mg (24%).

MS: M+H$^+$=331.0.

Example 10

1-(3-(6-(2-Fluorophenyl)pyridin-3-yl)propyl)pyrrolidine-2,5-dione, trifluoroacetic acid salt

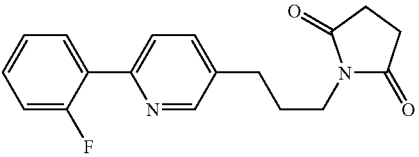 [SMILES: O=C1CCC(=O)N1CCCc1ccc(-c2ccccc2F)nc1]

100 mg (0.34 mmol) of 5-(3-bromopropyl)-2-(2-fluorophenyl)pyridine were reacted with 40.4 mg (0.41 mmol) of pyrrolidine-2,5-dione analogously to example 1d). Yield: 67 mg (46%).

MS: M+H$^+$=313.1.

Example 11

3-(3-(6-(2-Fluorophenyl)pyridin-3-yl)propyl)thiazolidine-2,4-dione, trifluoroacetic acid salt

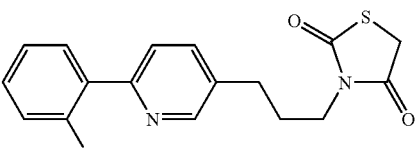

100 mg (0.34 mmol) of 5-(3-bromopropyl)-2-(2-fluorophenyl)pyridine were reacted with 47.8 mg (0.41 mmol) of thiazolidine-2,4-dione analogously to example 1d). Yield: 20 mg (13%).

MS: M+H$^+$=331.1.

Example 12

1-(3-(6-(4-Fluorophenyl)pyridin-3-yl)propyl)pyrrolidin-2-one, trifluoroacetic acid salt

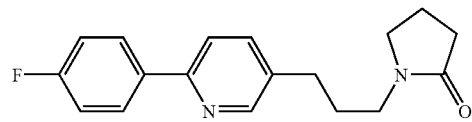 [SMILES: O=C1CCCN1CCCc1ccc(-c2ccc(F)cc2)nc1]

a) Methanesulfonic acid 3-(6-(4-fluorophenyl)pyridin-3-yl)propyl ester 544.8 mg (4.75 mmol) of methanesulfonyl chloride were added dropwise with cooling to 1000 mg (4.32 mmol) of 3-(6-(4-fluorophenyl)pyridin-3-yl)propan-1-ol (prepared analogously to example 1a), starting from 3-(6-bromopyridin-3-yl)propionic acid ethyl ester and 4-fluorophenylboronic acid) and 656.3 mg (6.48 mmol) of triethylamine in 50 ml of methylene chloride. After 5 h at room temperature, the mixture was extracted with water, and the organic phase was separated and concentrated. Yield: 1.3 g (97%).

MS: M+H$^+$=310.1.

b) 1-(3-(6-(4-Fluorophenyl)pyridin-3-yl)propyl)pyr-
rolidin-2-one, trifluoroacetic acid salt 110 mg (0.36 mmol) of methanesulfonic acid 3-(6-(4-fluorophenyl)pyridin-3-yl)propyl ester were reacted with 36.1 mg (0.42 mmol) of pyrrolidin-2-one analogously to example 1d). Yield: 46 mg (31%).
MS: M+H$^+$=299.2.

Example 13

1-(3-(6-(4-Fluorophenyl)pyridin-3-yl)propyl)pyrrolidine-2,5-dione, trifluoroacetic acid salt

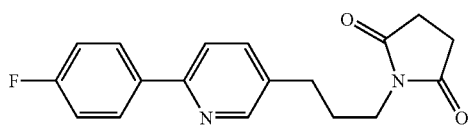

136 mg (0.44 mmol) of methanesulfonic acid 3-(6-(4-fluorophenyl)pyridin-3-yl)propyl ester were reacted with 52.3 mg (0.52 mmol) of pyrrolidine-2,5-dione analogously to example 1d). Yield: 35 mg (19%).
MS: M+H$^+$=313.2.

Example 14

3-(3-(6-(4-Fluorophenyl)pyridin-3-yl)propyl)imidazolidine-2,4-dione, trifluoroacetic acid salt

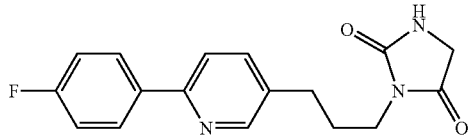

136 mg (0.44 mmol) of methanesulfonic acid 3-(6-(4-fluorophenyl)pyridin-3-yl)propyl ester were reacted with 52.8 mg (0.52 mmol) of imidazolidine-2,4-dione analogously to example 1d). Yield: 8 mg (4%).
MS: M+H$^+$=314.2.

Example 15

1-(3-(6-(4-Fluorophenyl)pyridin-3-yl)propyl)azetidin-2-one, trifluoroacetic acid salt

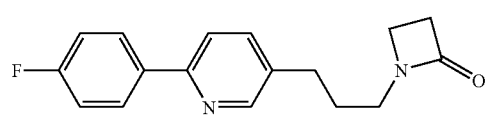 [SMILES: O=C1CCN1CCCc1ccc(-c2ccc(F)cc2)nc1]

136 mg (0.44 mmol) of methanesulfonic acid 3-(6-(4-fluorophenyl)pyridin-3-yl)propyl ester were reacted with 37.5 mg (0.52 mmol) of azetidin-2-one analogously to example 1d). Yield: 8 mg (5%).
MS: M+H$^+$=285.1.

Example 16

1-(3-(6-(4-Fluorophenyl)pyridin-3-yl)propyl)piperidin-2-one, trifluoroacetic acid salt

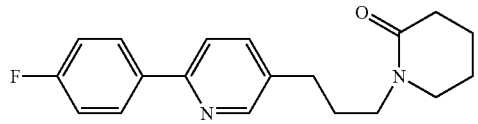 [SMILES: O=C1CCCCN1CCCc1ccc(-c2ccc(F)cc2)nc1]

136 mg (0.44 mmol) of methanesulfonic acid 3-(6-(4-fluorophenyl)pyridin-3-yl)propyl ester were reacted with 52.3 mg (0.52 mmol) of piperidin-2-one analogously to example 1d). Yield: 19 mg (10%).
MS: M+H$^+$=313.2.

Example 17

4-(3-(6-(4-Fluorophenyl)pyridin-3-yl)propylcarbamoyl)butyric acid, trifluoroacetic acid salt

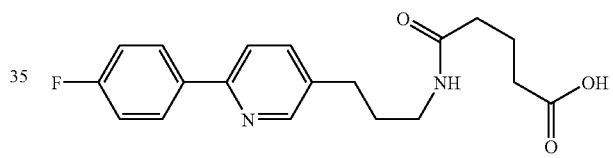

136 mg (0.44 mmol) of methanesulfonic acid 3-(6-(4-fluorophenyl)pyridin-3-yl)propyl ester were reacted with 59.7 mg (0.52 mmol) of piperidine-2,6-dione analogously to example 1d). Yield: 18 mg (8%).
MS: M+H$^+$=345.2.

Example 18

1-(3-(6-(4-Fluorophenyl)pyridin-3-yl)propyl)azepan-2-one, trifluoroacetic acid salt

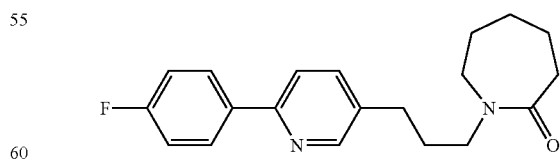

136 mg (0.44 mmol) of methanesulfonic acid 3-(6-(4-fluorophenyl)pyridin-3-yl)propyl ester were reacted with 59.7 mg (0.52 mmol) of azepan-2-one analogously to example 1d). Yield: 78 mg (40%).
MS: M+H$^+$=327.3.

Example 19

4-(3-(6-(2-Fluorophenyl)pyridin-3-yl)propyl)-4H-[1,4]thiazin-3-one, trifluoroacetic acid salt

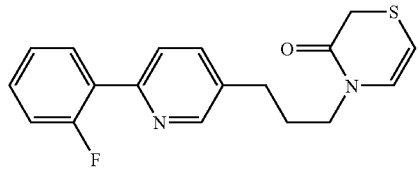

100 mg (0.32 mmol) of methanesulfonic acid 3-(6-(2-fluorophenyl)pyridin-3-yl)propyl ester (prepared from 3-(6-(2-fluorophenyl)pyridin-3-yl)propan-1-ol analogously to example 12a) were reacted with 44.7 mg (0.39 mmol) of 4H-[1,4]thiazin-3-one analogously to example 1d). Yield: 56 mg (40%).

MS: M+H$^+$=329.2.

Example 20

3-(3-(6-(2-Fluorophenyl)pyridin-3-yl)propyl)imidazolidine-2,4-dione, trifluoroacetic acid salt

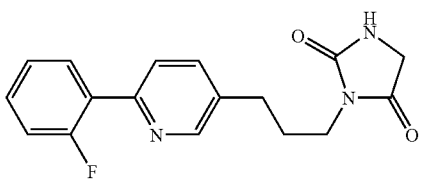 [SMILES: O=C1CNC(=O)N1CCCc1ccc(-c2ccccc2F)nc1]

100 mg (0.32 mmol) of methanesulfonic acid 3-(6-(2-fluorophenyl)pyridin-3-yl)propyl ester (prepared from 3-(6-(2-fluorophenyl)pyridin-3-yl)-propan-1-ol analogously to example 12a) were reacted with 38.8 mg (0.39 mmol) of imidazolidine-2,4-dione analogously to example 1d). Yield: 51 mg (37%).

MS: M+H$^+$=314.2.

Example 21

1-(3-(6-(4-Fluorophenyl)pyridin-3-yl)propyl)piperidine-2,6-dione, trifluoroacetic acid salt

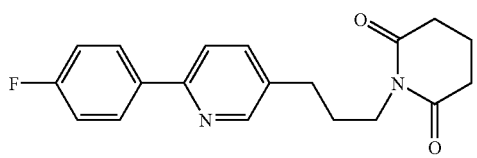 [SMILES: O=C1CCCC(=O)N1CCCc1ccc(-c2ccc(F)cc2)nc1]

136 mg (0.44 mmol) of methanesulfonic acid 3-(6-(4-fluorophenyl)pyridin-3-yl)propyl ester were reacted with 69.6 mg (0.61 mmol) of piperidine-2,6-dione analogously to example 1d). Yield: 77 mg (40%).

MS: M+H$^+$=327.2.

Example 22

3-(3-(6-(4-Fluorophenyl)pyridin-3-yl)propyl)thiazolidine-2,4-dione, trifluoroacetic acid salt

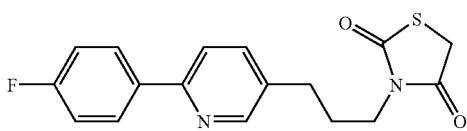 [SMILES: O=C1CSC(=O)N1CCCc1ccc(-c2ccc(F)cc2)nc1]

136 mg (0.44 mmol) of methanesulfonic acid 3-(6-(4-fluorophenyl)pyridin-3-yl)propyl ester were reacted with 61.8 mg (0.52 mmol) of thiazolidine-2,4-dione analogously to example 1d). Yield: 53 mg (27%).

MS: M+H$^+$=331.2.

Example 23

1-(3-(6-(2-Fluorophenyl)pyridin-3-yl)propyl)azetidin-2-one, trifluoroacetic acid salt

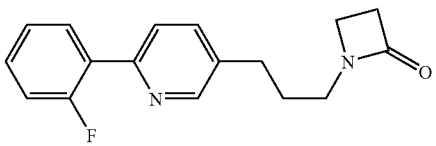

100 mg (0.32 mmol) of methanesulfonic acid 3-(6-(2-fluorophenyl)pyridin-3-yl)propyl ester (prepared from 3-(6-(2-fluorophenyl)pyridin-3-yl)propan-1-ol analogously to example 12a) were reacted with 32.2 mg (0.45 mmol) of azetidin-2-one analogously to example 1d). Yield: 8 mg (5%).

MS: M+H$^+$=285.2.

Example 24

1-(3-(6-(4-Fluorophenyl)pyridin-3-yl)propyl)-1H-pyridin-2-one, trifluoroacetic acid salt

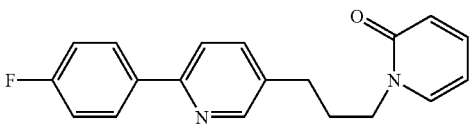

136 mg (0.44 mmol) of methanesulfonic acid 3-(6-(4-fluorophenyl)pyridin-3-yl)propyl ester were reacted with 50.2 mg (0.52 mmol) of 1H-pyridin-2-one analogously to example 1d). Yield: 98 mg (52%).

MS: M+H$^+$=309.2.

Example 25

4-(3-(6-(4-Fluorophenyl)pyridin-3-yl)propyl)-4H-[1,4]thiazin-3-one, trifluoroacetic acid salt

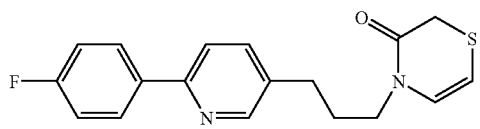 [SMILES: O=C1CSC=CN1CCCc1ccc(-c2ccc(F)cc2)nc1]

136 mg (0.44 mmol) of methanesulfonic acid 3-(6-(4-fluorophenyl)pyridin-3-yl)propyl ester were reacted with 60.7 mg (0.52 mmol) of 4H-[1,4]thiazin-3-one analogously to example 1d). Yield: 17 mg (9%).

MS: M+H$^+$=329.2.

Example 26

1-(2-(6-(2-Fluorophenyl)pyridin-3-yloxy)ethyl)piperidin-2-one, trifluoroacetic acid salt

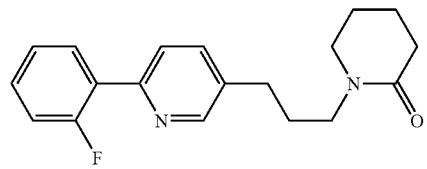 [SMILES: O=C1CCCCN1CCCc1ccc(-c2ccccc2F)nc1]

a) (6-(2-Fluorophenyl)pyridin-3-yloxy)acetic acid methyl ester

Under argon, 157.3 mg (3.6 mmol) of sodium hydride (55% suspension in mineral oil) were added to 620 mg (3.27 mmol) of 6-(2-fluorophenyl)pyridin-3-ol in 25 ml of DMF. After stirring at room temperature for 60 min, 551.4 mg (3.6 mmol) of bromoacetic acid methyl ester were added, and the reaction mixture was stirred at room temperature for 2 h. After concentrating, water was added, and the mixture was extracted with ethyl acetate. The organic phase was separated and concentrated. Yield: 687 mg (80%).

MS: M+H$^+$=262.1.

b) 2-(6-(2-Fluorophenyl)pyridin-3-yloxy)ethanol

Under argon, 675 mg (2.58 mmol) of (6-(2-fluorophenyl)pyridin-3-yloxy)acetic acid methyl ester and 112.5 mg (5.17 mmol) of lithium borohydride were stirred in 20 ml of THF at 60° C. for 2 h. After cooling, the mixture was cautiously hydrolyzed with water and concentrated, and water and ethyl acetate were added. The organic phase was separated, washed with water and concentrated. Yield: 350 mg (58%).

MS: M+H$^+$=234.1.

c) Methanesulfonic acid 2-(6-(2-fluorophenyl)pyridin-3-yloxy)ethyl ester 217.1 mg (1.89 mmol) of methanesulfonyl chloride were added dropwise with cooling to 340 mg (1.46 mmol) of 2-(6-(2-fluorophenyl)pyridin-3-yloxy)ethanol and 442.5 mg (4.37 mmol) of triethylamine in 25 ml of methylene chloride. After 7 h at room temperature, the mixture was extracted with water, and the organic phase was separated and concentrated. Yield: 394 mg (87%).

MS: M+H$^+$=312.2.

d) 1-(2-(6-(2-Fluorophenyl)pyridin-3-yloxy)-ethyl)piperidin-2-one, trifluoroacetic acid salt 100 mg (0.32 mmol) of methanesulfonic acid 2-(6-(2-fluorophenyl)pyridin-3-yloxy)ethyl ester were reacted with 38.2 mg (0.38 mmol) of piperidin-2-one analogously to example 1d). Yield: 15 mg (11%).

MS: M+H$^+$=315.1.

Example 27

1-(2-(6-(2-Fluorophenyl)pyridin-3-yloxy)ethyl)azetidin-2-one, trifluoroacetic acid salt

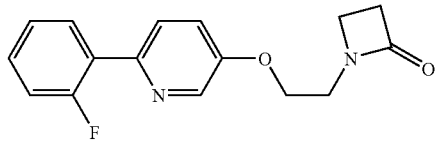 [SMILES: O=C1CCN1CCOc1ccc(-c2ccccc2F)nc1]

100 mg (0.32 mmol) of methanesulfonic acid 2-(6-(2-fluorophenyl)pyridin-3-yloxy)ethyl ester were reacted with 27.4 mg (0.38 mmol) of azetidin-2-one analogously to example 1d). Yield: 4 mg (3%).

MS: M+H$^+$=287.1.

Example 28

1-(2-(6-(2-Fluorophenyl)pyridin-3-yloxy)ethyl)pyrrolidine-2,5-dione, trifluoroacetic acid salt

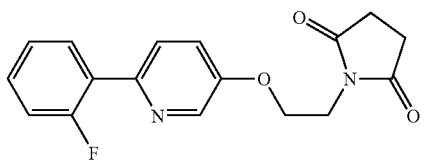

100 mg (0.32 mmol) of methanesulfonic acid 2-(6-(2-fluorophenyl)pyridin-3-yloxy)ethyl ester were reacted with 38.2 mg (0.38 mmol) of pyrrolidine-2,5-dione analogously to example 1d). Yield: 52 mg (38%).

MS: M+H$^+$=315.1.

Example 29

3-(2-(4-(4-Fluorophenyl)thiazol-2-ylamino)ethyl)imidazolidine-2,4-dione, trifluoroacetic acid salt

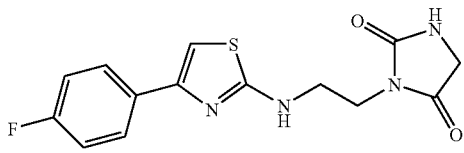 [SMILES: O=C1CNC(=O)N1CCNc1nc(-c2ccc(F)cc2)cs1]

200 mg (0.92 mmol) of 2-bromo-1-(4-fluorophenyl)ethanone and 74.7 mg (0.92 mmol) of sodium thiocyanate were stirred in ethanol at 50° C. for 2 h. 165.5 mg (0.92 mmol) of 3-(2-aminoethyl)imidazolidine-2,4-dione hydrochloride and 102.6 mg (1.01 mmol) of triethylamine were added, and the reaction mixture was stirred at 50° C. for 9 h. After concentrating, water was added, and the mixture was extracted with ethyl acetate. The organic phase was separated and concentrated, and the residue was purified by preparative HPLC (RP18, acetonitrile/water containing 0.1% TFA). Yield: 82 mg (20%).
MS: M+H$^+$=321.0.

Example 30

3-(2-(6-(2-Fluorophenyl)pyridin-3-yloxy)ethyl)imidazolidine-2,4-dione, trifluoroacetic acid salt

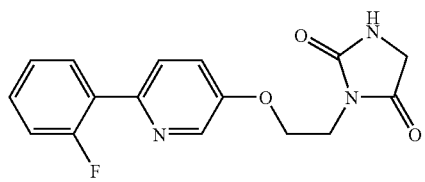 [SMILES: O=C1CNC(=O)N1CCOc1ccc(-c2ccccc2F)nc1]

90 mg (0.29 mmol) of methanesulfonic acid 2-(6-(2-fluorophenyl)pyridin-3-yloxy)ethyl ester were reacted with 34.7 mg (0.35 mmol) of imidazolidine-2,4-dione analogously to example 1d). Yield: 4 mg (3%).
MS: M+H$^+$=316.2.

Example 31

2-(2-(4-(4-Fluorophenyl)thiazol-2-ylamino)ethyl)isoindole-1,3-dione, trifluoroacetic acid salt

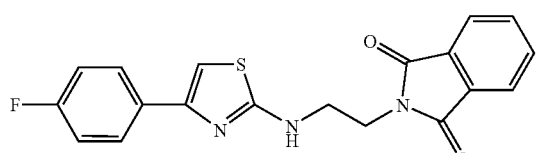

a) (2-(4-(4-Fluorophenyl)thiazol-2-ylamino)ethyl)carbamic acid tert-butyl ester 2.5 g (11.52 mmol) of 2-bromo-1-(4-fluorophenyl)ethanone and 0.93 g (11.52 mmol) of sodium thiocyanate were stirred in ethanol at 50° C. for 2 h. 1.845 g (11.52 mmol) of (2-aminoethyl)carbamic acid tert-butyl ester were added, and the reaction mixture was stirred at 50° C. for 2 h. After concentrating, water was added, and the mixture was extracted with ethyl acetate. The organic phase was separated and concentrated. Yield: 3.04 g (78%).

b) N-(4-(4-Fluorophenyl)thiazol-2-yl)ethane-1,2-diamine, trifluoroacetic acid salt A mixture of 996 mg (2.95 mmol) of (2-(4-(4-fluorophenyl)thiazol-2-ylamino)ethyl)carbamic acid tert-butyl ester and 5 ml of 90% aqueous trifluoroacetic acid was allowed to stand at room temperature for 4 h. After concentrating, the residue was purified by preparative HPLC (RP18, acetonitrile/water containing 0.1% TFA). Yield: 122 mg (9%).
MS: M+H$^+$=238.1.

c) 2-(2-(4-(4-Fluorophenyl)thiazol-2-ylamino)ethyl)isoindole-1,3-dione, trifluoroacetic acid salt A mixture of 54.3 mg (0.11 mmol) of N-(4-(4-fluorophenyl)thiazol-2-yl)ethane-1,2-diamine, trifluoroacetic acid salt, 35.4 mg (0.35 mmol) of triethylamine, 17.3 mg (0.11 mmol) of phthalic anhydride, 5 ml of toluene and 1 ml of DMF was heated under reflux for 3 h. After concentrating, the residue was extracted with an aqueous solution of sodium hydrogensulfate (pH 5) and a sodium hydrogencarbonate solution and concentrated, and the residue was purified by preparative HPLC (RP18, acetonitrile/water containing 0.1% TFA). Yield: 16 mg (28%).
MS: M+H$^+$=368.1.

Example 32

1-(2-(5-(2-Fluorophenyl)pyridin-2-yloxy)ethyl)pyrrolidin-2-one, trifluoroacetic acid salt

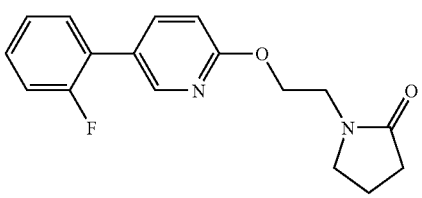 [SMILES: O=C1CCCN1CCOc1ccc(-c2ccccc2F)cn1]

a) 1-(2-(5-Bromopyridin-2-yloxy)ethyl)pyrrolidin-2-one 2.45 g (19 mmol) of 1-(2-hydroxyethyl)-pyrrolidin-2-one and 0.83 g (19 mmol) of sodium hydride (55% in mineral oil) in 10 ml of NMP were stirred at room temperature for 1 h. 3.0 g (12.7 mmol) of 2,5-dibromopyridine were added, and the mixture was heated to 80° C. for 2 h. Water was added, and the mixture was extracted with ethyl acetate. The combined organic phases were dried and concentrated. The remaining oil was taken up in 200 ml of tert-butyl methyl ether and treated with a solution of hydrogen chloride in diethyl ether. The resulting greasy solid was isolated by decantation of the solvent and treated with a 25% aqueous sodium hydroxide solution. The product was extracted with ethyl acetate, and the combined organic phases were dried and concentrated. Yield: 2.75 g.

b) 1-(2-(5-(2-Fluorophenyl)pyridin-2-yloxy)ethyl)pyrrolidin-2-one, trifluoroacetic acid salt 88.3 mg (0.62 mmol) of 2-fluorobenzeneboronic acid, 150 mg (0.53 mmol) of 1-(2-(5-bromopyridin-2-yloxy)ethyl)pyrrolidin-2-one, 249 mg (0.79 mmol) of barium hydroxide octahydrate and 20 mg of tetrakis(triphenylphosphane)palladium were dissolved in 10 ml 1,2-dimethoxyethane and 10 ml water, and the mixture was heated to 80° C. for 5 h. The solvent was evaporated, and the residue taken up in water and extracted with methylene chloride. The combined organic phases were dried and concentrated, and the residue was purified by preparative HPLC (RP18, acetonitrile/water containing 0.01% TFA). Yield: 60 mg.

Example 33

1-(2-(5-(1-Methyl-1H-benzoimidazol-2-yl)pyridin-2-yloxy)ethyl)pyrrolidin-2-one, trifluoroacetic acid salt

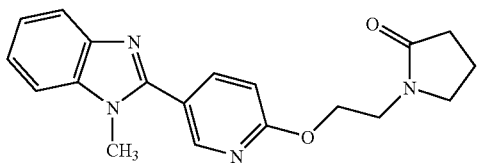 [SMILES: Cn1c(-c2ccc(OCCN3CCCC3=O)nc2)nc2ccccc21]

The compound was prepared analogously to example 32a) by reaction of 500 mg (2.1 mmol) of 2-(6-chloropyridin-3-yl)-1-methyl-1H-benzoimidazole with 1-(2-hydroxyethyl)pyrrolidin-2-one. Yield: 370 mg.
MS: M+H$^+$=337.

Example 34

1-(2-(4-(4-Fluorophenyl)thiazol-2-ylamino)ethyl)pyrrolidine-2,5-dione, trifluoroacetic acid salt

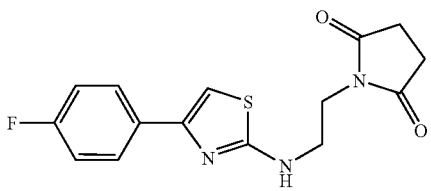

a) (4-(4-Fluorophenyl)thiazol-2-ylamino)acetic acid methyl ester 14.5 g (66.8 mmol) of 2-bromo-1-(4-fluorophenyl)ethanone and 5.42 g (66.8 mmol) of sodium thiocyanate were stirred in 250 ml of ethanol at 50° C. for 3 h. 5.95 g (66.8 mmol) of aminoacetic acid methyl ester (prepared from its hydrochloride) in 25 ml of ethanol were added, and the reaction mixture was stirred at room temperature for 4 h and allowed to stand overnight. After concentrating, water and ethyl acetate were added to the residue. The organic phase was separated, washed with water, dried and concentrated. Yield: 8.6 g (48%).
MS: M+H$^+$=266.3.

b) (tert-Butoxycarbonyl-(4-(4-fluorophenyl)thiazol-2-yl)-amino)acetic acid methyl ester 360 mg (8.3 mmol) of sodium hydride (55% suspension in mineral oil) were added to 2 g (7.5 mmol) of (4-(4-fluorophenyl)thiazol-2-ylamino)acetic acid methyl ester in 25 ml of DMF, and the mixture was stirred at room temperature for 60 min. Subsequently 1.8 g (8.3 mmol) of di-tert-butyl-dicarbonate were added, and the reaction mixture was stirred for 2 h. After concentrating, water was added and the mixture extracted with ethyl acetate. The organic phase was concentrated, and the residue was purified by chromatography (silica gel, n-heptane/ethyl acetate 5:1). Yield: 440 mg (16%).
MS: M+H$^+$=367.2.

c) (4-(4-Fluorophenyl)thiazol-2-yl)-(2-hydroxyethyl)-carbamic acid tert-butyl ester Under argon, 435 mg (1.18 mmol) of (tert-butoxycarbonyl-(4-(4-fluorophenyl)thiazol-2-yl)-amino)acetic acid methyl ester and 51.7 mg (2.37 mmol) of lithium borohydride were stirred in 20 ml of THF at 60° C. for 1 h. After cooling, the mixture was cautiously hydrolyzed with water, the precipitate was filtered off with suction, and water and ethyl acetate were added to the filtrate. The organic phase was separated, washed with water and concentrated. Yield: 273 mg (68%).

d) Methanesulfonic acid 2-(tert-butoxycarbonyl-(4-(4-fluorophenyl)thiazol-2-yl)amino)ethyl ester 98.7 mg (0.86 mmol) of methanesulfonyl chloride were added dropwise with cooling to 265 mg (0.78 mmol) of (4-(4-fluorophenyl)thiazol-2-yl)-(2-hydroxyethyl)-carbamic acid tert-butyl ester and 237.7 mg (2.35 mmol) of triethylamine in 25 ml of methylene chloride. After 4 h at room temperature, the mixture was extracted with water and the organic phase was concentrated. Yield: 241 mg (74%).

e) 1-(2-(4-(4-Fluorophenyl)thiazol-2-ylamino)ethyl)pyrrolidine-2,5-dione, trifluoroacetic acid salt 23 mg (0.52 mmol) of sodium hydride (55% suspension in mineral oil) were added to 52.3 mg (0.52 mmol) of pyrrolidine-2,5-dione in 5 ml of DMF, and the mixture was stirred at room temperature for 60 min. Subsequently 100 mg (0.24 mmol) of methanesulfonic acid 2-(tert-butoxycarbonyl-(4-(4-fluorophenyl)thiazol-2-yl)-amino)ethyl ester were added and the reaction mixture was stirred for 3 h. After concentrating, water was added, and the mixture was extracted with ethyl acetate. The organic phase was separated and concentrated, and the residue was purified by preparative HPLC (RP18, acetonitrile/water containing 0.1% TFA). Yield: 5 mg (5%).
MS: M+H$^+$=320.1.

Example 35

N-(2-(4-(4-Fluorophenyl)thiazol-2-ylamino)ethyl)acetamide

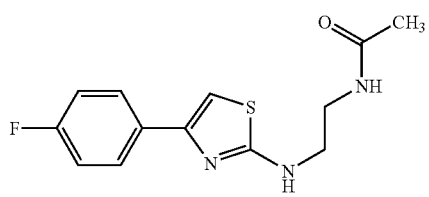 [SMILES: CC(=O)NCCNc1nc(-c2ccc(F)cc2)cs1]

2-Bromo-1-(4-fluorophenyl)ethanone was reacted with N-(2-aminoethyl)acetamide analogously to example 31a). Yield: 65%.
MS: M+H$^+$=280.2.

Example 36

1-(2-(6-(4-Fluorophenyl)pyridin-3-yloxy)ethyl)pyrrole-2,5-dione, trifluoroacetic acid salt

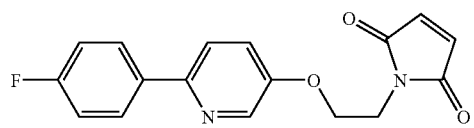 [SMILES: O=C1C=CC(=O)N1CCOc1ccc(-c2ccc(F)cc2)nc1]

80 mg (0.42 mmol) of 6-(4-fluorophenyl)pyridin-3-ol, 61.2 mg (0.43 mmol) of 1-(2-hydroxyethyl)pyrrole-2,5-dione and 155.3 mg (0.59 mmol) of triphenylphosphane were dissolved in 20 ml of THF. After cooling to 0° C., 136.2 mg (0.59 mmol) of azodicarboxylic acid di-tert-butyl ester in 3 ml THF were slowly added. The mixture was stirred at room temperature for 6 h, evaporated and treated with ethyl acetate and diluted hydrochloric acid. The aqueous layer was evaporated and purified by chromatography (RP18, acetonitrile/water containing 0.1% TFA). Yield: 17 mg.
MS: M+H$^+$=313.1.

Example 37

2-(2-(6-(2-Fluorophenyl)pyridin-3-yloxy)ethyl)isoindole-1,3-dione

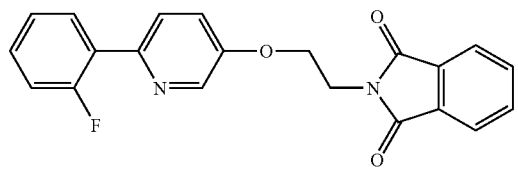

500 mg (2.64 mmol) of 6-(2-fluorophenyl)pyridin-3-ol (prepared from 2-bromo-5-nitropyridine and 2-fluorophenylboronic acid; the nitro group was converted into the hydroxy group according to the method described in WO 98/25920), 730.6 mg (5.28 mmol) of potassium carbonate and 738.6 mg (2.91 mmol) of 2-(2-bromoethyl)-isoindole-1,3-dione in 10 ml of DMF were stirred at room temperature for 4 h. The solvent was removed by evaporation and the residue treated with ethyl acetate and water. The organic layer was evaporated and the residue purified by chromatography. Yield: 189 mg.
MS: M+H$^+$=363.2.

Example 38

1-(2-(6-(4-Fluorophenyl)pyridin-3-yloxy)ethyl)pyrrolidine-2,5-dione, trifluoroacetic acid salt

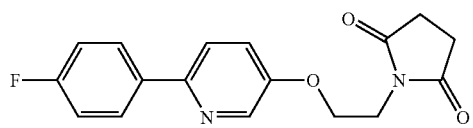 [SMILES: O=C1CCC(=O)N1CCOc1ccc(-c2ccc(F)cc2)nc1]

128.7 mg (0.58 mmol) of methanesulfonic acid 2-(2,5-dioxopyrrolidin-1-yl)ethyl ester and 100 mg (0.53 mmol) of 6-(4-fluorophenyl)pyridin-3-ol were reacted analogously to example 1d). Yield: 30 mg.
MS: M+H$^+$=315.1.

Example 39

1-(2-(6-(4-Fluorophenyl)pyridin-3-yloxy)ethyl)-1H-pyridin-2-one, trifluoroacetic acid salt

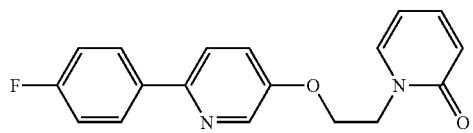 [SMILES: O=c1ccccn1CCOc1ccc(-c2ccc(F)cc2)nc1]

100 mg (0.63 mmol) of 1-(2-chloroethyl)-1H-pyridin-2-one and 100 mg (0.53 mmol) of 6-(4-fluorophenyl)pyridin-3-ol were reacted analogously to example 1d). Yield: 11 mg.
MS: M+H$^+$=311.1.

Example 40

1-(2-(4-(4-Fluorophenyl)thiazol-2-ylamino)ethyl)imidazolidin-2-one, trifluoroacetic acid salt

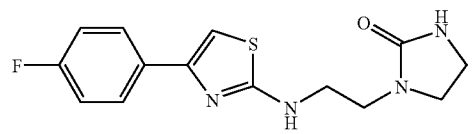 [SMILES: O=C1NCCN1CCNc1nc(-c2ccc(F)cc2)cs1]

a) 1-(4-Fluorophenyl)-2-thiocyanatoethanone 10 g (46 mmol) of 2-bromo-1-(4-fluorophenyl)ethanone and 3.74 g (46 mmol) of sodium thiocyanate were stirred in 80 ml ethanol at 50° C. for 2 h. After addition of water the separated solid was isolated by filtration, washed and dried. Yield: 8.96 g.
MS: M+H$^+$=196.2.

b) 1-(2-(4-(4-Fluorophenyl)thiazol-2-ylamino)ethyl)
imidazolidin-2-one, trifluoroacetic acid salt 65.8 mg (0.5 mmol) of 1-(4-fluorophenyl)-2-thiocyanato-ethanone and 99.5 mg (0.5 mmol) of 1-(2-aminoethyl)imidazolidin-2-one were stirred in 5 ml of ethanol at 50° C. for 4 h. The solvent was evaporated and the residue purified by chromatography (RP18, acetonitrile/water containing 0.1% TFA). Yield: 17 mg.
MS: M+H$^+$=307.1.

Example 41

4-Chloro-N-(2-(4-(4-fluorophenyl)thiazol-2-ylamino)ethyl)benzamide, trifluoroacetic acid salt

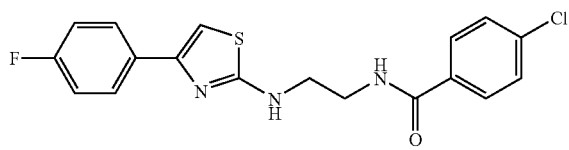 [SMILES: O=C(NCCNc1nc(-c2ccc(F)cc2)cs1)c1ccc(Cl)cc1]

The compound was prepared analogously to example 40b).
Yield: 30 mg.
MS: M+H$^+$=376.1.

Example 42

4-Aminofurazan-3-carboxylic acid (2-(4-(4-fluorophenyl)thiazol-2-ylamino)ethyl)amide, trifluoroacetic acid salt

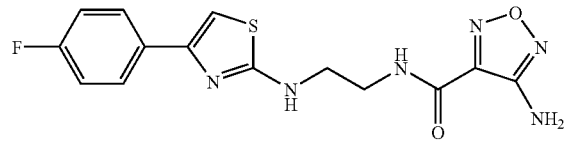 [SMILES: Nc1nonc1C(=O)NCCNc1nc(-c2ccc(F)cc2)cs1]

The compound was prepared analogously to example 40b).
Yield: 54 mg.
MS: M+H$^+$=349.1.

Example 43

N-(2-(4-(4-Fluorophenyl)thiazol-2-ylamino)ethyl) isonicotinamide, trifluoroacetic acid salt

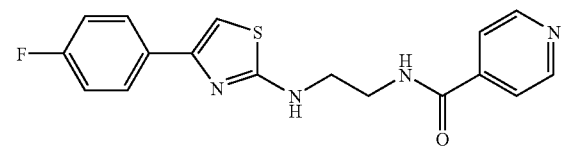 [SMILES: O=C(NCCNc1nc(-c2ccc(F)cc2)cs1)c1ccncc1]

The compound was prepared analogously to example 40b).
Yield: 52 mg.
M S: M+H$^+$=343.1.

Example 44

3-(2-(6-(4-Fluorophenyl)pyridin-3-yloxy)ethyl)imidazolidine-2,4-dione, hydrochloride

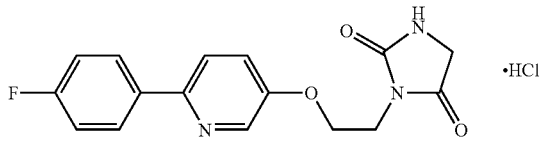

100 mg (0.32 mmol) of methanesulfonic acid 2-(6-(4-fluorophenyl)pyridin-3-yloxy)ethyl ester and 35.4 mg (0.35 mmol) of imidazolidine-2,4-dione were reacted analogously to example 1d). The hydrochloride salt was prepared by dissolution of the product in hydrochloric acid and lyophilization. Yield: 58 mg.
MS: M+H$^+$=316.1.

Example 45

N-(2-(6-(2-Fluorophenyl)pyridin-3-yloxy)ethyl)acetamide, trifluoroacetic acid salt

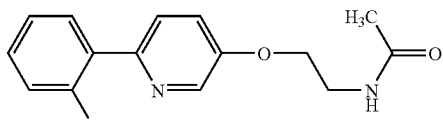

a) 2-(6-(2-Fluorophenyl)pyridin-3-yloxy)ethylamine 189 mg (0.52 mmol) of (2-(2-(6-(2-fluorophenyl)pyridin-3-yloxy)ethyl)isoindole-1,3-dione and 236 mg (4.72 mmol) of hydrazine hydrate (24%) were stirred in 10 ml of ethanol under reflux for 7 h. After cooling the residue was filtered, washed and dried. Yield: 165 mg.
MS: M+H$^+$=233.3.

b) N-(2-(6-(2-Fluorophenyl)pyridin-3-yloxy)ethyl) acetamide, trifluoroacetic acid salt 59.9 mg (0.26 mmol) of 2-(6-(2-fluorophenyl)pyridin-3-yloxy)ethylamine and 52.2 mg (0.52 mmol) of triethylamine were stirred in 5 ml of methylene chloride at room temperature. 31.6 mg (0.31 mmol) of acetic acid anhydride were slowly added. The mixture was stirred for 4 h, washed with water, evaporated and purified by chromatography (RP18, acetonitrile/water containing 0.1% TFA). Yield: 17 mg.
MS: M+H$^+$=275.1.

Example 46

3-(3-(6-(4-Fluorophenyl)pyridin-3-yl)propyl)-5,5-dimethylimidazolidine-2,4-dione, trifluoroacetic acid salt

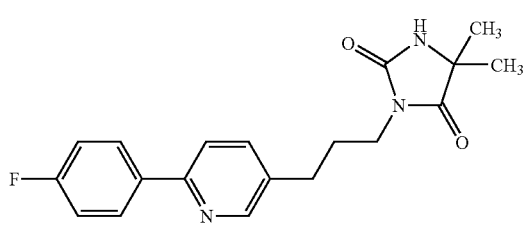 [SMILES: CC1(C)NC(=O)N(CCCc2ccc(-c3ccc(F)cc3)nc2)C1=O]

69 mg (0.226 mmol) of methanesulfonic acid 3-(6-(4-fluorophenyl)pyridin-3-yl)propyl ester were reacted with 43.44 mg (0.339 mmol) of 5,5-dimethylimidazolidine-2,4-dione in the presence of 2.7 mg (0.34 mmol) of lithium hydride analogously to example 1d). Yield: 37 mg.
MS: M+H$^+$=342.12.

Example 47

N-(2-(6-(2-Fluorophenyl)pyridin-3-yloxy)ethyl)benzamide, trifluoroacetic acid salt

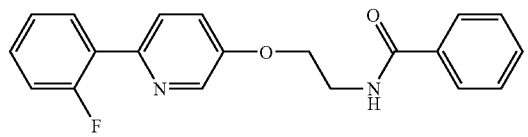 [SMILES: O=C(NCCOc1ccc(-c2ccccc2F)nc1)c1ccccc1]

28.9 mg (0.24 mmol) of benzoic acid, 49.9 mg (0.21 mmol) of 2-(6-(2-fluorophenyl)pyridin-3-yloxy)ethylamine, 89.9 mg (0.27 mmol) of N,N,N',N'-tetramethyl-O-(7-azabenzotriazol-1-yl)uronium hexafluorophosphate and 65.2 mg (0.64 mmol) of triethylamine were stirred in 8 ml of DMF at room temperature for 2 h and at 40° C. for 3 h. The solvent was removed by evaporation and the residue treated with ethyl acetate and water. The organic layer was evaporated and purified by chromatography (RP18, acetonitrile/water containing 0.1% TFA). Yield: 27 mg.
MS: M+H$^+$=337.1.

Example 48

Cyclopropanecarboxylic acid (2-(6-(2-fluorophenyl)pyridin-3-yloxy)ethyl)amide, trifluoroacetic acid salt

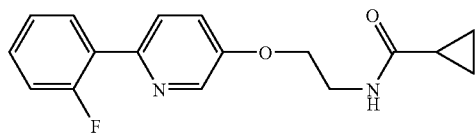 [SMILES: O=C(NCCOc1ccc(-c2ccccc2F)nc1)C1CC1]

20.36 mg (0.24 mmol) of cyclopropanecarboxylic acid and 49.94 mg (0.21 mmol) of 2-(6-(2-fluorophenyl)pyridin-3-yloxy)ethylamine were reacted analogously to example 47. Yield: 15 mg.
MS: M+H$^+$=301.2.

Example 49

3-(3-(6-(4-Fluorophenyl)pyridin-3-yl)propyl)oxazolidin-2-one, trifluoroacetic acid salt

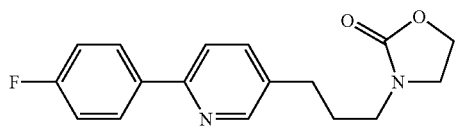 [SMILES: O=C1OCCN1CCCc1ccc(-c2ccc(F)cc2)nc1]

The compound was prepared analogously to example 12b).
Yield: 22 mg.
MS: M+H$^+$=301.0.

Example 50

1-(2-(6-(3-Chloro-4-fluorophenyl)pyridin-3-yloxy)ethyl)pyrrolidine-2,5-dione, trifluoroacetic acid salt

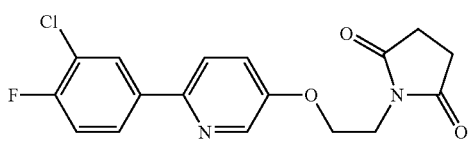 [SMILES: O=C1CCC(=O)N1CCOc1ccc(-c2ccc(F)c(Cl)c2)nc1]

a) 1-(2-(6-Bromopyridin-3-yloxy)ethyl)pyrrolidine-2,5-dione 10 g (58 mmol) of 3-hydroxy-6-bromopyridine were dissolved in 40 ml of DMF and treated with 2.76 g (69 mmol) of sodium hydride (60% suspension in mineral oil). After stirring at room temperature for 1 h, 20 mg of 4-dimethylaminopyridine were added and the mixture was treated with 16.53 g (74.8 mmol) of methanesulfonic acid 2-(2,5-dioxopyrrolidin-1-yl)ethyl ester and heated to 100° C. for 3 h. Subsequently, the solvent was evaporated and the residue was taken up in water and extracted 4 times with ethyl acetate. The combined organic phases were dried and evaporated to dryness. The remaining material was purified by chromatography (silica gel, dichloromethane/methanol 98:2) followed by preparative HPLC (RP18, acetonitrile/water containing 0.1% TFA) to yield 10.8 g of the title compound.

b) 1-(2-(6-(3-Chloro-4-fluorophenyl)pyridin-3-yloxy)ethyl)pyrrolidine-2,5-dione, trifluoroacetic acid salt 150 mg (0.5 mmol) of 1-(2-(6-bromopyridin-3-yloxy)ethyl)pyrrolidine-2,5-dione, 96 mg (0.55 mmol) of 3-chloro-4-fluorophenylboronic acid and 152 mg (0.5 mmol) of cesium fluoride were dissolved under an argon atmosphere in 5 ml of a mixture of 2 parts of absolute 1,2-dimethoxyethane and 1 part of absolute methanol and treated with 34.2 mg (0.09 mmol) of tetrakis(triphenylphosphane)palladium. The mixture was heated for 3 min at 150° C. in a microwave reactor (Smith Synthesizer, Personal Chemistry), the solvent was evaporated and the residue dissolved in 20 ml of ethyl acetate. The solution was extracted once with sodium hydrogencarbonate solution, dried and evaporated to dryness. The remaining material was purified by preparative HPLC (RP18, acetonitrile/water containing 0.1% TFA). Yield: 42 mg (24%).

$^1$H-NMR (D$_6$-DMSO): δ (ppm)=2.65 (s, 4H), 3.75 (m, 2H), 4.25 (m, 2H), 7.48 (m, 2H), 7.50-7.65 (m, 1H), 7.98 (m, 1H), 8.05 (m, 1H), 8.22 (d, 1H), 8.33 (s, 1H).

MS: M+H$^+$=349.

HPLC retention time: 1.72 min (method HPLC A).

According to the method described in example 50, by replacing the 3-chloro-4-fluorophenylboronic acid employed in step b) with the respective boronic acid of the formula R$^{50}$—B(OH)$_2$, the 1-(2-(6-R$^{50}$-pyridin-3-yloxy)ethyl)pyrrolidine-2,5-diones of examples 51 to 87 were prepared which are compounds of the formula Ie wherein the aromatic or heteroaromatic group R$^{50}$ is as specified in table 1.

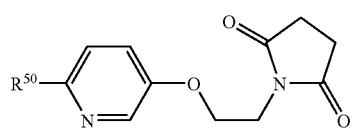

Ie

The compounds of examples 51 to 87 were obtained in the form of their trifluoroacetic acid salts. The names of the prepared compounds are obtained by replacing the identifier R$^{50}$ in the general name 1-(2-(6-R$^{50}$-pyridin-3-yloxy)ethyl)pyrrolidine-2,5-dione of the compounds of formula Ie with the meaning of R$^{50}$ given in table 1, optionally allowing for a modification of the name according to the nomenclature rules. For example, in the case of example 51, in which R$^{50}$ is 6-fluoropyridin-3-yl, the prepared compound of the formula If

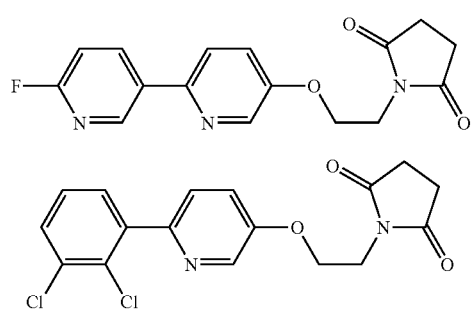

If

Ig thus is 1-(2-(6-(6-fluoropyridin-3-yl)pyridin-3-yloxy)ethyl)pyrrolidine-2,5-dione, trifluoroacetic acid salt, which can also be named as 1-(2-(6'-fluoro-[2,3']bipyridinyl-5-yloxy)ethyl)pyrrolidine-2,5-dione; trifluoroacetic acid salt or 1-(2-(6'-fluoro-[2,3'-bipyridin]-5-yloxy)ethyl)pyrrolidine-2,5-dione, trifluoroacetic acid salt, and in the case of example 60 the prepared compound of the formula Ig is 1-(2-(6-(2,3-dichloro-phenyl)pyridin-3-yloxy))ethyl)pyrrolidine-2,5-dione, trifluoroacetic acid salt, and in the case of example 64 the prepared compound is 1-(2-(6-(3-cyanophenyl)pyridin-3-yloxy))ethyl)pyrrolidine-2,5-dione, trifluoroacetic acid salt, which can also be named as 3-(5-(2-(2,5-dioxopyrrolidin-1-yl)ethoxy)pyridin-2-yl)benzonitrile, trifluoroacetic acid salt. The HPLC retention times given in table 1 were determined according to method HPLC A.

TABLE 1

Example compounds of formula Ie

| Example no. | R$^{50}$ | MS M + H$^+$ | HPLC retention time (min) |
|---|---|---|---|
| 51 | 6-fluoropyridin-3-yl | 316 | 1.45 |
| 52 | 4-methylthiophen-2-yl | 317 | 1.64 |
| 53 | 3,4,5-trifluorophenyl | 351 | 1.77 |
| 54 | 3-trifluoromethoxyphenyl | 381 | 1.77 |
| 55 | 2-trifluoromethoxyphenyl | 381 | 1.66 |
| 56 | 6-methoxypyridin-3-yl | 328 | 1.38 |
| 57 | pyridin-3-yl | 298 | 0.61 |
| 58 | quinolin-8-yl | 348 | 1.32 |
| 59 | 4-trifluoromethoxyphenyl | 381 | |
| 60 | 2,3-dichlorophenyl | 365 | 1.75 |
| 61 | 2,4-difluorophenyl | 333 | 1.66 |
| 62 | 3,4-dimethoxyphenyl | 357 | 1.38 |
| 63 | 4-cyanophenyl | 322 | 1.66 |
| 64 | 3-cyanophenyl | 322 | 1.65 |
| 65 | naphthalen-2-yl | 347 | 1.70 |
| 66 | naphthalen-1-yl | 347 | 1.57 |
| 67 | 3-acetylaminophenyl | 354 | 1.33 |
| 68 | 2-trifluoromethylphenyl | 365 | 1.69 |
| 69 | 4-trifluoromethylphenyl | 365 | 1.81 |
| 70 | 3,5-dichlorophenyl | 365 | 1.87 |
| 71 | 3-trifluoromethylphenyl | 365 | 1.75 |
| 72 | 4-methylsulfonylaminophenyl | 390 | 1.29 |
| 73 | 3,4-difluorophenyl | 333 | 1.74 |
| 74 | 3,5-difluorophenyl | 333 | 1.78 |
| 75 | 4-tert-butylphenyl | 353 | 1.72 |
| 76 | 4-ethoxyphenyl | 341 | 1.53 |
| 77 | 2-fluoropyridin-3-yl | 316 | 1.43 |
| 78 | 2,5-difluorophenyl | 333 | |
| 79 | 4-dimethylaminophenyl | 340 | 1.32 |
| 80 | 3-chloropyridin-4-yl | 332 | 1.39 |
| 81 | 3-methylsulfonylaminophenyl | 390 | 1.32 |
| 82 | 5-cyanothiophen-2-yl | 328 | 1.70 |
| 83 | 3,5-dimethylisoxazol-4-yl | 316 | 1.26 |
| 84 | 3-fluoropyridin-4-yl | 316 | |
| 85 | 4-fluoro-2-methylphenyl | 329 | 1.37 |
| 86 | 4-fluoro-3-methylphenyl | 329 | 1.36 |
| 87 | pyrimidin-5-yl | 299 | 0.96 |

Sample $^1$H-NMR data of compounds of formula Ie (determined in D$_6$-DMSO):

Example 60: δ (ppm)=2.65 (s, 4H), 3.75 (m, 2H), 4.25 (m, 2H), 7.45 (m, 1H), 7.5 (m, 2H), 7.64 (d, 1H), 7.68 (m, 1H), 8.34 (s, 1H).

Example 73: δ (ppm)=2.65 (s, 4H), 3.75 (m, 2H), 4.25 (m, 2H), 7.45-7.55 (m, 2H), 7.38 (m, 1H), 7.96 (d, 1H), 8.06 (m, 1H), 8.30 (s, 1H).

Example 86: δ (ppm)=2.28 (s, 3H) 2.65 (s, 4H), 3.78 (m, 2H), 4.22 (m, 2H), 7.20 (t, 1H), 7.46 (d, 1H), 7.83 (m, 1H), 7.90 (d, 1H), 7.94 (m, 1H), 8.30 (s, 1H).

Determination of the Biological Activity

A) Activation of eNOS Transcription

Activation of eNOS transcription was measured as described in detail by L[1] et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

Numerous compounds of the instant invention were tested by the above-described assay and found to increase protein transcription. Generally, the tested compounds exhibited $EC_{50}$ values of less than about 50 μM. Preferred compounds, including the compounds of examples 7, 17, 34, 64, 66, for example, exhibited $EC_{50}$ values of from about 5 μM to about 0.5 μM. More preferred compounds, including the compounds of examples 18, 25, 50, 52, 86, for example, exhibited $EC_{50}$ values of less than about 0.5 μM.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The effect of the compounds of the formulae I and Ia can also be investigated in the following animal models (animal experiments are performed in accordance with the German animal protection law and the guidelines for the use of experimental animals as given by the Guide for the Care and Use of Laboratory Animals of the US National Institutes of Health). Animals and Treatment (Experiments B-D)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).

B) Anti-Hypertensive Effect in ApoE Knockout Mice

Blood-pressure is determined in conscious mice using a computerized tail-cuff system (Visitech Systems, Apex, Nc). After treatment of ApoE deficient mice and eNOS deficient mice with the test compounds the blood pressure is compared to the results obtained with a placebo treatment.

C) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 μm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

D) Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red 0 staining. For quantifying the effect of the respective compound on vascular eNOS expression the femoral arteries are used in this experiment. The results obtained in the compound group are compared to those obtained in the placebo group.

D) Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using specialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:

1. A compound of formula I,

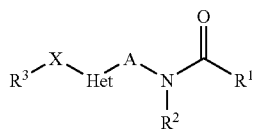

wherein:
A is —$CH_2$—$CH_2$—, —$CH_2$—$CH_2$—$CH_2$— or —Y—$CH_2$—$CH_2$—, wherein all $CH_2$ groups are optionally substituted by one or more identical or different substituents $R^4$, and wherein Y is O, S or $NR^{11}$;
Het is a pyridinediyl group optionally substituted by one or more identical or different substituents $R^5$;
X is a direct bond or $CH_2$;
$R^1$ and $R^2$, together with the N—CO group to which they are attached, form a 2-oxo-pyrrolidin-1-yl or a 2,5-dioxo-pyrrolidin-1-yl ring optionally substituted by one or more identical or different substituents $R^8$;
$R^3$ is phenyl or naphthalenyl, each of which is optionally substituted by one or more identical or different substituents selected from the group consisting of halogen, $(C_1-C_4)$-alkyl, $(C_1-C_4)$-alkyloxy-$(C_1-C_2)$-alkyl-, OH, $(C_1-C_4)$-alkyloxy, $(C_1-C_2)$-alkylenedioxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein the substituents $(C_1-C_4)$-alkyloxy and $(C_1-C_2)$-alkylenedioxy are independently optionally substituted by one or more fluorine atoms;
$R^4$ is $(C_1-C_4)$-alkyl or fluorine;
$R^5$ is halogen, $(C_1-C_4)$-alkyl, $(C_1-C_4)$-alkyloxy-$(C_1-C_2)$-alkyl-, OH, $(C_1-C_4)$-alkyloxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ or $(C_1-C_4)$-alkyl-$SO_2$—, wherein the substituent $(C_1-C_4)$-alkyloxy is optionally substituted by one or more fluorine atoms;
$R^8$ is halogen, $(C_1-C_4)$-alkyl, $(C_3-C_7)$-cycloalkyl-$C_nH_{2n}$—, phenyl-$C_nH_{2n}$—, $(C_1-C_4)$-alkyloxy-$(C_1-C_2)$-alkyl-, OH, oxo, $(C_1-C_4)$-alkyloxy, $(C_1-C_2)$-alkylenedioxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— or $(C_1-C_4)$-alkyl-$SO_2$—, wherein the substituents $(C_1-C_4)$-alkyloxy and $(C_1-C_2)$-alkylenedioxy are independently optionally substituted by one or more fluorine atoms, and all phenyl groups are independently of each other optionally substituted by one or more identical or different substituents selected from the group consisting of halogen, $(C_1-C_4)$-alkyl, $CF_3$ and $(C_1-C_4)$-alkyloxy;
$R^{11}$ is hydrogen, $(C_1-C_4)$-alkyl or $((C_1-C_4)$-alkyl)-CO—; and
n is 0, 1 or 2;
or its stereoisomeric form or a mixture of stereoisomeric forms in any ratio, or a physiologically acceptable salt thereof;
provided that the compound of formula I is not:
2-amino-6-(2-(2-oxopyrrolidin-1-yl)ethylamino)-4-phenylpyridine-3,5-dicarbonitrile.

2. The compound according to claim 1, wherein:
$R^3$ is phenyl or naphthalenyl, each of which is optionally substituted by one or more identical or different substituents selected from the group consisting of halogen, $(C_1-C_4)$-alkyl, $(C_1-C_4)$-alkyloxy-$(C_1-C_2)$-alkyl-, $(C_1-C_4)$-alkyloxy, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—, wherein the substituent $(C_1-C_4)$-alkyloxy is optionally substituted by one or more fluorine atoms;
or its stereoisomeric form or a mixture of stereoisomeric forms in any ratio, or a physiologically acceptable salt thereof.

3. The compound according to claim 1, wherein:
$R^3$ is phenyl optionally substituted by one or more identical or different substituents selected from the group consisting of halogen, $(C_1-C_4)$-alkyl, $(C_1-C_4)$-alkyloxy-$(C_1-C_2)$-alkyl-, $(C_1-C_4)$-alkyloxy, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—, wherein the substituent $(C_1-C_4)$-alkyloxy is optionally substituted by one or more fluorine atoms;
or its stereoisomeric form or a mixture of stereoisomeric forms in any ratio, or a physiologically acceptable salt thereof.

4. The compound according to claim 1, wherein:
A is —$CH_2$—$CH_2$—$CH_2$— or —Y—$CH_2$—$CH_2$—, wherein Y is O or NH;
Het is a pyridinediyl group, which is optionally substituted by one or more identical or different substituents $R^5$;
X is a direct bond;
$R^1$ and $R^2$, together with the N—CO group to which they are attached, form a 2-oxo-pyrrolidin-1-yl or a 2,5-dioxo-pyrrolidin-1-yl ring optionally substituted by one or more identical or different substituents $R^8$;
$R^3$ is phenyl optionally substituted by one or more identical or different substituents selected from the group consisting of halogen, $(C_1-C_4)$-alkyl, $(C_1-C_4)$-alkyloxy-$(C_1-C_2)$-alkyl-, $(C_1-C_4)$-alkyloxy, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—, wherein the substituent $(C_1-C_4)$-alkyloxy is optionally substituted by one or more fluorine atoms;
$R^5$ is halogen, $(C_1-C_4)$-alkyl, $(C_1-C_4)$-alkyloxy-$(C_1-C_2)$-alkyl-, OH, $(C_1-C_4)$-alkyloxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ or $(C_1-C_4)$-alkyl-$SO_2$—, wherein the substituent $(C_1-C_4)$-alkyloxy is optionally substituted by one or more fluorine atoms;
$R^8$ is $(C_1-C_4)$-alkyl or oxo;
or its stereoisomeric form or a mixture of stereoisomeric forms in any ratio, or a physiologically acceptable salt thereof.

5. The compound according to claim 1, wherein X is a direct bond, or its stereoisomeric form or a mixture of stereoisomeric forms in any ratio, or a physiologically acceptable salt thereof.

6. The compound according to claim 1, wherein:
A is —$CH_2$—$CH_2$—$CH_2$— or —Y—$CH_2$—$CH_2$—, wherein Y is O or NH;
Het is a pyridinediyl group, which is optionally substituted by one or more identical or different substituents $R^5$;
X is a direct bond;
$R^1$ and $R^2$, together with the N—CO group to which they are attached, form a 2-oxo-pyrrolidin-1-yl or a 2,5-dioxo-pyrrolidin-1-yl ring optionally substituted by one or more identical or different substituents $R^8$;
$R^3$ is phenyl substituted by one or more identical or different substituents selected from the group consisting of halogen, ($C_1$-$C_4$)-alkyl, ($C_1$-$C_4$)-alkyloxy-($C_1$-$C_2$)-alkyl-, ($C_1$-$C_4$)-alkyloxy, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—, wherein the substituent ($C_1$-$C_4$)-alkyloxy is optionally substituted by one or more fluorine atoms;
$R^5$ is halogen, ($C_1$-$C_4$)-alkyl, ($C_1$-$C_4$)-alkyloxy-($C_1$-$C_2$)-alkyl-, OH, ($C_1$-$C_4$)-alkyloxy, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—, wherein the substituent ($C_1$-$C_4$)-alkyloxy is optionally substituted by one or more fluorine atoms;
$R^8$ is ($C_1$-$C_4$)-alkyl or oxo;
or its stereoisomeric form or a mixture of stereoisomeric forms in any ratio, or a physiologically acceptable salt thereof.

7. The compound according to claim 1, wherein:
A is —$CH_2$—$CH_2$—$CH_2$— or —Y—$CH_2$—$CH_2$—, wherein Y is O or NH;
Het is a-pyridinediyl group, which is optionally substituted by one or more identical or different substituents $R^5$;
X is a direct bond;
$R^1$ and $R^2$, together with the N—CO group to which they are attached, form a 2-oxo-pyrrolidin-1-yl or a 2,5-dioxo-pyrrolidin-1-yl ring optionally substituted by one or more identical or different substituents $R^8$;
$R^3$ is phenyl optionally substituted by one or more identical or different substituents selected from the group consisting of halogen, ($C_1$-$C_4$)-alkyl, ($C_1$-$C_4$)-alkyloxy-($C_1$-$C_2$)-alkyl-, ($C_1$-$C_4$)-alkyloxy, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—, wherein the substituent ($C_1$-$C_4$)-alkyloxy is optionally substituted by one or more fluorine atoms;
$R^5$ is halogen, ($C_1$-$C_4$)-alkyl or $CF_3$;
$R^8$ is ($C_1$-$C_4$)-alkyl or oxo;
or its stereoisomeric form or a mixture of stereoisomeric forms in any ratio, or a physiologically acceptable salt thereof.

8. The compound according to claim 1, which is
1-(3-(6-(2-fluorophenyl)pyridin-3-yl)propyl)pyrrolidin-2-one,
1-(3-(6-(2-fluorophenyl)pyridin-3-yl)propyl)pyrrolidine-2,5-dione,
1-(3-(6-(4-fluorophenyl)pyridin-3-yl)propyl)pyrrolidin-2-one,
1-(3-(6-(4-fluorophenyl)pyridin-3-yl)propyl)pyrrolidine-2,5-dione,
1-(2-(6-(2-fluorophenyl)pyridin-3-yloxy)ethyl)pyrrolidine-2,5-dione,
1-(2-(5-(2-fluorophenyl)pyridin-2-yloxy)ethyl)pyrrolidin-2-one,
1-(2-(6-(4-fluorophenyl)pyridin-3-yloxy)ethyl)pyrrolidine-2,5-dione,
1-(2-(6-(3-chloro-4-fluorophenyl)pyridin-3-yloxy)ethyl)pyrrolidine-2,5-dione,
1-(2-(6-(3,4,5-trifluorophenyl)pyridin-3-yloxy)ethyl)pyrrolidine-2,5-dione,
1-(2-(6-(3-trifluoromethoxyphenyl)pyridin-3-yloxy)ethyl)pyrrolidine-2,5-dione,
1-(2-(6-(2-trifluoromethoxyphenyl)pyridin-3-yloxy)ethyl)pyrrolidine-2,5-dione,
1-(2-(6-(4-trifluoromethoxyphenyl)pyridin-3-yloxy)ethyl)pyrrolidine-2,5-dione,
1-(2-(6-(2,3-dichlorophenyl)pyridin-3-yloxy)ethyl)pyrrolidine-2,5-dione,
1-(2-(6-(2,4-difluorophenyl)pyridin-3-yloxy)ethyl)pyrrolidine-2,5-dione,
1-(2-(6-(3,4-dimethoxyphenyl)pyridin-3-yloxy)ethyl)pyrrolidine-2,5-dione,
1-(2-(6-(4-cyanophenyl)pyridin-3-yloxy)ethyl)pyrrolidine-2,5-dione,
1-(2-(6-(3-cyanophenyl)pyridin-3-yloxy)ethyl)pyrrolidine-2,5-dione,
1-(2-(6-(naphthalen-2-yl)pyridin-3-yloxy)ethyl)pyrrolidine-2,5-dione,
1-(2-(6-(naphthalen-1-yl)pyridin-3-yloxy)ethyl)pyrrolidine-2,5-dione,
1-(2-(6-(3-acetylaminophenyl)pyridin-3-yloxy)ethyl)pyrrolidine-2,5-dione,
1-(2-(6-(2-trifluoromethylphenyl)pyridin-3-yloxy)ethyl)pyrrolidine-2,5-dione,
1-(2-(6-(4-trifluoromethylphenyl)pyridin-3-yloxy)ethyl)pyrrolidine-2,5-dione,
1-(2-(6-(3,5-dichlorophenyl)pyridin-3-yloxy)ethyl)pyrrolidine-2,5-dione,
1-(2-(6-(3-trifluoromethylphenyl)pyridin-3-yloxy)ethyl)pyrrolidine-2,5-dione,
1-(2-(6-(3,4-difluorophenyl)pyridin-3-yloxy)ethyl)pyrrolidine-2,5-dione,
1-(2-(6-(3,5-difluorophenyl)pyridin-3-yloxy)ethyl)pyrrolidine-2,5-dione,
1-(2-(6-(4-tert-butylphenyl)pyridin-3-yloxy)ethyl)pyrrolidine-2,5-dione,
1-(2-(6-(4-ethoxyphenyl)pyridin-3-yloxy)ethyl)pyrrolidine-2,5-dione,
1-(2-(6-(2,5-difluorophenyl)pyridin-3-yloxy)ethyl)pyrrolidine-2,5-dione,
1-(2-(6-(4-dimethylaminophenyl)pyridin-3-yloxy)ethyl)pyrrolidine-2,5-dione,
1-(2-(6-(4-fluoro-2-methylphenyl)pyridin-3-yloxy)ethyl)pyrrolidine-2,5-dione,
1-(2-(6-(4-fluoro-3-methylphenyl)pyridin-3-yloxy)ethyl)pyrrolidine-2,5-dione, or
or a physiologically acceptable salt thereof.

9. A pharmaceutical composition, comprising an effective amount of the compound according to claim 1 or its stereoisomeric form or a mixture of stereoisomeric forms in any ratio, or a physiologically acceptable salt thereof, and a pharmaceutically acceptable carrier.

* * * * *